United States Patent
Lippoff et al.

(10) Patent No.: US 11,289,208 B1
(45) Date of Patent: Mar. 29, 2022

(54) APPOINTMENT MONITORING AND TRACKING SYSTEM

(71) Applicant: AA DATABIT LLC, Brooklyn, NY (US)

(72) Inventors: Orrin Lippoff, Brooklyn, NY (US); Mladen Solar, Brooklyn, NY (US)

(73) Assignee: AA DATABIT LLC, Brooklyn, NY (US)

( * ) Notice: Subject to any disclaimer, the term of this patent is extended or adjusted under 35 U.S.C. 154(b) by 0 days.

(21) Appl. No.: 17/061,597

(22) Filed: Oct. 2, 2020

Related U.S. Application Data

(63) Continuation-in-part of application No. 15/825,846, filed on Nov. 29, 2017, now Pat. No. 10,832,823.

(60) Provisional application No. 62/432,186, filed on Dec. 9, 2016.

(51) Int. Cl.

| | |
|---|---|
| *G16H 80/00* | (2018.01) |
| *G16H 10/60* | (2018.01) |
| *G06F 9/54* | (2006.01) |
| *H04M 7/12* | (2006.01) |
| *G16H 40/20* | (2018.01) |
| *H04L 51/046* | (2022.01) |

(52) U.S. Cl.
CPC ............ *G16H 80/00* (2018.01); *G06F 9/547* (2013.01); *G16H 10/60* (2018.01); *G16H 40/20* (2018.01); *H04L 51/046* (2013.01); *H04M 7/1295* (2013.01)

(58) Field of Classification Search
CPC ........ G16H 80/00; G16H 40/20; G16H 10/60; G06F 9/547; H04L 51/046; H04M 7/1295
See application file for complete search history.

(56) References Cited

U.S. PATENT DOCUMENTS

| | | | | |
|---|---|---|---|---|
| 5,524,147 | A * | 6/1996 | Bean .................... | H04M 3/5237 379/266.03 |
| 6,385,202 | B1 * | 5/2002 | Katseff ............. | H04M 3/53333 370/352 |
| 7,068,777 | B1 * | 6/2006 | Belhaj ................... | H04M 1/505 379/355.02 |
| 8,295,452 | B1 * | 10/2012 | Trandal ................. | H04M 7/003 379/93.12 |
| 8,345,856 | B1 * | 1/2013 | Anisimov ........... | H04M 3/5158 379/265.1 |
| 8,804,944 | B1 * | 8/2014 | Hopkins ............. | H04M 3/5166 379/266.01 |
| 9,992,330 | B1 * | 6/2018 | Hodge .................... | H04M 3/38 |
| 9,996,666 | B1 * | 6/2018 | Wilson ................ | G06F 16/9537 |

(Continued)

OTHER PUBLICATIONS

Non-Final Office Action received for U.S. Appl. No. 15/825,846 dated Apr. 18, 2019, 14 pages.

(Continued)

*Primary Examiner* — Jerry B Dennison
(74) *Attorney, Agent, or Firm* — FisherBroyles, LLP

(57) ABSTRACT

A computer system includes a client-side presentation layer processor; a server-side service layer component including at least one application programming interface (API) controller, at least one repository pattern processor, and a data layer processor; and a back-end layer component comprising at least one structured query language (SQL) server and a cache, wherein the client-side presentation layer processor interprets conversational modes directed to dialogues programmed in the computer system.

20 Claims, 31 Drawing Sheets

(56) References Cited

U.S. PATENT DOCUMENTS

| | | |
|---|---|---|
| 10,552,930 B1 | 2/2020 | Jordan-Nowe et al. |
| 10,832,823 B1* | 11/2020 | Lippoff .................. G16H 80/00 |
| 11,005,988 B1* | 5/2021 | Patakokila .......... H04M 3/4286 |
| 11,037,658 B2* | 6/2021 | Cox ........................ G16H 40/67 |
| 2002/0133386 A1 | 9/2002 | Chishti et al. |
| 2005/0027567 A1* | 2/2005 | Taha ....................... G16H 10/20 |
| | | 705/2 |
| 2006/0106644 A1* | 5/2006 | Koo ........................ G16H 10/60 |
| | | 705/3 |
| 2007/0032223 A1* | 2/2007 | Alberth, Jr. .......... H04M 1/2757 |
| | | 455/416 |
| 2008/0046289 A1 | 2/2008 | Compton et al. |
| 2008/0046290 A1 | 2/2008 | Compton et al. |
| 2008/0080386 A1* | 4/2008 | Calahan .............. H04L 43/0817 |
| | | 370/252 |
| 2008/0147741 A1* | 6/2008 | Gonen ................... G16H 10/60 |
| 2008/0215365 A1* | 9/2008 | Groan .................... G16H 40/60 |
| | | 705/2 |
| 2010/0106518 A1 | 4/2010 | Kuo |
| 2011/0119075 A1 | 5/2011 | Dhoble |
| 2012/0323997 A1* | 12/2012 | Mezhibovsky ......... H04L 67/18 |
| | | 709/204 |
| 2013/0064358 A1* | 3/2013 | Nusbaum .......... H04M 3/42068 |
| | | 379/88.16 |
| 2013/0191185 A1* | 7/2013 | Galvin ................... G06Q 10/10 |
| | | 705/7.37 |
| 2013/0271470 A1* | 10/2013 | Moore ................... G16H 10/60 |
| | | 345/440.1 |
| 2013/0282391 A1 | 10/2013 | Easterhaus et al. |
| 2013/0282397 A1 | 10/2013 | Easterhaus et al. |
| 2013/0290007 A1* | 10/2013 | Haq ....................... G16H 40/20 |
| | | 705/2 |
| 2013/0325503 A1 | 12/2013 | Abrahams et al. |
| 2014/0108030 A1 | 4/2014 | Tejeda-Monteagut |
| 2014/0249878 A1* | 9/2014 | Kaufman ........... G06Q 10/1095 |
| | | 705/7.19 |
| 2014/0278480 A1 | 9/2014 | Baniameri et al. |
| 2014/0278550 A1 | 9/2014 | Pestka |
| 2014/0288949 A1* | 9/2014 | Eromo ............... G06Q 20/3223 |
| | | 705/2 |
| 2014/0297318 A1* | 10/2014 | Prasad ................... G16H 10/60 |
| | | 705/3 |
| 2014/0301538 A1* | 10/2014 | Aghor ................. H04M 3/5158 |
| | | 379/88.22 |
| 2014/0304003 A1 | 10/2014 | Sethumadhavan et al. |
| 2014/0309993 A1* | 10/2014 | Goussard .............. G10L 15/063 |
| | | 704/231 |
| 2015/0261917 A1* | 9/2015 | Smith ................. G06F 21/6263 |
| | | 705/3 |
| 2015/0278975 A1 | 10/2015 | Mien |
| 2015/0281949 A1* | 10/2015 | La ....................... G06F 21/6245 |
| | | 455/411 |
| 2015/0310173 A1 | 10/2015 | Coney |
| 2015/0356248 A1 | 12/2015 | Kogan et al. |
| 2016/0004833 A1* | 1/2016 | Patil ...................... G16H 10/60 |
| | | 705/3 |
| 2016/0012465 A1* | 1/2016 | Sharp .................. G06Q 20/386 |
| | | 705/14.17 |
| 2016/0048660 A1 | 2/2016 | Lulias et al. |
| 2016/0132969 A1* | 5/2016 | Gunjan ................. G06Q 40/08 |
| | | 705/4 |
| 2016/0140297 A1 | 5/2016 | Wisnicki |
| 2016/0147972 A1 | 5/2016 | Mancine et al. |
| 2016/0239614 A1* | 8/2016 | Siva ........................ G06F 16/22 |
| 2016/0246926 A1 | 8/2016 | Morefield |
| 2016/0321412 A1* | 11/2016 | Basri ..................... G16H 10/60 |
| 2017/0032092 A1* | 2/2017 | Mink ................. G06Q 30/0241 |
| 2017/0061077 A1 | 3/2017 | Cline et al. |
| 2017/0103177 A1 | 4/2017 | Iliff et al. |
| 2018/0108442 A1 | 4/2018 | Borve |
| 2018/0182014 A1 | 6/2018 | Cheng |
| 2019/0392922 A1* | 12/2019 | Bader .................... G16H 10/60 |
| 2021/0105271 A1* | 4/2021 | Nitturkar .............. H04W 12/06 |
| 2021/0232954 A1* | 7/2021 | Monaghan ............ G06N 5/045 |
| 2021/0241869 A1* | 8/2021 | Muse ..................... H04L 63/04 |
| 2021/0248195 A1* | 8/2021 | Okajima ............. G06F 16/9532 |

OTHER PUBLICATIONS

Final Office Action received for U.S. Appl. No. 15/825,846 dated Dec. 6, 2019, 28 pages.

Non-Final Office Action received for U.S. Appl. No. 15/825,846 dated Mar. 2, 2020, 28 pages.

Notice of Allowance received for U.S. Appl. No. 15/825,846 dated Jul. 20, 2020, 26 pages.

* cited by examiner

FIG. 9

| Name | Symbol | Description |
|---|---|---|
| Task | | A task may be a unit of work – the job to be performed. It may be an atomic activity within a process flow. |
| Sub-process | | A collapsed sub-process may be a decomposable activity. It may be linked to another process diagram. |
| Exclusive Gateway | | Evaluates the state of the system process and, based on the condition, breaks the flow into one or more mutually exclusive paths |
| Parallel Gateway | | When used to split the sequence flow, all outgoing branches may be activated simultaneously. When merging parallel branches, it waits for all incoming branches to complete before triggering the outgoing flow. |
| Inclusive Gateway | | Breaks the process flow into one or more flows, when splitting, one or more branches may be activated based on branching conditions. When merging, it awaits all active incoming branches to complete. |
| Text Annotation | | Any object may be associated with a text annotation to provide additional documentation. |
| Message | | A message may be used to depict the contents of a communication between two participants. |
| Data Store | | A data store may be a place where the process may read or write data, e.g. a database or a filling cabinet. It persists beyond the lifetime of the process instance. |
| Start Event | | Start event that triggers a new process instance. |
| Start Message Event | | A process instance may be started on receipt of a message. |
| Start Conditional Event | | A process instance may be started based on changed system conditions or matching system rules |
| Intermediate Message Event | | This event reacts on the arrival of a message. |
| Intermedia Conditional Event | | Process execution may be delayed until a changed system condition or system rule matches. |
| End Event | | The end event typically marks the standard end of a process. |
| Sequence Flow | | Sequence flow defines the execution order of activities. |
| Message Flow | | Message flow symbolizes information flow across organizational boundaries. Message flow may be attached to pools, activities or message events. The order of message exchanges may be specified by combining message flow and sequence flow. |

APPOINTMENT MONITORING AND TRACKING SYSTEM

CROSS-REFERENCE TO RELATED APPLICATIONS

This application is a continuation-in-part of U.S. application Ser. No. 15/825,846 filed Nov. 29, 2017, which claims priority to U.S. Provisional Application No. 62/432,186, filed Dec. 9, 2016, which are incorporated by reference herein in their entireties.

BACKGROUND

Field

The disclosed embodiments generally relate to a computer system that includes a client-side presentation layer processor; a server-side service layer component including one or more API controllers, at least one repository pattern processor, and a data layer processor; and a back-end layer component including at least one SQL server and a cache.

SUMMARY

An exemplary aspect includes a computer system that has a client-side presentation layer processor; a server-side service layer component including one or more API controllers, at least one repository pattern processor, and a data layer processor; and a back-end layer component including at least one SQL server and a cache.

In various exemplary embodiments: (a) the presentation layer processor includes one or more controllers; (b) the one or more API controllers provide application security and authentication; and (c) the data layer processor includes at least one data access component.

One or more embodiments may include a system to track and improve referral coordination between primary-care providers and subspecialty physicians, and to provide hospitals and healthcare networks with access to referral patterns of associated providers.

In an embodiment, this system provides online access to a server-side system utilizing a secure portal, which enables primary care physicians to choose subspecialty referrals for patients from a list of pre-populated subspecialty physicians within a healthcare or hospital network.

In an embodiment, physicians may add new subspecialty physicians outside hospital or healthcare network, if a subspecialist may be not affiliated with an associated hospital or network; the added subspecialist may be considered a "leakage" referral, which may be identified to a hospital or healthcare network in a reporting module.

In an embodiment, the system also may provide notification and tracking of patients admitted to emergency departments or hospitals to primary care providers via secure email notification. Upon patient discharge, the system may contact the patient to schedule an appointment with a primary care or family practice provider, to reduce the likelihood of readmission for the same complaint within certain time period (e.g., 30 days).

Specific numerical values, time periods, codes, and messages described herein may be intended only to be illustrative, and do not limit the scope of the described system or claimed invention in any manner Administrators and coordinators described herein may be software or hardware modules or circuits.

One or more embodiments of the system may track patient referral appointments on specific timeframes, in order to facilitate a subspecialist's report to a requesting primary care provider in a short time interval, which is configurable.

In an embodiment, the system automatically tracks a patient's appointment date and time, and thereafter contacts a subspecialty office via email to expedite subspecialty consult report generation for a primary care physician, in order to optimize patient care.

Additionally, in an embodiment, the system tracks patients who refuse to make an appointment with a subspecialist, or may be a no-show for a scheduled appointment. The system may notify the primary care provider automatically in such instances.

In an embodiment, the system accesses information from a subspecialty office on a secure portal, in order to retrieve notification if a patient missed or canceled an appointment.

In an embodiment, the system updates a primary care provider with updated information, which allows the primary care provider to reach out to patients based on importance of a subspecialty referral request, especially when importance of a requested referral may be paramount for disease management of a patient.

In an embodiment, the system provides a primary care provider with passive notifications via a system portal on a secure link to an affiliated hospital, when a patient may be admitted to an emergency room or hospital. Physicians may be notified on a mobile device in order to provide appropriate and timely treatment for patients that have been admitted to an emergency department ("ED") or hospital.

In an embodiment, the system identifies referral density patterns of subspecialty referrals based on primary care provider referral requests. This allows healthcare systems and hospitals to identify areas of need for subspecialists, based on those referral density patterns. The identification and subsequent placement of subspecialists in areas identified by the system may increase patient compliance with referral requests by providing patients the opportunity to see subspecialists in close proximity to their primary care physicians' offices.

The system thus provides several technical solutions for subspecialty referral and hospital discharge coordination, and enhances disease management while reducing risks associated with patient care for primary care physicians.

One object and feature of an embodiment is to allow physicians to access all outstanding referrals which have been requested utilizing a HIPAA secure portal. Additionally, utilization of the system may provide greater reassurance that a patient will complete a referral appointment requested from a primary care provider to a subspecialty physician.

It is a further object and feature of an embodiment to provide a system which may automatically follow-up on a patient's appointment with a subspecialist to verify that the appointment has been completed, by updating a primary care physician who requested the referral. The system also may update a primary care physician if a patient refuses a referral or was a no-show.

It is a further object and feature of an embodiment to provide a system that enables authorized persons utilizing the system to track referral patterns within a healthcare network, to ascertain referral density patterns based on primary care physician requests, patient needs, and distances required for patients to travel to obtain referral appointments.

It is a further object and feature of an embodiment to enable healthcare and hospital networks to better align primary care referrals for their patients within a close geographic proximity to primary care offices. In addition the system may enhance connectivity linkage between primary-care providers and subspecialty physicians within the same healthcare or hospital network, in order to enable improved exchange of medical information among primary care providers and subspecialty physicians.

It is a further object and feature of an embodiment for the system to notify primary care and family based physicians when patients may be admitted to an emergency department or a hospital within a healthcare network. Primary-care physicians may be immediately notified upon registration of their patients via secure notification to smart phone or email devices.

It is a further object and feature of an embodiment for the system to notify primary care physicians when patients may be discharged by a hospital or healthcare network and to provide tracking of patient's status until discharge. Upon discharge, patients may be contacted by the system to schedule patients for appointments with primary care providers within, say, 48 hours of hospital discharge.

This system may maintain tracking of all hospital and emergency room admissions within a healthcare network, and provide authorized personnel within a healthcare network the ability to track admissions to emergency rooms and hospitals of patients of primary care and family practitioners.

In an embodiment, the system tracks patients discharged from an ED or hospital through a secure link with an associated hospital. Upon discharge notification, a referral coordinator may reach out to a patient to schedule an appointment with the patient's primary care provider.

The system therefore reduces the likelihood of a patient's readmission to an emergency department or hospital as a consequence of enhanced care provided through the system.

In an embodiment, the system identifies referral density patterns of subspecialty referrals based on primary care provider referral requests. This allows healthcare systems and hospitals to identify areas of need for subspecialists, based on those referral density patterns. The identification and subsequent placement of subspecialists in areas identified by the system may increase patient compliance with referral requests by providing patients the opportunity to see subspecialists in close proximity to their primary care physicians' offices.

In an embodiment, the system reduces likelihood of re-admittance of patients to emergency rooms or hospitals through its coordinated effort to align patients with their primary care providers, by coordinating appointments within, for example, a 30 day window after discharge and by contacting patients within, for example, 48 hours of discharge.

One or more embodiments may include an appointment tracking and monitoring system to track and improve referral coordination between patients and specialty physicians.

In an embodiment, a computer system includes a client-side presentation layer processor; a server-side service layer component including at least one application programming interface (API) controller, at least one repository pattern processor, and a data layer processor; and a back-end layer component comprising at least one structured query language (SQL) server and a cache, wherein the client-side presentation layer processor interprets conversational modes directed to dialogues programmed in the computer system.

The presentation layer processor may include at least one processing device, and the at least one API controller may provide at least one of application security and/or authentication. The data layer processor may include at least one data access component, and the server-side service layer component may validate an insurance authorization status associated with at least one of a patient and/or referral. The server-side service layer component may utilize a URL hyperlink to submit a referral request, and the client-side presentation layer processor may transmit a special note provided by a primary care provider to a specialist that provides referral coordination. The special note may include information associated with at least one of physical examination and/or diagnostic study based on patient pathology.

Demographic information associated with a physician and demographic information associated with a patient may be provided by a referral system to the server-side service layer component. In response to at least one of a patient refusing to make an appointment and/or patient could not be reached, the client-side presentation layer may transmit a notification to a primary care provider identifying the patient and at least one of that the patient refused to make a referral appointment and/or that the patient could not be reached. In response to a patient being unreachable, the client-side presentation layer processor may transmit a notification to at least one of a primary care provider and/or patient indicating an inability to coordinate a referral request by the primary care provider.

The client-side presentation layer processor may initiate a call to a physician after placing an active call to a patient on hold. The client-side presentation layer processor may initiate a call to a patient after placing an active call to a physician on hold. The client-side presentation layer processor may alternate between picking up active calls with at least one of a physician's office and/or a patient until an agreement is reached between the physician's office and patient. The agreement may be associated with a date and time of an appointment for the patient with the physician, and the client-side presentation layer processor may confirm an appropriate date and time of an appointment with at least one of a physician and/or a patient. The client-side presentation layer processor may cause a dual-tone multi-frequency (DTMF) tone to be generated in response to interfacing with at least one of an interactive voice response (IVR) system, music on hold, and/or an answering machine. The DTMF tone may represent at least one of 0, 1, and/or 9. The DTMF tone may represent a digital tone associated with access to at least one of an operator, and/or receptionist, thereby establishing connection with a person. The client-side presentation layer processor may wait a predetermined time period for a person to answer a call in response to interfacing with at least one of an interactive voice response (IVR) system, music on hold, answering machine before advising the patient that an appointment cannot be made at this time.

It is to be noted that any and/or each of the features, functions, tasks, and the like disclosed herein can be performed by any and/or each of the client-side presentation layer processor, server-side service layer component, application programming interface controller, repository pattern processor, data layer processor, back-end layer component, structured query language server without limitation.

Other embodiments will become apparent from the following detailed description considered in conjunction with the accompanying drawings. It is to be understood, however, that the drawings are designed as an illustration only and not as a definition of the limits of any of the embodiments.

BRIEF DESCRIPTION OF THE DRAWINGS

The following drawings are provided by way of example only and without limitation, wherein like reference numerals (when used) indicate corresponding elements throughout the several views, and wherein:

FIG. 9 defines symbols used in the drawings;

Figure 1:
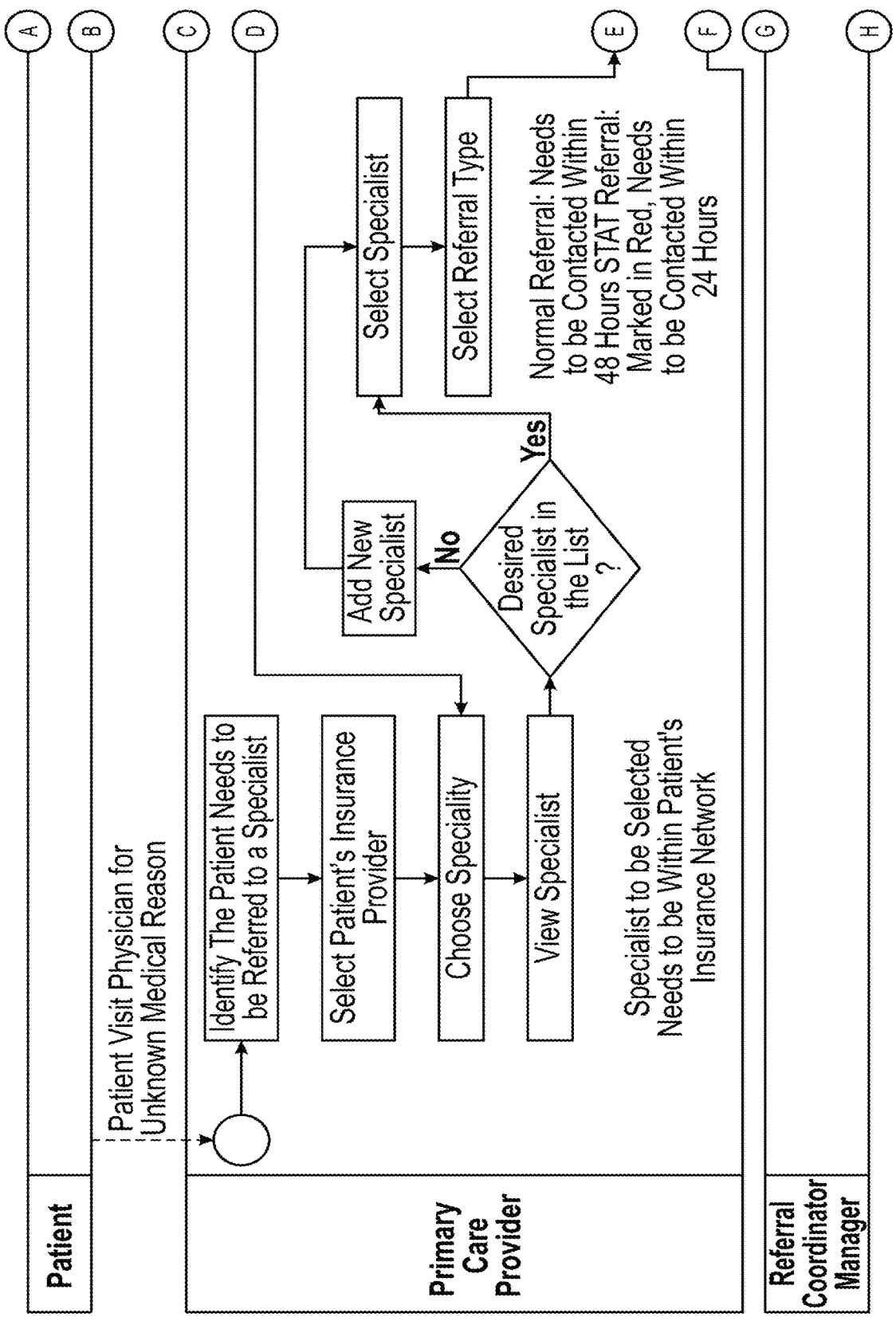
FIG. 1 is a workflow diagram depicting a submit New Referral Process of an exemplary embodiment.
Figure 1:
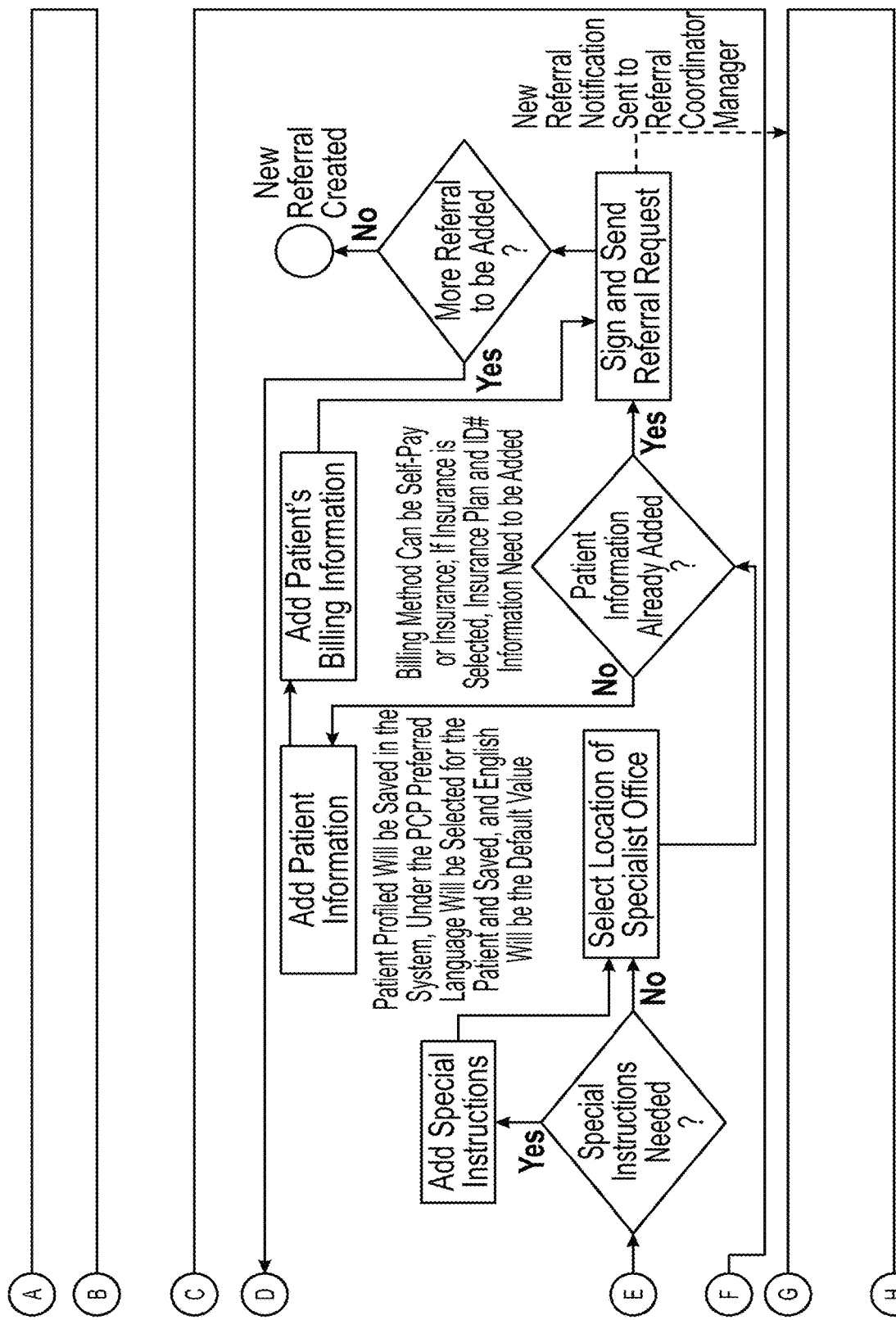

It is to be appreciated that elements in the figures are illustrated for simplicity and clarity. Common but well-understood elements that are useful or necessary in a commercially feasible embodiment are not shown in order to facilitate a less hindered view of the illustrated embodiments.

DETAILED DESCRIPTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

An embodiment comprises a system of referral management services that provides access points between primary-care providers, subspecialists, and one or more hospital or healthcare networks.

This system may provide referral management resources to enable scheduling of patients as requested by primary care providers to subspecialists within a provider network of affiliated physicians, in order to increase the percentage of completed referrals by patients.

This system may facilitate requested subspecialty appointments by primary care provider by acting as a proxy center with the ability to provide requesting provider access through a secure portal to maintain up-to-date information and control of requested referrals The system may generate monthly, quarterly, and/or yearly reports in order to enable primary care physicians and health-care or hospital networks to identify gaps in areas where subspecialties may be required, by analyzing referral density per requests of primary-care providers with regard to subspecialty referrals and based on geographic locations of sub specialty physicians from primary care offices.

The system may increase physician and patient compliance with completing requested referral appointments to subspecialists.

Through utilization of a secure portal the system may track emergency room and hospital admissions in order to provide physician notifications. In addition, the system may provide scheduling of patient appointments upon discharge, with primary care provider, in order to ensure appropriate follow-up care after hospital discharge and to reduce the possibility of readmission within a 30 day window, in order to improve overall disease management of patients.

System Processes: for each system process, the following elements may include:
- Purpose/Scope: this section may provide a description of the purpose and scope of the entire system and system process.
- Workflow Diagram: this section may include a visual diagram of the workflow, indicating the relationship between activities in the process.
- Activity Description: this section may describe each of the activities of the system and system processes.
- Inputs: inputs may be deliverables that a person responsible for initiating the process receives in either physical or electronic form. (A deliverable could be an email, a document, an updated database entry, a fax, etc.)
- Outputs: this section may provide an explanation of the process's outputs or deliverables.
- Roles & Responsibilities: this section may describe the roles and responsibilities; it may be also be possible that one person/module/circuit may fulfill more than one role within a process—or that multiple people modules/circuits may share the same role.

System Rules: this section may include a list of relevant system rules and reference the steps from the Activity description section in which they may be enforced.

System Requirement: this section may include a list of system requirements for the system area discussed.

System Description and Functional Requirement: may list all the desired system features with functional requirements.

Embodiments described herein are intended to provide one or more of the following improvements:

Better Data Quality: The system provides an integrated data platform that seamlessly connects different data sources and workflows. The net result is that the system may provide a single source of data that is real time, up-to-date and accurate.

Automation: The system may enable easier tracking of referrals, ER/hospital admissions, communication, notes, notifications, alerts and key system process artifacts-thereby reducing the amount of duplicate work, manual labor, and unnecessary errors produced during day-to-day operations.

Better Reporting: The system may record and report on operations better, to generate desired reports based on criteria defined, as well as based on a centralized data set.

Knowledge Generation: The system improve the type of information available. The system moves beyond information capture and enables knowledge generation—helping an organization make strategic decisions, identify trends in services provided, and uncover new areas of growth.

In addition to the above stated features, the system is HIPAA Compliant. The passage of the Health Insurance Portability and Accountability Act (HIPAA) by Congress in 1996 has complicated traditional referral request systems. HIPAA establishes rigorous standards for protecting sensitive patient information.

The Final Rule on Security Standards was issued on Feb. 20, 2003. It took effect on Apr. 21, 2003 with a compliance date of Apr. 21, 2005 for most covered entities and Apr. 21, 2006 for "small plans". The Security Rule complements the Privacy Rule. While the Privacy Rule pertains to all Protected Health Information (PHI) including paper and electronic, the Security Rule deals specifically with Electronic Protected Health Information (EPHI). It lays out three types of security safeguards required for compliance: administrative, physical, and technical. For each of these types, the Rule identifies various security standards, and for each standard, it names both required and addressable implementation specifications. Required specifications may be adopted and administered as dictated by the Rule. Addressable specifications may be more flexible. Individual covered entities may evaluate their own situation and determine the best way to implement addressable specifications. Some privacy advocates have argued that this "flexibility" may provide too much latitude to covered entities. The standards and specifications may be as follows:

Administrative Safeguards—policies and procedures designed to clearly show how the entity may comply with the act Covered entities (entities that may comply with HIPAA requirements) may adopt a written set of privacy procedures and designate a privacy officer to be responsible for developing and implementing all required policies and procedures.

The policies and procedures may reference management oversight and organizational buy-in to compliance with the documented security controls.

Procedures may clearly identify employees or classes of employees who may have access to electronic protected health information (EPHI). Access to EPHI may be restricted to only those employees who have a need for it to complete their job function.

The procedures may address access authorization, establishment, modification, and termination.

Entities may show that an appropriate ongoing training program regarding the handling of PHI may be provided to employees performing health plan administrative functions.

Covered entities that out-source some of their system processes to a third party may ensure that their vendors also have a framework in place to comply with HIPAA requirements. Companies typically gain this assurance through clauses in the contracts stating that the vendor may meet the same data protection requirements that apply to the covered entity. Care may be taken to determine if the vendor further out-sources any data handling functions to other vendors and monitor whether appropriate contracts and controls may be in place.

A contingency plan may be in place for responding to emergencies. Covered entities may be responsible for backing up their data and having disaster recovery procedures in place. The plan may document data priority and failure analysis, testing activities, and change control procedures.

Internal audits play a key role in HIPAA compliance by reviewing operations with the goal of identifying potential security violations. Policies and procedures may specifically document the scope, frequency, and procedures of audits. Audits may be both routine and event-based.

Procedures may document instructions for addressing and responding to security breaches that may be identified either during the audit or the normal course of operations.

Physical Safeguards—controlling physical access to protect against inappropriate access to protected data Controls may govern the introduction and removal of hardware and software from the network. (When equipment may be retired it may be disposed of properly to ensure that PHI may be not compromised.)

Access to equipment containing health information may be carefully controlled and monitored.

Access to hardware and software may be limited to properly authorized individuals.

Required access controls consist of facility security plans, maintenance records, and visitor sign-in and escorts.

Policies may be required to address proper workstation use. Workstations may be removed from high traffic areas and monitor screens may not be in direct view of the public.

If the covered entities utilize contractors or agents, they too may be fully trained on their physical access responsibilities.

Technical Safeguards—controlling access to computer systems and enabling covered entities to protect communications containing PHI transmitted electronically over open networks from being intercepted by anyone other than the intended recipient.

Information systems housing PHI may be protected from intrusion. When information flows over open networks, some form of encryption may be utilized. If closed systems/networks may be utilized, existing access controls may be considered sufficient and encryption may be optional.

Each covered entity may be responsible for ensuring that the data within its systems has not been changed or erased in an unauthorized manner.

Data corroboration, including the use of check sum, double-keying, message authentication, and digital signature may be used to ensure data integrity.

Covered entities may also authenticate entities with which they communicate. Authentication consists of corroborating that an entity may be who it claims to be. Examples of corroboration include password systems, two or three-way handshakes, telephone callback, and token systems.

Covered entities may make documentation of their HIPAA practices available to the government to determine compliance.

In addition to policies and procedures and access records, information technology documentation may also include a written record of all configuration settings on the components of the network because these components may be complex, configurable, and always changing.

Documented risk analysis and risk management programs may be required. Covered entities may carefully consider the risks of their operations as they implement systems to comply with the act. (The requirement of risk analysis and risk management implies that the act's security requirements may be a minimum standard and places responsibility on covered entities to take all reasonable precautions necessary to prevent PHI from being used for non-health purposes.)

System Processes Description—Exemplary Embodiments

A Submit New Referral Process may be created to describe how the new referral may be created for a Patient, when they visited their Primary Care Provider (PCP) and needed a Specialist. See FIG. 1.

Activity Description

A Submit New Referral Process may begin when a Patient visits his Primary Care Provider (PCP), and the PCP decides that a Referral may be needed for the Patient.

In order to create a new Referral, the PCP enters the Patient's information, including Insurance and Insurance Provider information, so that Specialists within the Insurance Provider's network may be narrowed and listed.

Based on the Insurance provider defined for the Patient and the selected Specialty for the Referral, the list of Specialists will be filtered, and the listed Specialists will be within the Patient's insurance coverage. If no specialist is located under the Patient's insurance, the requesting office places the referral in a holding status until the physician approves an alternative specialist for the patient in order to complete the referral request. The system will identify that no specialists are currently loaded that meet the requirement for a particular patient's insurance. The PCP requests the Provider to choose a Specialist for the referral if a physician is not already loaded within the software.

After a Specialist is selected, the PCP enters the details of the Referral, including Referral Type and special instructions/patient history if applicable.

If this is an existing Patient, the patient information may be already in profile, which may also be updated, including the Patient's billing information—either to be paid by Insurance or by patient; if this is a new Patient, a new Patient profile may be added and saved.

At this point, the Referral may be signed and created; new Referral notifications may be sent to a Referral Coordinator Manager.

After one Referral is created for the Patient, the system may allow the PCP to create more Referrals for the same Patient by redirecting back to "Choose Specialty".

Inputs for the Submit New Referral Process may include:
The Patient's Insurance information
The pre-defined Specialties list
Insurance Provider's network coverage information for Specialists
The Specialist's detailed information, such as Locations
The Patient's detailed information, which may either be entered for new Patient or selected from existing Patient profiles
The Patient's billing information, which may either be Insurance pay or self-pay Outputs for the Submit New Referral Process may include the newly created Referral record(s) with unique tracking identifier code(s), and notifications sent to a Referral Coordinator Manager, which may then assign the new created Referral during the Coordinate Referral Process.

Roles & Responsibilities involved in this process may include the following:
Patient, who goes to PCP for unknown medical reason
Primary Care Provider (PCP), who decides that a referral may be needed for the Patient and submits the Referral request in the system
Referral Coordinator Manager, which may receive notifications for new Referral

TABLE 1

Exemplary System Rules Description

There may be two types of Networks:
  Healthcare System Network: this may be used to track
  whether the Specialist may be In- or Out-of- the Healthcare System's
  network
  Insurance Network: this may be used to identify a Specialist
  that may be In- or Out-of- Patient's Insurance network
PCP (Primary Care Provider) may be associated with only one Hospital
(at a specific address), or none as individual PCP.
Specialist may be In- or Out- the selected Healthcare System's network.
Patient may see PCP first to get referral to Specialist.
Each Patient may be attached with one PCP, only that PCP has access to this Patient's data.
Patient may be referred to more than one Specialist at one time.
Each Referral may have a unique Referral ID, even when multiple Referrals are created for one Patient at one time.
Specialist may be selected based on Patient's insurance coverage.

TABLE 2

Exemplary Process Requirements Description

Healthcare System and Hospital may be added as a client account, with Healthcare System Admin User created and assigned.
PCP may be attached to only one Hospital.
PCP office staff may be able to submit Referral on behalf of the selected PCP.

TABLE 2-continued

Exemplary Process Requirements Description

PCP office staff may be associated with location, and be able to submit Referral for PCP(s) in the same location.
Specialist may be affiliated with at least one Healthcare System.
Patient profiles may be added under PCP, and PCP users only have access to Patients attached to them.
Patient's insurance information to be collected.
Patient's insurance information may be used to narrow down Specialists that may be within Patient's insurance network.
Specialty may be defined.
Selection of Specialist may depend on defined Insurance and Specialty.
PCP may be able to indicate whether the Specialist may be with In- or Out-of- the network of the PCP's Hospital.
Report may be generated to show referred Specialists and Hospital network information.
New Specialist may be added.
Patient's preferred language may be specified.
Patient's Diagnosis information may be defined for a Referral record.
Patient's billing information may be specified.
Special instruction may be added for new Referral.
Multiple Referral records may be added for one Patient at once.
Notifications may be sent to Referral Coordinator Manager when a new Referral is created.

Figure 2:
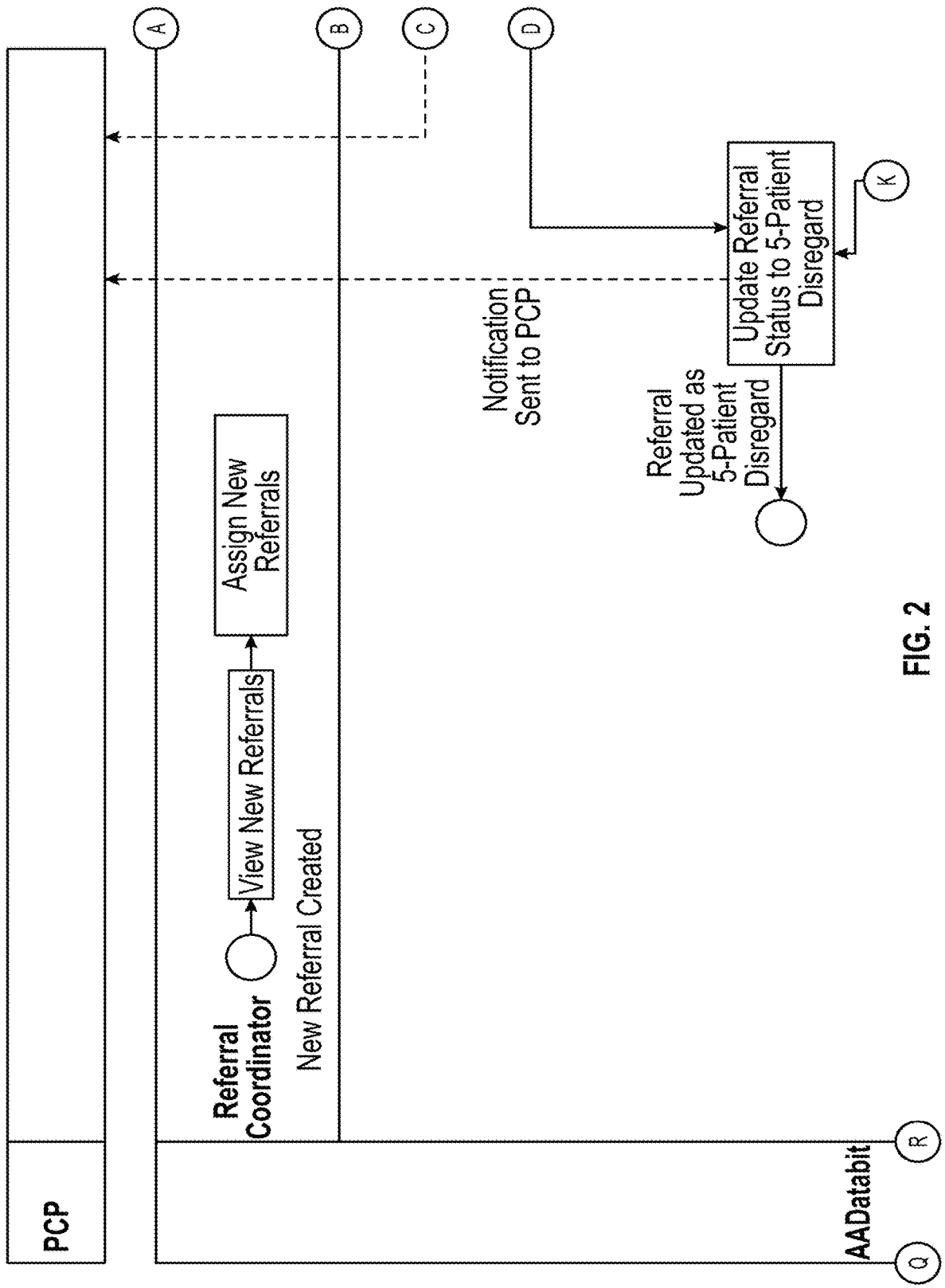
FIG. 2 is a workflow diagram depicting a Coordinate Referral Process of an exemplary embodiment.
Figure 2:
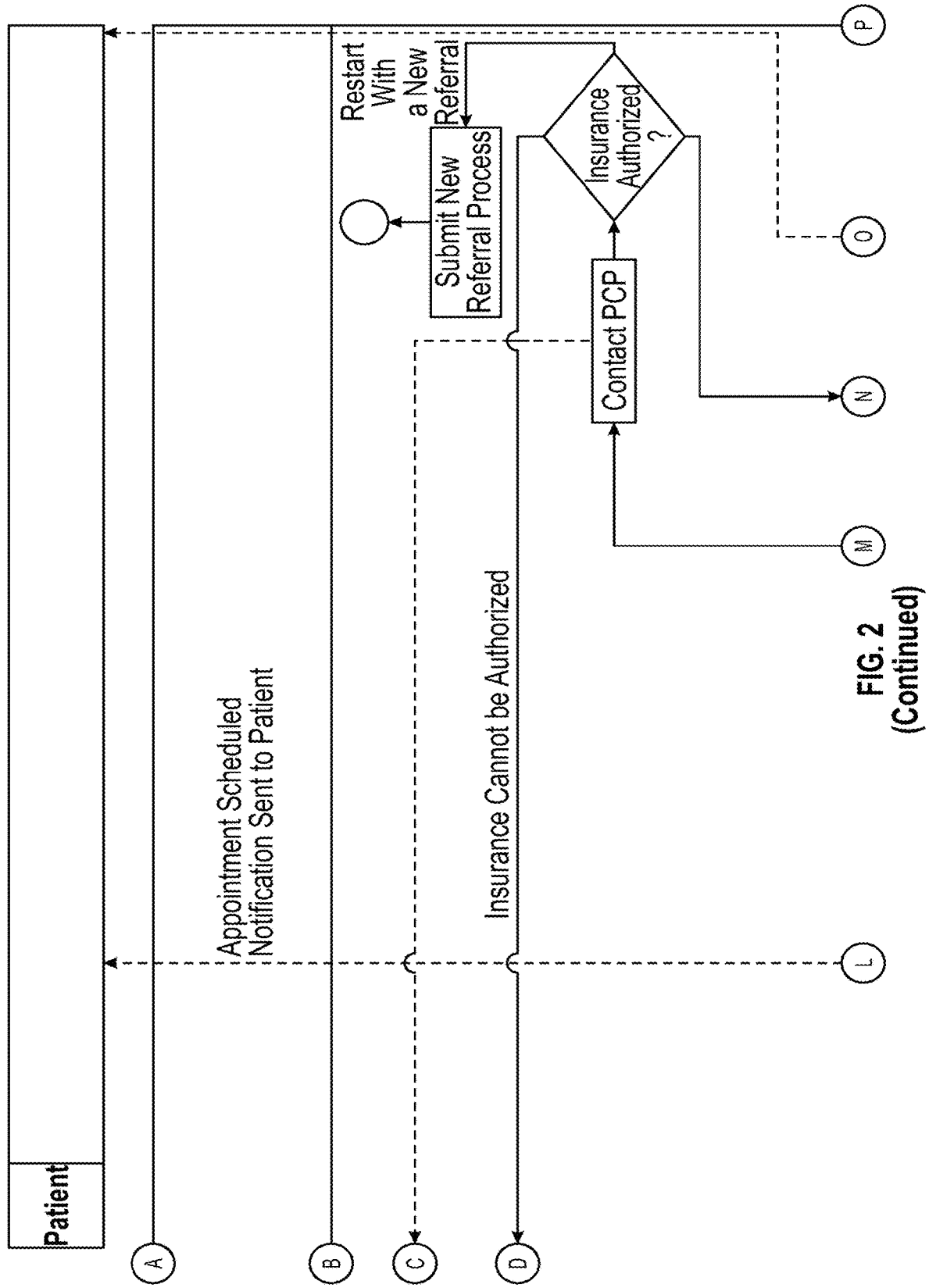
Figure 2:
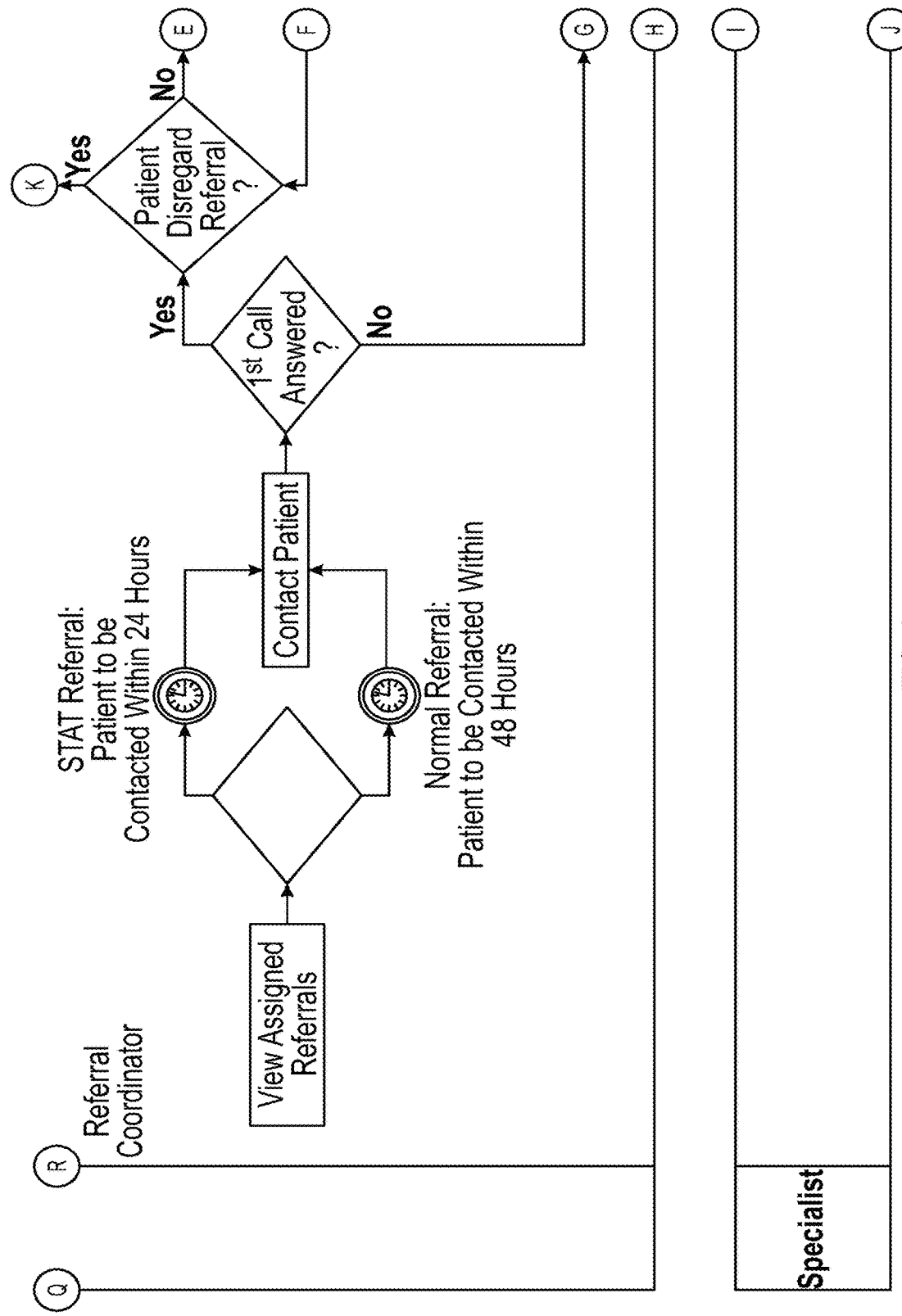
Figure 2:
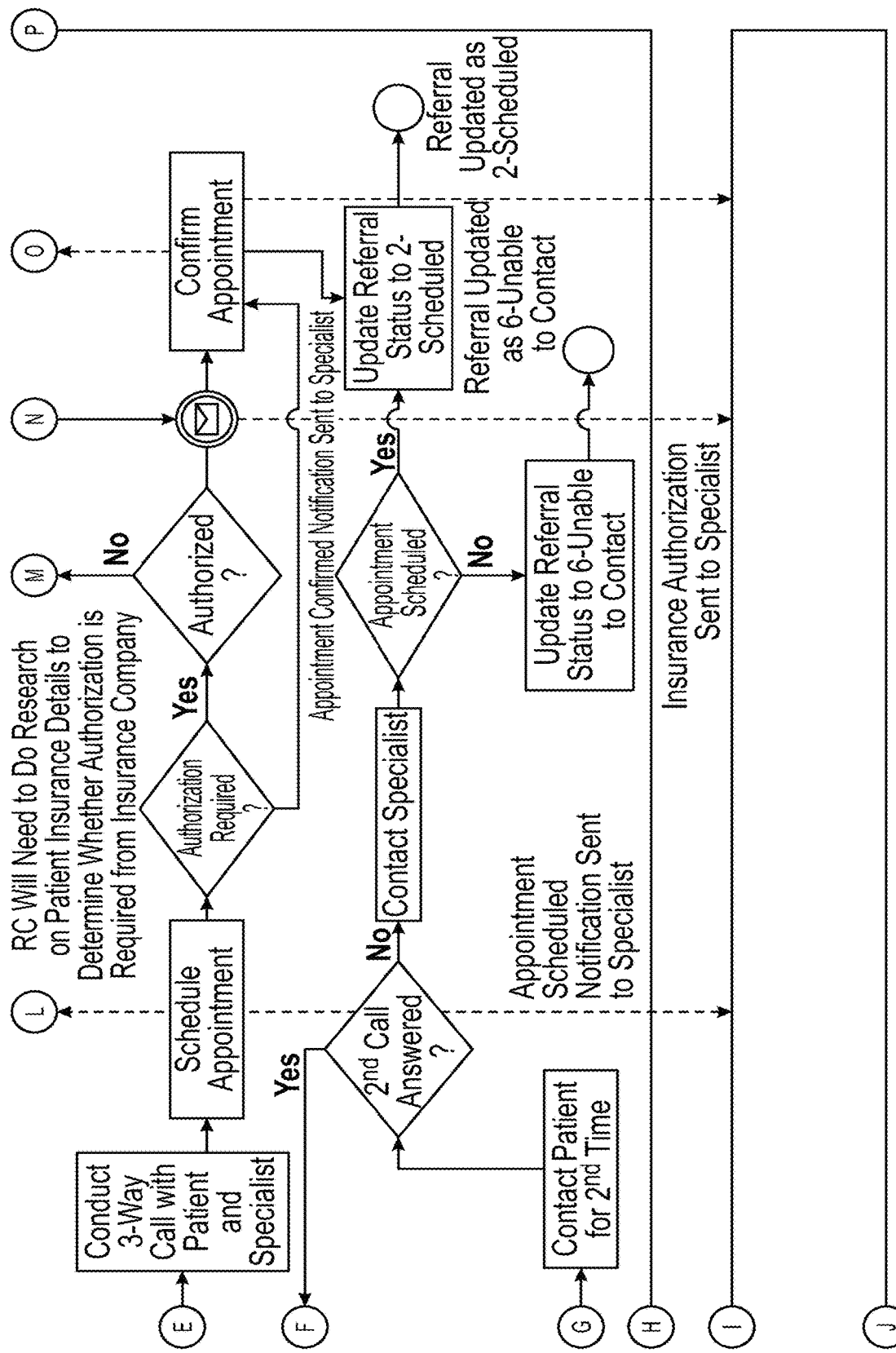

An exemplary Coordinate Referral Process may be triggered when the new Referral is created after a Submit New Referral Process, and enables a Referral Coordinator to helps a Patient and Specialist to schedule an appointment. See FIG. 2.

The Coordinate Referral Process may be triggered when a new Referral is created after a Submit New Referral Process, which may send a notification to a Referral Coordinator Manager.

Upon receiving new Referral creation notifications, a Referral Coordinator Manager may assign each new Referral created to a Referral Coordinator.

Once a new referral is assigned, the Referral Coordinator may contact the individual Patient based on Referral Type:
  I. Normal Referral: Patient to be contacted within 48 hours of submission.
  II. STAT Referral: Patient to be contacted within 24 hours of submission.

If the Patient is contacted by the system, the Patient may disregard the Referral, in which case a Referral status on the system may be changed to "5—Patient Disregard", and the system may send a notification to the PCP office automatically by end of day; otherwise, when the appointment has been scheduled, notifications may be sent to the Patient and the Specialist, and the scheduled date may be added to the Patient's calendar.

Once the appointment is scheduled: if no authorization is required, the appointment may be confirmed directly; otherwise, if authorization is required, the appointment may only be confirmed after the authorization may be generated from the Insurance company. Once the appointment may be scheduled and confirmed, the Referral status may be changed to "2—Scheduled" with sub status as "Confirmed". When the appointment has been confirmed, notifications may be sent to the Patient and the Specialist.

In case authorization is required but denied by the Insurance company, the system may contact the PCP, which may result in the following three scenarios:
  I. Insurance authorization generated—this may lead to the appointment confirmation.
  II. Insurance not authorized—in this case, the Referral status may be changed to "5—Patient Disregard" and the system may send a notification to the PCP office automatically.
  III. A new Referral may be needed, with another Specialist selected, which may trigger a Submit New Referral Process.

If the 1$^{st}$ call is NOT picked up by the Patient, the Referral Coordinator or system may call the Patient for a 2nd time; if the 2nd call is picked up, the system may perform the same steps when the 1$^{st}$ call is picked up, otherwise, the system may contact the Specialist to find out more details. If after the second attempt there is no patient contact; the system will notify the patient via a text message and then notify the PC if no contact with patient was possible.

If the Referral Coordinator/system determines that the appointment has already been scheduled, the Referral status may be changed to "2—Scheduled". Otherwise, the Referral status may be changed to "6—Unable to Contact".

Inputs for a Coordinate Referral Process may include:
The newly created Referral request
Insurance company and Insurance plan policy
Outputs for the Coordinate Referral Process may include:
Updated Referral status
Notifications when Referral status gets updated
Roles & Responsibilities involved in this process may include the following:
  Referral Coordinator Manager, whose responsibility may be to assign the new created Referrals to Referral Coordinators.
  Referral Coordinator, whose responsibility may be to contact Patients, and coordinate among Patients, Specialists, and PCPs to schedule a Referral appointment.

TABLE 3

Process Rules Description

Referral needs to be assigned first then be worked on.
There may be two types of Referral:
  Normal Referral: Patient may be contacted within 48 hours of submission.
  STAT Referral: Patient may be contacted within 24 hours of submission.
Depends on Insurance provider and Insurance plan, some Referral Appointment requires Insurance provider's authorization.

TABLE 4

System Requirement Description

Referral Coordinator Manager may assign new Referral to Referral Coordinator.
Notifications may be sent to a Referral Coordinator when new Referral may be assigned.
When Referral Coordinator contacts Patient for appointment, if the 1st call was not answered, call needs to be made in 2 days.
Referral Coordinator may conduct 3-way call between Patient and Specialist to schedule the appointment; and once appointment scheduled, notifications may be sent to both the Patient and the Specialist.
Notifications may be sent via Text message if cell phone may be provided, or Email if email address may be provided.
Appointment schedule notifications may be added to Patient or Specialist's calendar.
Reminders may be sent [X] days (configurable) before the scheduled date.
Appointment may be confirmed, and notifications may be sent to both Patient and Specialist when confirmed.
When Referral may be scheduled, the Referral status may be automatically changed to "2 - Scheduled".
When Referral is confirmed, the Referral sub status may be automatically changed to "Confirmed".
For Referral requires Insurance Authorization, system may automatically update sub status to "Confirmed" only after Authorization document uploaded.

TABLE 4-continued

System Requirement Description

Once Referral is Scheduled and Confirmed, the full Referral script may be auto faxed to Specialist.
Referral status may be updated to "5 - Patient Disregard" when the Patient disregards the call and referral.
Referral status may be updated to "6 - Unable to Contact" when the Patient is not contacted for the referral.
Daily report may be sent to PCP office by end of day, when the Referral status is changed to "5 - Patient Disregard" and "6 - Unable to Contact".

Figure 3:
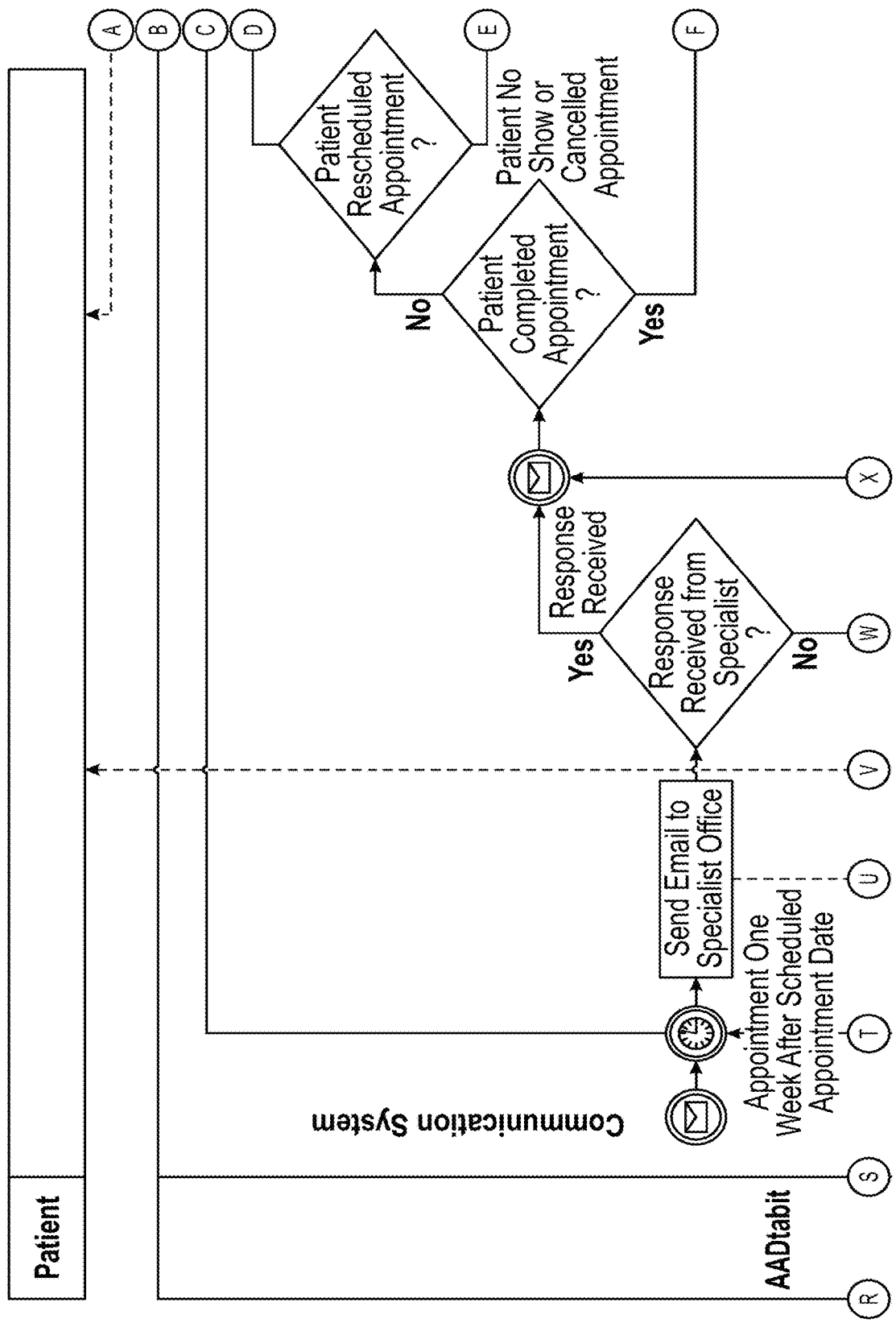
FIG. 3 is a workflow diagram depicting a Follow-Up Referral Appointment Process of an exemplary embodiment.
Figure 3:
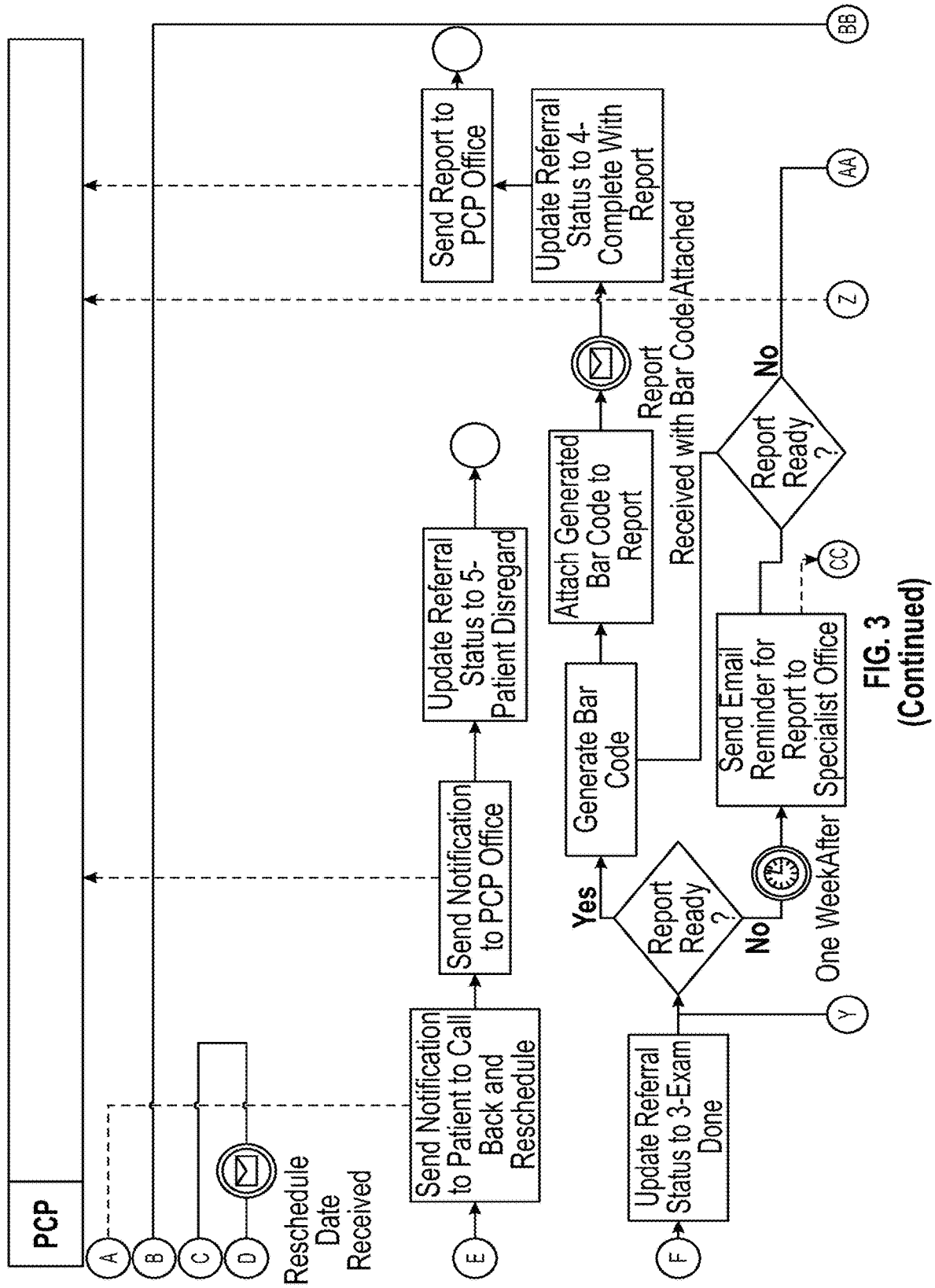
Figure 3:
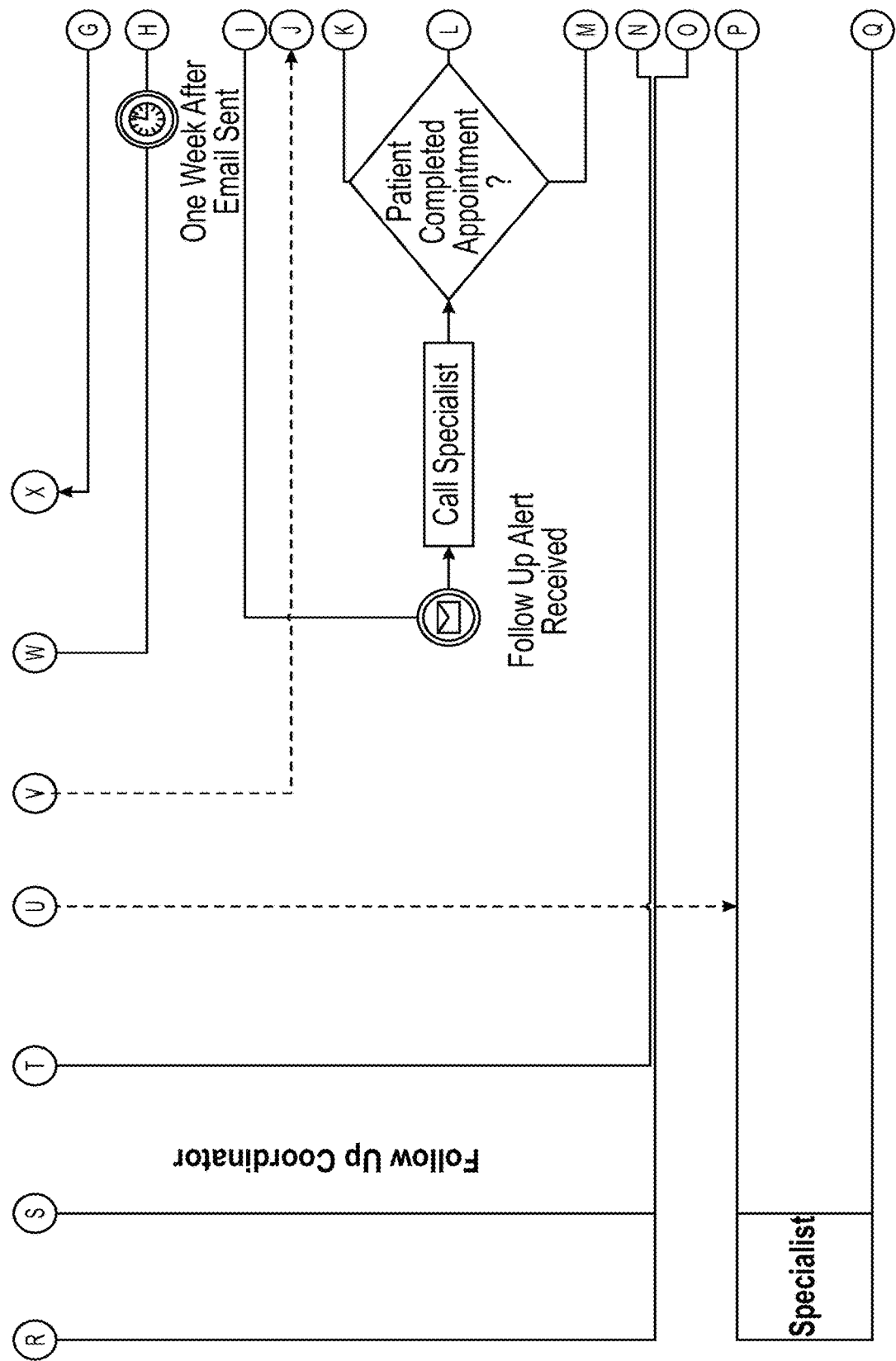
Figure 3:
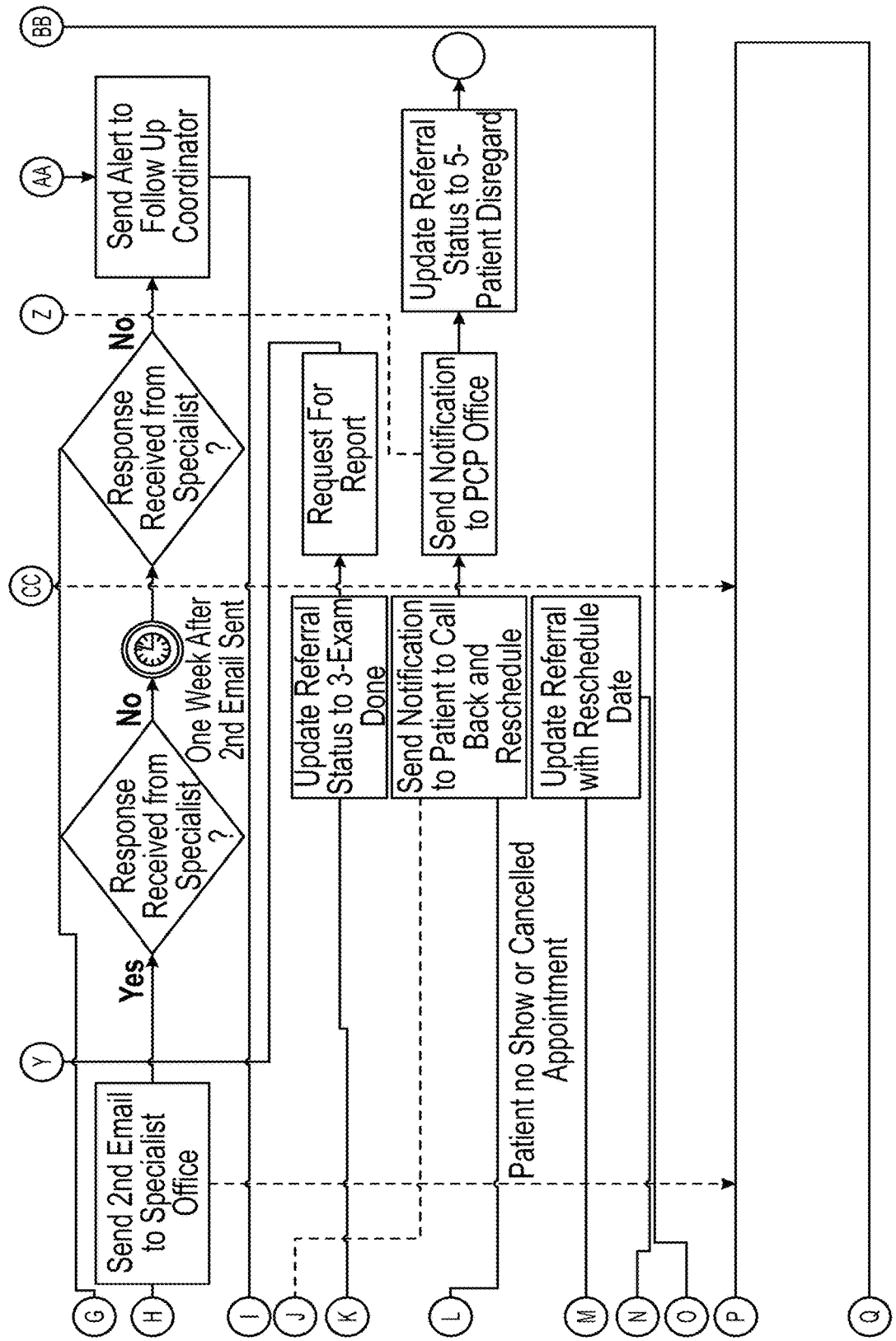

A Follow Up Referral Appointment Process may begin after the Referral is scheduled, and the system may send follow up emails to get a Report and then complete the Referral. See FIG. 3.

A Follow Up Referral Appointment Process may be triggered when an Appointment is scheduled. One week after the scheduled date, the system may send an email to the Specialist Office to follow up, including a link, clicking which may present the following emailed questions which may be used to query the Specialist to answer and submit:

I. Has Patient Completed the Appointment?—Yes or No
  i. If "Yes", go to question II
  ii. If "No", select from the following conditions:
    a. Patient has rescheduled Appointment—if selected, reschedule date needs to be entered
    b. Patient was No Show
    c. Patient Canceled Appointment
II. Is the Report Ready?—Yes or No If the Patient has completed the Appointment and the Report is ready, the system may generate a unique bar code and send it to the Specialist office, which may then attach the bar code to the Report and send the Report to the system. Upon receiving the Report, the system may read the unique bar code and attach the Report to the corresponding Referral, as well as sent the Report to the PCP Office automatically, with Referral status changed to "4—Complete with Report".

If the Patient has completed the Appointment but the Report is NOT ready, system may send a Reminder notification one week after asking for the Report. If the Report is still not received by that time, system may send an alert to a Follow Up Coordinator, who may then contact the Specialist to find out more details.

If the Patient has NOT completed the Appointment, and:
a. Patient has rescheduled Appointment: The Specialist may report the reschedule date, which may restart the process and trigger a follow up Email one week after the rescheduled date.
b. Patient was No Show: System may send notifications to Patient to reschedule the Referral with the system, and the system may also send notifications to the PCP office, with Referral status changed to "5—Patient Disregard" with "No Show" noted.
c. Patient Cancelled Appointment: System may send notifications to Patient to reschedule the Referral with the system, and the system may also send notifications to the PCP office, with Referral status changed to "5—Patient Disregard" with "Cancellation" noted.
d. Patient has NOT rescheduled Appointment: System may send notifications to Patient to reschedule the Referral with the system, and the system may also send notifications to the PCP office, with Referral status changed to "5—Patient Disregard".

On the other hand, if NO response is received from the 1$^{st}$ follow up Email, the system may send 2 more Emails every week for 2 weeks. If a response is received from any of the emails, the process goes back to the Response received step, otherwise, if there is still no response received after the 3 Emails, the system may send an alert to a Follow Up Coordinator, who may call the Specialist to find out more details.

If the Follow Up Coordinator learns from the Patient that the Patient has already completed the Appointment, the Referral status may be changed to "3—Exam Done", and the Follow Up Coordinator may send the system generated bar code to the Specialist, who may then send the Report with bar code attached. Afterwards, the system may send the received Report with bar code to the PCP Office automatically, with Referral status changed to "4—Complete with Report" Similarly, if the Patient has NOT completed the Appointment, the (a)-(d) scenarios described above may be applied.

The bar code may be generated by the system, using the "Universal Product Code" format and in A VERY 8366™ size.

Inputs for the Follow Up Referral Appointment Process may include scheduled Referral Appointment information and response information received via Email from a Specialist.

Outputs for a Follow Up Referral Appointment Process may include updated Referral records and notifications sent to Patient and PCP.

Most of the activities in this process may be automatically done by the system, and the Role included may be the Follow Up Coordinator, whose responsibility may be to contact the Specialist to find out more details about the Appointment when an alert has been received.

TABLE 5

System Rules Description

Follow up Email may be sent automatically with options/link for Specialist to respond with feedback.
Follow up Fax may be sent automatically for Specialist to fill in feedback and fax back.
Follow Up Coordinator may contact Specialist to find out more details when the auto Email receives no feedback.

TABLE 6

System Requirements Description

One week after the scheduled date, follow up Emails may be sent to Specialists asking the following questions with options/link to send the feedback back:
  Has Patient Completed the Appointment? - Yes or No
    If "Yes", go to the next question
    If "No", select from the following conditions:
      Patient has rescheduled Appointment -
      if selected, reschedule date needs to be entered
      Patient was No Show
      Patient cancelled Appointment
  Is the Report Ready? - Yes or No
Referral status may be updated based on answers received via a follow up link sent in the follow up Emails.
Reschedule date may be updated to the Referral, if received.
If Patient was No Show for the appointment, the Referral status may be updated to "5 - Patient Disregard" with sub-status as "No Show".
If Patient cancelled the appointment, the Referral status may be updated to "5 - Patient Disregard" with sub-status as "Cancellation".
Notifications may be sent to Patient and PCP if Patient was No Show or Cancelled the appointment.
If the 1$^{st}$ Email was not answered, 2 more emails may be sent every week after.

TABLE 6-continued

System Requirements Description

If 'Has Patient Completed the Appointment? = Yes' and 'Is Report Ready? = Yes', system may send (e.g., via email or fax) the generated unique bar code to Specialist, who may then attach the bar code to Report and send it back to System.
Report with bar code may be faxed back, and system may be able to read bar code and attach received Report to corresponding Referral record automatically.
After the Report is received from Specialist, the Referral status may be updated to "4 - Complete with Report" automatically. Unique bar code may be generated and attached to the report, and sent to After the Report is received from Specialist, the Report without bar code attached may be faxed and/or emailed to the PCP office.
If Report is NOT received, Reminder notification may be automatically sent to Specialist one week after the 1$^{st}$ follow up notification.
Alert may be sent to Follow Up Coordinator if no response received after 3 follow up Emails, or no report received after 1 reminder.

Figure 4:
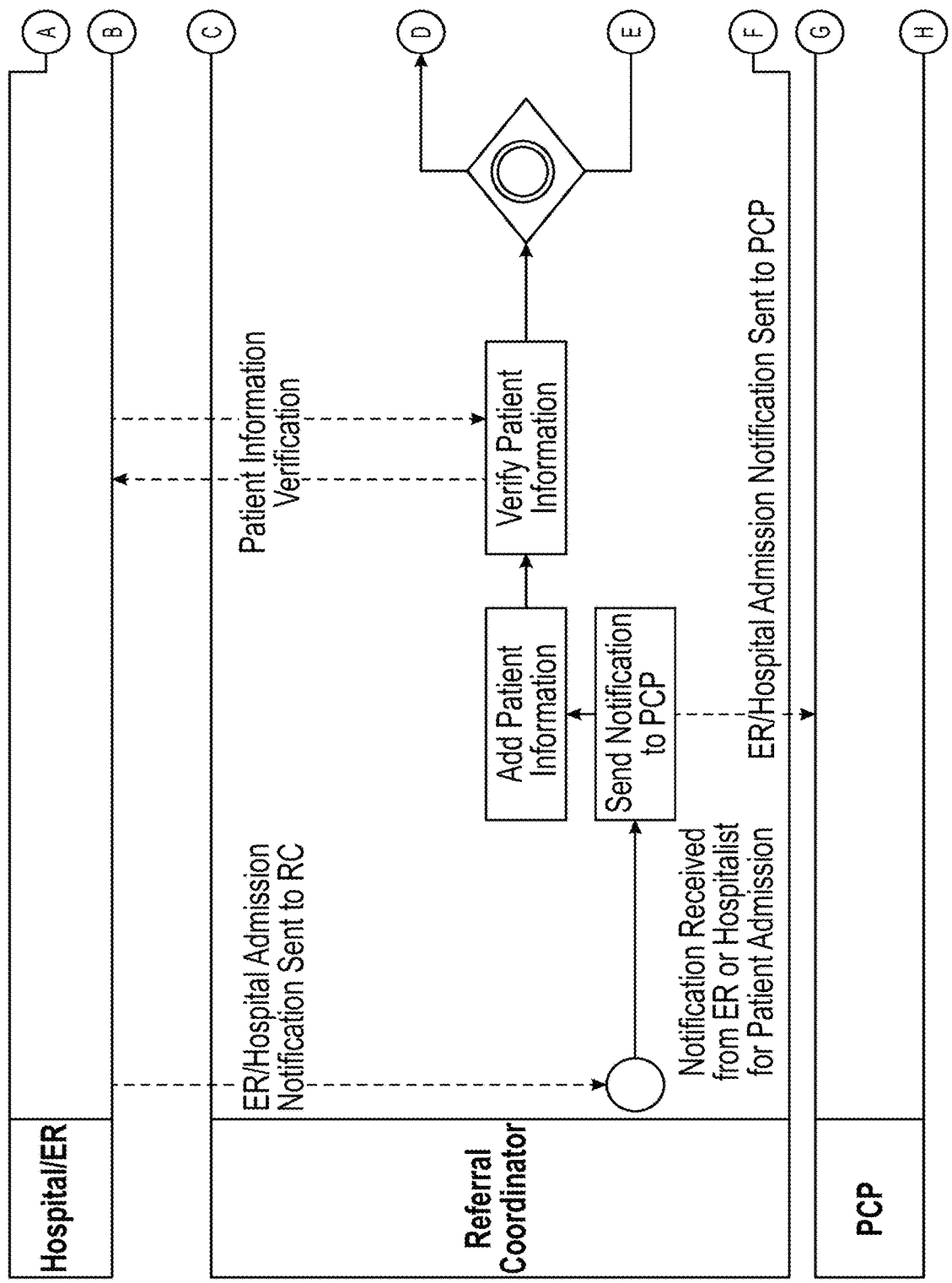
FIG. 4 is a workflow diagram depicting an Emergency Room and Hospital Admission Referral Process of an exemplary embodiment.
Figure 4:
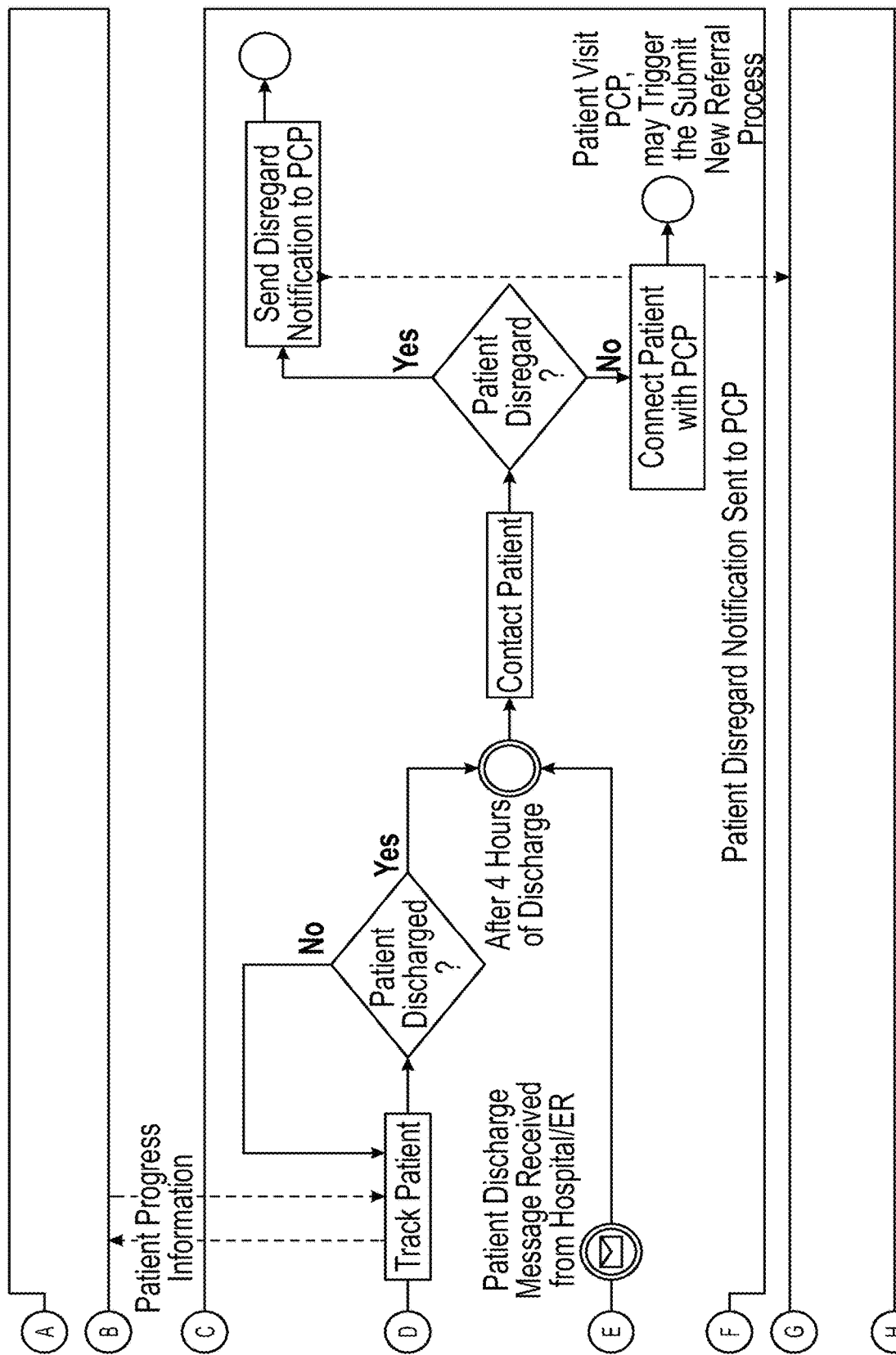

An ER and Hospital Admission Referral Process may be triggered when notifications received from a Hospital/ER for a Patient's admission. Referral Coordinators may then keep track of the Patient's progress and contact the Patient for Referral after discharge. See FIG. 4.

When the Patient arrives to an ER, staff may ask for his PCP's information, and notifications may be sent to the PCP and the system from a hospital secure email server to an associated secure email recipient (PCP and System) for this new admission. It's also possible that the Patient is admitted at ER and then transferred and admitted to a Hospital as a normal admission. When the Patient arrives at the Hospital as a normal admission, the Patient may be added to a Hospital list, and notifications may be sent to the System for this new admission.

An ER and Hospital Admission Referral Process may be triggered when notifications received from a Hospital/ER for a Patient's admission. A Referral Coordinator may then send notifications to the Patient's PCP and add the new admission record for the Patient if the Patient already exists in the system, or if a new Patient to the system, add the new Patient's profile with the new admission record.

The Referral Coordinator may also verify the Patient's information by logging into a secure hospital Citrix portal, as well as keep track of the Patient's progress and discharge status daily. When either discharge notification may be received or discharge status changed with daily check-in, the system may contact the Patient 48 hours after his discharge.

When contacting the Patient, the system may either connect the Patient with the PCP office for further scheduling, or send a Disregard notification to the PCP if the Patient disregards the referral.

Inputs for the ER and Hospital Admission Process may include:
 Admission notifications from Hospital and/or ER
 Verified patient information from Hospital
 Patient progress information from Hospital and/or ER
 Patient discharge notification from ER Outputs for the ER and Hospital Admission Process may include notifications sent to PCPs.

A Role involved in this process may be the Referral Coordinator/system, whose responsibility may be to keep track of the Patient's discharge status and contact the Patient for referral.

TABLE 7

System Rules Description

When Patient is admitted to an ER, the ER may ask for his PCP information, and ER admission notifications may be sent to the PCP and System.
When Patient is admitted to a Hospital, the Hospital may add the Patient to a Hospital list of Patient Admission, and send to System.
When Patient is admitted to ER or Hospital, notifications may be sent to the Patient's PCP office automatically.
System staff may login to a Citrix portal to verify the Patients' information.
System staff may track the Patient's progress and discharge status by communicating with the Hospital.
48 hours after Patient's discharge, System may contact Patient.

TABLE 8

System Requirement Description

Notifications may be received from ER/Hospital for Patient Admission, with date/time captured.
System may send notifications to PCP office, through fax or email, when Patient Admission notification is received from ER/Hospital.
Patient Admission Record may be created and attached to Patient profile.
Patient information may be verified by logging into Citrix portal.
Patient discharge notification may be received.
Patient discharge date/time may be captured.
System may send notifications to PCP office (e.g., through fax or email) when Patient disregards System's follow up request.

System Description and Functional Requirements
User Management

Both Client users, including Primary Care Provider and Client Admin, and System Staff users may have direct access to the system. The following users may be created and granted with access to the system:

Client Side:
Healthcare System Admin User, who has access to all data within the network, including all the Hospitals; may be created by System Admin User.
Hospital Admin User, who has access to all data within the Hospital; may be created by System Admin User.
Primary Care Provider (PCP) User, who may be associated with or without Hospital(s), and have access to data of Patients under him, therefore submit the new Referral record; PCP may be able to self-register with temporary login provided by System:
  I. System Admin User may create temporary Login (username and password) for PCP who uses the system.
  II. PCP User logs in with the temporary credential and completes the registration information, including signing HIPAA and BAA agreements.
  III. PCP completes the self-registration and obtains the valid credential for the system as an official user.
PCP Office Staff User, who preferably may only submit and check Referrals for PCPs in the same office; may be created by PCP User or System Admin User.
System Side:
Admin User, who has access to all system data and admin permissions
Referral Coordinator Manager, who has access to data of assigned Healthcare System and Hospital(s), and may generate reports for assigned network and coordinators that work underneath assigned network
Referral Coordinator, who coordinates between Patient and Specialist, for appointment scheduling, referral tracking and follow ups, and has access to data of assigned Hospital Network and Hospital(s)

Follow Up Coordinator, who may be responsible for Referral follow ups, and have access to data of assigned Hospital Network and Hospital(s)

Users may be defined as people who interact with the system in various capacities (roles) to perform respective operations in the system.

Roles may be defined as different operations that may be required to interact with the system in various capacities to perform respective operations in the system. A user preferably may use the system with a defined role only.

There may be two types of user: Client User and System Staff User. For each user type, different User Roles may be defined and assigned.

For each User added in the system, a User Account and Login may be created, so that the User may be able to login to the system, access authorized data and functions, and manage his own account information.

TABLE 9

| Functional Requirement Description |
| --- |
| System may require User Type - Client User or Staff User, to be defined when creating new User. |
| System may require User Role to be defined for each User Type when creating new User: |
|    Client User Type: |
|       Healthcare System Admin |
|       Hospital Admin |
|       PCP |
|       PCP Office Staff |
|    Staff User Type: |
|       Staff Admin |
|       Referral Coordinator Manager |
|       Referral Coordinator |
|       Follow Up Coordinator |
| System may allow list of Users to be searchable, based on logged in User's access. For example, Healthcare System Admin User may search and view Users within the network, Hospital Admin User may search and view Users within the same Hospital, System Staff User may search and view all Users in the system. |
| System may allow User details to be viewed. |
| One Client User can only be associated with one Role. |
| One Staff User may be associated with more than one Role. |
| System may display different required information fields depending on different User Type and Role. For example, Healthcare System Admin User may be associated with Healthcare System, PCP Office Staff User may be associated with PCP Office location, etc. |
| System may allow authorized user to add/view/update Role. |
| A valid and unique Role name may be required. |
| Every Role may be associated with permission matrix. |
| Permission matrix may be pre-defined, consisting of process and actions. |
| System may allow permission matrix to be configurable as per requirement. |
| Permission matrix associated with Role may be unique. |
| Available Dashlets may be pre-defined for each Role. |
| System may allow Role to be activated and deactivated. |
| System may allow authorized user to search Roles. |
| When creating new User, System Admin needs to first select User Type (Client User, or Staff User) and User Role. |
| If User Type = Client User, only one Role can be assigned to the User; otherwise if User Type = Staff User, multiple Roles can be assigned to the User. |
| Fields to be filled to create new User may be different; depends on the entry of User Type and User Role. |
| When creating new User, System Admin may set up Username and Password. |
| If Email is provided, it can be checked to be used as Username, but not mandatory. |
| Email may be required for Staff User, but not for Client User. |
| If provided, Email address needs to be in valid format and unique. |
| If Email is provided, System may send verification email to User's provided email address, with Username and ask Password information, so that User can login and reset Password. |

TABLE 9-continued

| Functional Requirement Description |
| --- |
| For first time log in, User may be required to reset the Password. Password needs to be validated against standard requirements, min characters, mixed case, mixed characters/numbers. |
| All authorized user may login to the system with valid credentials |
| System may allow user to login with Email or Username and Password. |
| System may record both successful and failed login attempts of User, with an audit log. |
| Account may be locked after three login failure attempts. |
| User may need to contact System Admin if account locked. |
| User may be able to click "Forgot Password", and system will ask user to enter Username: |
|    1) Valid Username/Email entered: |
|       a. Valid Email: system will send a Reset Password email to the valid registered Email |
|       b. Valid Username: system will ask user to provide an Email address to send the Reset Password email; and User can choose to enter an Email or contact the System Admin |
|    2) Invalid Username/Email entered: since the entered Username/Email is not valid, error message will be displayed; or user needs to contact the System Admin for password reset |
| Logged in user may only access data that may be authorized for that user, based on account settings (user type, user role, associated entities, etc.) |
| System may provide HIPAA secure logins with SSL certificate. |
| System may allow user to reset password after logging in. |
| By a user clicking the reset password link, system may send reset password link to user's email address. |
| The new password may not be the same as old password, and may also be validated against standard requirements. |
| User may be able to update own information after being logged in. |
| System may send verification emails to previous and new email addresses, if user choose to change email address. |
| New email address may be valid only after user verification, and old email address may be invalid for login. |
| System may automatically log Users out (time out) after [X] period of inactivity. |
| User may be able to click "Sign Out" to manually sign out. |
| System may record all the Sign In and Sign Out activities of User, including: |
|    User's IP address |
|    Sign In Time |
|    Sign Out Time |
|    Signed in duration |

A Healthcare System, including one or many Hospitals, may be considered as the System's client; so that each Healthcare system may have one record created in the system, with one or more Hospitals attached.

For each Healthcare System record, there may be Healthcare Admin User who has access to all the data within the network, including all the Hospitals attached. Under each Healthcare System, there may be one or multiple Hospitals, and for each Hospital, there may be a Hospital Admin User who has access to all the data within that Hospital. A PCP may be associated with one or multiple Hospitals.

One PCP may have multiple offices, and sometimes office staff submit Referrals on behalf of the PCP; so each PCP may be associated with one or multiple office locations. For each office, an Office Staff User may be created to only have access to Referrals under the same office.

TABLE 10

| Functional Requirements Description |
| --- |
| System may allow Healthcare System record to be created and saved. |
| System may allow Healthcare System Admin User to be created and assigned to Healthcare System. |
| Healthcare System Admin User may login to the system and have access to all data under the assigned network, including: |

TABLE 10-continued

Functional Requirements Description

Hospital records
   PCPs accounts
     PCP Offices
      Patients information
   Referral records
   ER/Hospital Admission records
   INN and OON lists
   Report
Healthcare System Admin User may add/view/update Hospitals information under its network.
Healthcare System Admin User may add/view/update Referral records under its network.
Healthcare System Admin User may add/view/update the In-Network Specialist list.
Healthcare System Admin User may generate and view reports with all data under its network.
System may allow Hospital to be created and saved.
Healthcare System Admin User may add new Hospital Admin User to Hospitals under its network.
System may allow Hospital Admin User to be created and assigned to Hospital.
Hospital Admin User may login and only have access to data under the assigned Hospital, including:
   PCPs accounts
     PCP Offices
      Patients information
   Referral records
   ER/Hospital Admission records
   Report
Hospital Admin User may add/view/update Referral records under the assigned Hospital(s).
Hospital Admin User may generate and view reports with all data under the assigned Hospital(s).
System may allow authorized System user to create temporary login (temporary username and password) for PCP, who may be maying to sign up and use the system.
The PCP temporary login may already be associated with Healthcare System/Hospital, or without as individual PCP.
System may allow a PCP to be associated with one or more Healthcare Systems/Hospitals, or none (as an individual PCP).
The temporary login may only be valid within 48 hours.
System may allow PCP to login with temporary login received from System.
System may require PCP to change the temporary username and password after logged in.
System may allow PCP to sign HIPAA and BAA agreements, during registration.
System may require PCP to complete all the required fields to complete the registration.
System may allow PCP to login with new credential, after registration.
Patient profiles may be added under PCP, and only associated PCP may add new Patient information underneath him.
PCP User may login and have access to data of Patients associated with.
PCP User may submit new Referral for Patient associated with.
PCP User may generate and view report for Referrals submitted by himself.
System may allow new Location to be added.
System may allow PCP User be associated with one or multiple Office Locations.
System may allow PCP User to create PCP Office Staff User, for associated Office Locations.
System may allow Office Staff User be created and assigned to Office Location.
Office Staff User may only be able to submit new Referral on behalf of PCP within the same Office Location.

On the System side, an Admin User may have access to all data in the system and be granted with all permissions, including user account management, referral management, ER/Hospital admission management, case management and reporting.

Besides Admin User, a Referral Coordinator Manager, Referral Coordinator and Follow Up Coordinator User may be created and assigned to client accounts—Healthcare System records and/or Hospital records; so that they only have access to data of assigned accounts.

TABLE 11

Functional Requirements Description

Staff Admin User may be a super user who may be granted with all system permissions.
Staff Admin User may access all data in the system, including data from all Healthcare Systems.
Staff Admin User may add/view/update new User to the system.
Staff Admin User may add/view/update Healthcare System record in the system.
Staff Admin User may add/view/update Hospital record in the system.
Staff Admin User may add/view/update PCP record in the system.
Staff Admin User may add/view/update Patient record in the system.
Staff Admin User may add/view/update Specialty in the system.
Staff Admin User may add/view/update Specialist in the system.
Staff Admin User may add/view/update Referral in the system.
Staff Admin User may add/view/update ER/Hospital Admission record in the system.
Staff Admin User may generate and view report with all system data.
Referral Coordinator Manager, Referral Coordinator and Follow Up Coordinator may be assigned to Healthcare System and/or Hospital.
Referral Coordinator Manager, Referral Coordinator and Follow Up Coordinator may only have access to data of assigned Healthcare System/Hospital.
System may send notifications to assigned Referral Coordinator Manager when new Referral submitted for the Hospital.
Referral Coordinator may only assign new Referrals to Referral Coordinator assigned to the same Hospital.
System may send referral follow up alert to Follow Up Coordinator assigned to the same Hospital.

After being logged in, a user may be landed in (displayed) a Dashboard page, which may be customized by each individual user with available dashlets based on the user's role.

TABLE 12

Functional Requirements Description

System may land user on the Dashboard page, after user is logged in.
System may allow user to view assigned pre-defined dashlets as per their role.
System may allow user to configure their Dashboard, with the following information:
   Available Pre-defined Dashlets
   Shown Dashlets
   Hidden Dashlets
   Left Column Dashlets
   Right Column Dashlets
System may allow user to configure the Dashboard page by clicking Show or Hide assigned dashlets.
System may allow user to configure the Dashboard page by drag and drop dashlets in "Left Column" and "Right Column" to add them to their dashboard display.
User may save their dashlet configuration and the same may be visible to them on their login.

A Healthcare System may be a network or group of hospitals that work together to coordinate and deliver a broad spectrum of services to their community. Under one Healthcare System, there may be one or many Hospitals associated.

For each Healthcare System, there may be one or more Healthcare System Admin User(s), who each have access to all the Hospitals under the system and may generate reports with those data.

Each Healthcare System may have its own In- and Out-of-(leakage) Network list, and PCPs and Specialists may be associated with Healthcare System(s).

TABLE 13

Functional Requirements Description

System may allow Healthcare System to be created and saved.
System may allow authorized user to search for Hospitals. For example, Healthcare System Admin User may be able to search for Hospitals within the same network, System Staff User may be able to search for all the Hospitals.
System may allow Healthcare System Admin User to be created and assigned to Healthcare System.
Healthcare System Admin User may have access to all data under the assigned network.
Healthcare System Admin User may generate reports with all data under the assigned network.
System may allow Hospital to be created and saved.
System may allow Hospital Admin User to be created and assigned to Hospital.
Hospital Admin User may have access to all data under the assigned Hospital.
Hospital Admin User may generate reports with all data under the assigned Hospital.
System may allow one or multiple Hospital(s) be associated with one Healthcare System.
System may allow System users, including Referral Coordinator Manager, Referral Coordinator and Follow Up Coordinator, to be assigned to Healthcare System.
System may allow System users, including Referral Coordinator Manager, Referral Coordinator and Follow Up Coordinator, to be assigned to Healthcare System.
System may allow PCP to be associated with Healthcare System and/or Hospital.
System may allow Specialist to be associated with Healthcare System and/or Hospital.
In- and Out-of (Leakage) Network list may be attached to Healthcare System.

A primary care provider (PCP) may be a health care practitioner who sees people that have common medical problems. Patients need to visit their PCP first, then may be referred to Specialists. A PCP may need to sign up with the System in order to use the Referral platform, by signing BAA and HIPAA agreements. Once the PCP has registered with the System, a unique login may be created for that PCP.

A PCP may be associated with a Healthcare System and/or a Hospital, or without any Healthcare System/Hospital (as an Individual PCP). For most cases, one PCP may be associated with one Hospital, but the system is sufficiently flexible to allow multiple Hospitals to be associated with one PCP.

Each PCP may have its own list of Patients, only for whom the PCP may have access to view/update patient information and submit Referrals.

Each PCP may have one or many different offices, each of which may be associated with that PCP. For each PCP office, there may be at least one PCP Office Staff User who may submit Referrals on behalf of that PCP.

TABLE 14

Functional Requirement Description

System may allow a PCP account to be created and saved.
System may allow authorized users to search for PCPs. For example, a Healthcare System Admin User may search for PCPs within the same network, a Hospital Admin User may search for PCPs within the same Hospital, and a System Admin User may search for all PCPs in the system.
System may allow a PCP to be only associated with one Hospital (at a specific address), and Healthcare System will be recognized based on selection of Hospital.

TABLE 14-continued

Functional Requirement Description

System may allow a PCP to be created without associating it with any Healthcare System/Hospital, as an Individual PCP.
System may allow multiple PCP Office Locations to be associated with PCP.
For each PCP Office, at least one PCP Office Staff may be defined.
For each PCP Office, Communication Preference may be defined.
For each PCP Office, Office Hours may be defined.
System may allow a PCP Office Staff User to be created and associated with Office location.
A PCP Office Staff User may only submit a Referral on behalf of a PCP within the same Location.
PCP may only submit a Referral for its own Patient.
PCP may be able to generate and view a report with data of its own Patient.
System may allow an authorized System user to create a temporary login (temporary username and password) for PCP using the system.
The PCP temporary login may already be associated with a Healthcare System/Hospital, or an individual PCP.
The temporary login may only be valid within 24 hours.
System may allow a PCP to login with a temporary login received from System.
System may require PCP to change the temporary username and password after being logged in.
System may allow PCP to sign HIPAA and BAA agreements, during registration.
System may allow PCP office locations to be added, during registration.
System may enforce PCP to fill all the required fields to complete the registration.
System may allow PCP to login with new credential, after registration.
Authorized Staff user may be able to review and approve PCP.
Only approved PCP may be able to log into the system.
Patient profiles may be added under PCP, and only associated PCP may be able to add new Patient information underneath him.

TABLE 15

Functional Requirement Description - Patient Management

System may allow a Patient profile to be created and saved.
Patient profile may only be added by PCP, but may be updated by System staff Users.
System may allow Patient profile to be updated and saved.
System may allow authorized user to search for Patients. For example, Healthcare System Admin User may search for Patients within the same network, Hospital Admin User may search for Patients within the same Hospital, PCP User may search for Patients associated with him, System Staff User may search for all Patients in the system.
Patient profile may be attached to one PCP.
Patient's preferred language may be added and updated.
Patient's insurance information, including insurance provider, insurance plan, etc. may be added and updated.
Patient's billing information may be defined: whether self-pay, or paid by insurance.
System may attach Referral and ER/Hospital Admission records to Patient profile.
For each Patient profile, system may allow the history of Referral records to be viewed.
For each Patient profile, system may allow the history of ER/Hospital Admission records to be viewed.

TABLE 16

Functional Requirement Description - Specialty Management

System may allow the list of Specialty to be pre-defined.
System may allow new Specialty to be added.
System may allow Specialty list to be updated.
System may allow authorized user to search for Specialty, such as System Staff Admin User.
System may allow Specialty to be selected from the pre-defined list when adding new Referral.

TABLE 16-continued

Functional Requirement Description - Specialty Management

System may allow Specialty to be associated with Specialist.
System may display Specialists who may be associated with selected Specialty, when adding new Referral.

TABLE 17

Functional Requirement Description - Specialist Management

System may allow a Specialist profile to be added and saved.
System may allow a Specialist profile to be updated and saved.
System may allow a Specialist profile to be added with Specialties.
System may allow Specialist to be associated with one or more than one Hospital.
System may allow Insurance and Insurance Plan information to be defined for each Specialist.
System may allow authorized user (System Admin User) to add or remove Specialists to or from INN list and ONN (Leakage) list, for selected Hospital.
System may allow Specialist profile to be associated with multiple Office Locations.
System may allow authorized user to search for Specialists.
System may allow Referral to be attached to Specialist profile.
System may allow authorized user to view the history of Referral records of selected Specialist.

TABLE 18

Functional Requirement Description - Location Management

System may allow Location to be added and saved.
System may allow Location to be updated and saved.
Operation hours may be defined for each Location.
System may allow authorized user to search for Locations.
System may allow Location to be associated with PCP and Specialist.
System may allow one Location to be associated with multiple PCPs and/or Specialists.
If the Location may be associated with PCP, system may identify it as PCP Office and allow PCP Office Staff User to be associated.
For each Location, a Primary Contact needs to be defined, so that all communications may be sent to this Contact.
System may allow communication preference to be set up for each Location.

TABLE 19

Functional Requirement Description - Insurance Management

System may allow an Insurance Company record to be added and saved.
System may allow an Insurance Company record to be updated and saved.
System may allow an authorized user to search for Insurance Company records.
System may allow added Insurance Company records to be selected when adding new Referral.
System may allow Insurance Plan to be added under Insurance Company.
System may allow Insurance Plan to be updated and saved.
System may allow authorized user to search for Insurance Plan records.
System may allow added Insurance Plan to be selected when adding new Referral.
System may identify whether the Insurance Plan requires authorization for Referral Appointment scheduling.

When a Patient visits his Primary Care Provider (PCP), and the PCP decides that a Specialist needs to be referred for this Patient—and this may be when a new Referral request may be submitted into the system.

When the Referral record is in the System, a System staff user may then schedule the appointment and keep track of the Referral.

TABLE 20

Functional Requirement Description - Referral Management

System may allow a PCP to submit a new Referral for a Patient associated with that PCP.
System may allow a PCP Office Staff User to submit a new Referral on behalf of PCP within the same office, by selecting the PCP first.
System may allow Patient to be selected if the Patient already has a profile in the system.
System may allow new Patient profile and information to be added and saved, if the Patient is new.
System may allow Patient information to be updated and saved, while adding a new Referral.
System may pre-populate a Patient's insurance company and details if already in the Patient's profile.
System may allow a Patient insurance company to be selected and information to be added and saved, while adding new Referral.
System may allow Patient insurance information to be updated and saved, while adding new Referral.
System may allow Patient billing information to be added and saved, while adding new Referral.
System may allow Patient billing information to be updated and saved, while adding new Referral.
System may allow Patient's preferred language to be defined, while adding new Referral, and the default language may be English.
System may allow Patient's Diagnosis Code(s) to be defined.
System may allow Specialty to be selected from the pre-defined list.
System may list Specialists based on the selection of insurance company and Specialty - only Specialists within the insurance's network and associated with selected Specialty may be listed.
System may allow new Specialist to be added, while adding new Referral.
System may ask to select one of the Specialist's Location, if multiple Locations may be associated.
System may ask to select the Referral Type - Normal or STAT.
System may allow Special Instructions/Patient history to be added for the Referral.
System may allow Notes to be added for the Referral.
System may allow the Referral request to be signed and submitted.
Once the Referral is submitted:
  For STAT Referrals, system may send notifications to assigned Referral Coordinator Manager right away.
  For Normal Referrals, system may send notifications to assigned Referral Coordinator Manager by end of day, with a count and summary of Normal Referrals.
System may allow multiple Referrals to be submitted for the same Patient, all at once.
System may save the Referral, but not yet submit.
System may filter Referrals by Referral Status and sub status.
Once the Referral is submitted, the Referral status may be "1 - New".
System May allow Referral Coordinator Manager to assign the "New" Referral to Referral Coordinator associated with the same Healthcare System/Hospital.
System may allow Referrals to be assigned individually or in bulk.
Once the Referral is assigned, system may send notifications to an assigned Referral Coordinator.
Once the Referral is assigned to a Referral Coordinator, the Referral status may be updated to "1 - New" with sub status as "Assigned".
If the $1^{st}$ call Referral Coordinator made to the Patient was not answered, system may send Reminder for $2^{nd}$ call in 2 days.
Once the Referral is be scheduled with appointment date, the Referral status may be updated to "2 - Scheduled" automatically.
System may send notifications to both Patient and Specialist when the appointment is scheduled.
If the Patient's Insurance does NOT require Authorization, once the Referral is scheduled it may also be automatically confirmed, with Referral status updated as "2 - Scheduled" and sub status as "Confirmed".
If the Patient's Insurance requires Authorization, once the Referral is scheduled, system may ask for Insurance Authorization.
System may allow insurance authorization to be attached to the Referral.
If the Patient's Insurance requires Authorization, and the Insurance Authorization is obtained, the Referral status may be updated as "2 - Scheduled" and sub status as "Confirmed" automatically.
System may send notifications to both Patient and Specialist when the appointment is confirmed.

TABLE 20-continued

Functional Requirement Description - Referral Management

Once the Referral is updated to status "2 - Scheduled", the full Referral script may be emailed and/or faxed to Specialist.
Patient may add the schedule date to Calendar when receiving the notification.
System may send Reminder to Patient [X] days (configurable) before the scheduled date.
System may allow Referral status to be changed to "5 - Patient Disregard".
System may allow Referral status to be changed to "6 - Unable to Contact".
For the Referrals with status changed to "5 - Patient Disregard" and "6 - Unable to Contact", system may send daily report to the PCP Office.
System may send follow up Email to Specialist, one week after the Appointment date automatically.
The follow up Email may include a link allowing a Specialist to select and respond with answers to the following questions:
    I. Has Patient Completed the Appointment? - Yes or No
      i. If "Yes", goes to the II question
      ii. If "No", select from the following conditions:
        a. Patient has rescheduled Appointment - if selected, reschedule date needs to be entered
        b. Patient was No Show
        c. Patient cancelled Appointment
    II. Is the Report Ready? - Yes or No
System may read the answers sent back via the follow up link and update Referral automatically.
System may read the reschedule date sent back by the Specialist and update the Referral with the new date.
System may log all the Referral schedule history, including appointment date/time and change date/time.
If NO response received one week from the $1^{st}$ follow up Email, system may send $2^{nd}$ follow up Email in one week.
If NO response received one week from the $2^{nd}$ follow up Email, system may send 3rd follow up Email in one week.
If NO response received after 3 follow up Email sent, system may send Alert to Follow Up Coordinator(s) that are assigned to the same Healthcare System/Hospital, after three weeks since $1^{st}$ follow up Email.
System may flag the Referral as "Follow Up" needed.
System may allow Follow Up Coordinator to assign Referral to itself.
System may display "Follow Up" Referrals by Specialist Office Location, so that the Follow Up Coordinator may follow up multiple Referrals with the same Location within one call.
Once the Referral receives feedback as "Patient has completed the Appointment" but Report may be still NOT ready, the Referral status may be updated to "3 - Exam Done" automatically.
Once the Referral receives feedback as "Patient has completed the Appointment" but Report may be still NOT received after one week, system may send Reminder to Specialist asking for Report.
If after one week since the Report Reminder sent, the Report may be still NOT received, system may send Alert to Follow Up Coordinator(s) that assigned to the same Healthcare System/Hospital.
System may send follow up Alert to all Follow Up Coordinators assigned to the same Healthcare System/Hospital with the Referral, and one Follow Up Coordinator may assign itself to the Referral.
System may log all Referral assignment history.
Once the Referral receives feedback as "Patient has completed the Appointment" and "Report may be Ready", the Referral status may be updated to "4 - Complete with Report" automatically.
Once system has received "Yes" for "Is the Report Ready?", system may send the generated unique bar code to the Specialist, who may then attach it to the Report and send the Report to System.
System may also allow authorized user (Follow Up Coordinator) to click and generate the unique bar code for every Referral, and send it to Specialist who may then attach it to the Report.
Once the Report is received with bar code attached, system may send (fax and/or email) the Report to PCP Office and updated to "4 - Complete with Report" automatically.
System may also save the Report with bar code and attach it to the Referral in the system, so that it may be accessed by an authorized user.
System may be able to generate bar code with the "Universal Product Code" format and in AVERY 8366TM size.
Once the Referral receives feedback as "Patient has NOT completed the Appointment" and "No Show", the Referral status may be updated to "5 - Patient Disregard" with sub status as "No Show" automatically.
Once the Referral receives feedback as "Patient has NOT completed the Appointment" and "Cancellation", the Referral status may be updated to "5 - Patient Disregard" with sub status as "Cancellation" automatically.
Once the Referral status may be changed to "5 - Patient Disregard" with sub status as "No Show" or "Cancellation", system may send notifications to the Patient asking the Patient to call back and reschedule.
System may allow Referral status to be changed to "5 - Patient Disregard" with or without sub status.
System may allow Referral status to be changed to "6 - Unable to Contact".
System may allow Referral to be flagged as "Management Attention", which may send notifications to System Admin User and Referral Coordinator Manager automatically.
System may allow Notes to be added for Referral, with date/time captured.
System may allow Document to be attached to Referral.
Referral Coordinator Manager may assign Referral Coordinator to the Referral; and Follow Up Coordinator may be able to assign himself to the Referral.
Referral Coordinator and Follow Up Coordinator may be assigned and work on the same Referral.
System may allow Referrals to be searched by Healthcare System and Hospital.
System may allow Referrals to be searched by PCP and PCP Office.
System may allow Referrals to be searched by Patient information, including Patient Last and First Name, Patient DOB and Patient Insurance provider.
System may allow Referrals to be searched by Specialty, Specialist and Specialist Office.
System may allow Referrals to be searched by submission date range.
System may allow Referrals to be searched by appointment schedule date range.
System may allow Referral search criteria to be saved by naming it.
System may allow saved Referral search criteria to be retrieved and edited.

ER/Hospital Admission Management

When Patient has been admitted to an ER or Hospital, notifications may be sent to System. Therefore, an ER/Hospital Admission record may be added in the system for the Patient, and System staff may keep track of it.

TABLE 21

Functional Requirements Description

System may allow new ER/Hospital admission record to be added and saved.
System may allow new ER/Hospital admission record to be updated and saved.
System may allow authorized user to search for ER/Hospital admission record.
System may attach added ER/Hospital admission record to Patient profile.
System may send notifications to PCP Office when new ER/Hospital admission record added.
System may allow Patient Discharge date/time to be added.
System may send notifications to PCP Office when the Patient may be discharged.
System may allow Notes to be added for ER/Hospital admission record with date/time captured.
System may send notifications to PCP office, through fax or email, when Patient disregard System's follow up request.

Invoices may be generated based on number of Referrals and ER/Hospital Admission records created, applied with rates. Invoices may be generated for each Healthcare System account monthly.

TABLE 22

| Functional Requirements Description |
| --- |
| System may generate invoice for each Healthcare System account monthly. |
| Invoice may include total number of Referrals created, with rates applied, for each account. |
| Invoice may include total number of ER/Hospital Admission records created, with rates applied, for each account. |
| Invoice may be exported and printed. |

Communication Management

TABLE 23

| Functional Requirements Description |
| --- |
| System may allow communication preferences to be set up for Patient, PCP, Specialist and Location - PCP Office and Specialist Office. |
| Communication preferences may include: |
|    Email, when selected Email address is required |
|    Text, when selected Cell Phone number is required |
|    Fax, when selected Fax number is required |
|    Mail, when selected Mailing address is required |
| System may send all communications, including notifications, reminders and alerts based on preferences and information provided. |
| System may report back if the Email failed to send. |
| System may report back if the Text failed to send. |
| System may report back if the Fax failed to send. |

Report Management

There may be pre-defined reports that may be viewed by authorized users, who may also edit and save the new search criteria as a new report, as well as create new search criteria and generate reports periodically.

TABLE 24

| Functional Requirements Description - Reports |
| --- |
| System may allow user to view pre-defined reports, based on user roles. |
| System may allow user to change the search criteria for existing reports and save them as new ones. |
| System may allow user to create new search criteria to generate new reports and save them. |
| System may generate all the reports with real time data. |
| Report may be printed and exported as a "pdf" or "csv" or "excel" file. |
| End of Month Report - This may list a Referral count with PCP and Leakage information associated for each Specialty/Specialist end of month, for every Healthcare System. It may include: |
|   Referral Totals by PCP |
|   Referral Count by Status (both table and pie chart) |
|   Leakage Referral by Specialty |
|   In-/Out- Network Referral Count by Specialist and Specialty |
|   In-/Out-of- Network Referral Totals (both table and pie chart) |
| Mid-Month Report - This may list Referral count for PCP and totals, until the middle of each month, for every Healthcare System/Hospital. It may include: |
|   Referral Totals by PCP |
|   Referral Grant Total |
| Leakage Trend Report - This may list Referral leakage trend by Specialty and Location, for every Healthcare System. It may include: |
|   Leakage Count summary: display number of leakage by Year or Month for each Healthcare system (both table and column chart) |
|   Leakage Count by Specialty: display number of leakage based on Specialty by Year for each Healthcare system (both table and column chart) |
|   Leakage Count by Zip and Specialty: display number of leakage based on Zip code for each Specialty, by Year for each Healthcare System |
|   Leakage Cluster: display request cluster vs. leakage cluster on a map |
| Referral Density Report - This report may visualize the referral density based on criteria of PCP referrals to any Specialist, which may show where the referrals may be coming from and where the referrals may be going with numbers, on map. The Referral Density Report also may identify distance from the PCP to the Specialists, in miles. Thus, the hospital or healthcare system will be able to identify areas of need based on the number of referrals and distances patients are required to travel to place specialists in closer proximity to the PCP as required. This information may be obtained by reviewing the density report, the number of referrals, the distance of the patient's travel, and the specialist identified. |
| Healthcare System Summary Report - This may list Referral totals for each Healthcare System, for selected data range, so that System Admin may have an overview of all the systems. |
| New Referral Report - This may list all new Referrals that are submitted in the system but have not been taken care of. |
| Referral Assignment Report - This may list Referral count by assigned Referral Coordinator, including total number of Referrals assigned, number of Referrals scheduled, number of Referrals with status changed, number of Notes added for assigned Referrals, for each RC. |
| Daily Referral Submission Report - This may list Referrals submitted for the day, and may be sent to the Referral Coordinator Manager at end of the day. |
| Report Status Report - This may list Referrals based on status, including communication status, for selected Date Range, by Specialty; and System Admin User may also view it by Healthcare System. |

Technical Description

The purpose of this technical description is to describe the technical design of the exemplary embodiments of the AMTVR system and of exemplary system implementation. This description describes the modules of the AMTVR system, and includes architecture and class diagrams, along with database tables.

The technical description details functionality provided by each subsystem or group of subsystems of exemplary embodiments and shows how the various subsystems interact.

An exemplary embodiment may comprise a website that may be built using HTML 5 with JQuery I. Ix. Data may be pulled from the SQL database server using the Web API controller. The service layer may be built using .NET C#. For all data-related needs, the restful service may be called, which in turn may fetch the data from the SQL server and send the data back to the website.

An exemplary technical stack utilized for the AMTVR system includes the following five languages/APis:
1. Front End development over HTML 5.0;
2. Bootstrap (CSS);
3. JQuery I. Ix based data binding/validation;
4. Net C# Based RESTful APis; and
5. MS SQL Server 2014.

Figure 5:
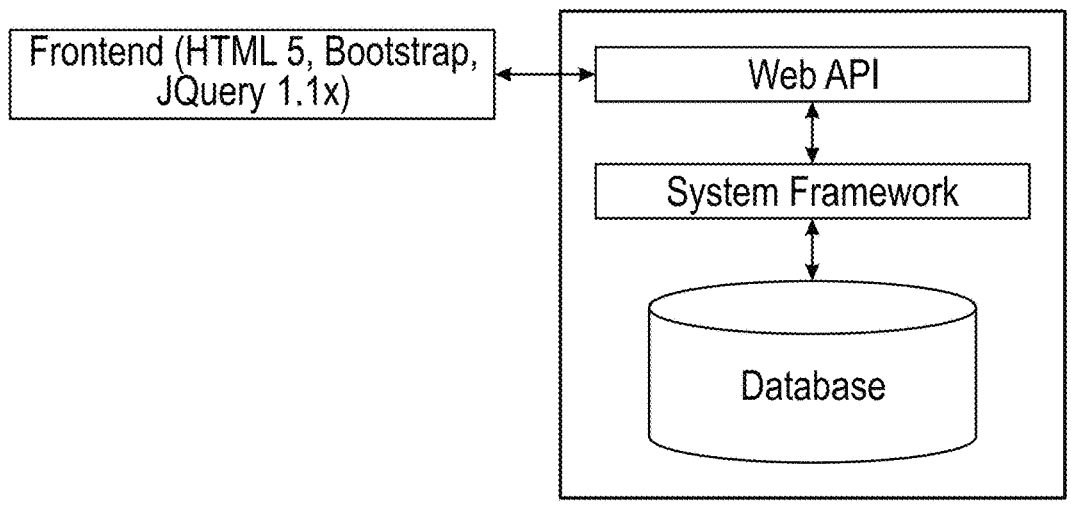
FIG. 5 depicts technical architecture of an exemplary embodiment.

An exemplary technical architecture is depicted in FIG. 5. The AMTVR system may be deployed on cloud/web servers and may work in part as a web application. Other components such as database and services may also be deployed on secure (SSL) cloud/web servers. To use the AMTVR system, a user may be within the domain network and may have appropriate credentials to login and perform certain operations.

Figure 6:
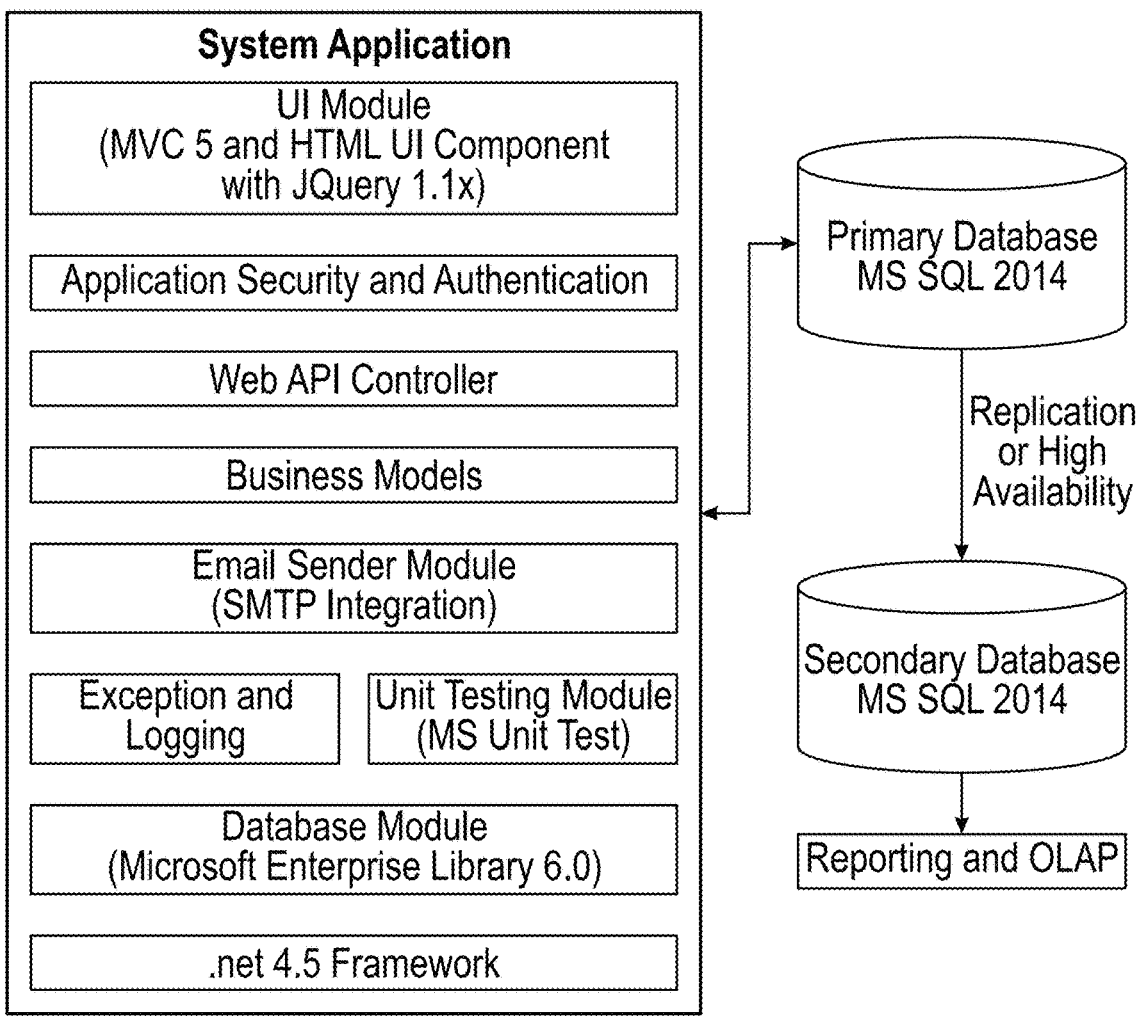
FIG. 6 is a logical and physical design diagram of an exemplary embodiment.

An exemplary logical and physical high level design diagram is depicted in FIG. 6 with the following features.
- UI Module: Presentation layer which may be implemented with MVC 5 framework and HTML UI components.
- Authentication: Login and Authentication may be done through the AMTVR system database and passwords may be encrypted through MD5 Hash.

Web API: Web API exposes restful end points. Depending upon the payload, it executes the corresponding system process and sends out back to the client in JSON over HTTP.

Email Module: Mailing engine to send emails for forgotten password, reset requests, unlock user requests, and the like.

Unit Testing Module: Unit tests may be written on a MS unit testing framework.

Exception Logging: Class library for exception handling and logging to the database and sending notifications to administration by email as well.

Database Layer: Data module uses Microsoft Enterprise Library 6.0 to interact with SQL Server 2014. Stored procedure and user defined function may interact with data layer.

Figure 7:
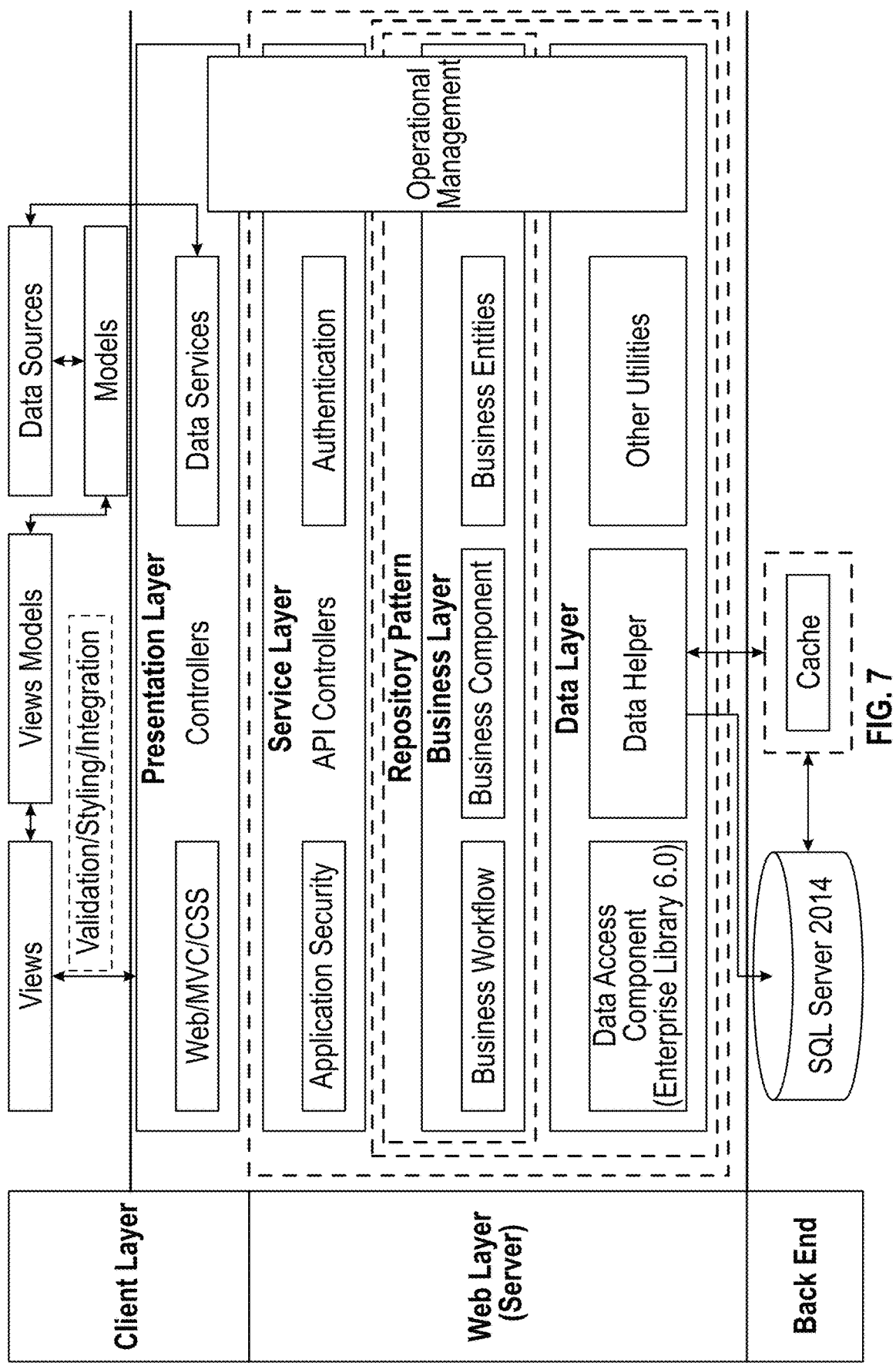
FIG. 7 is a system physical and logical design diagram of an exemplary embodiment.
Figure 8:
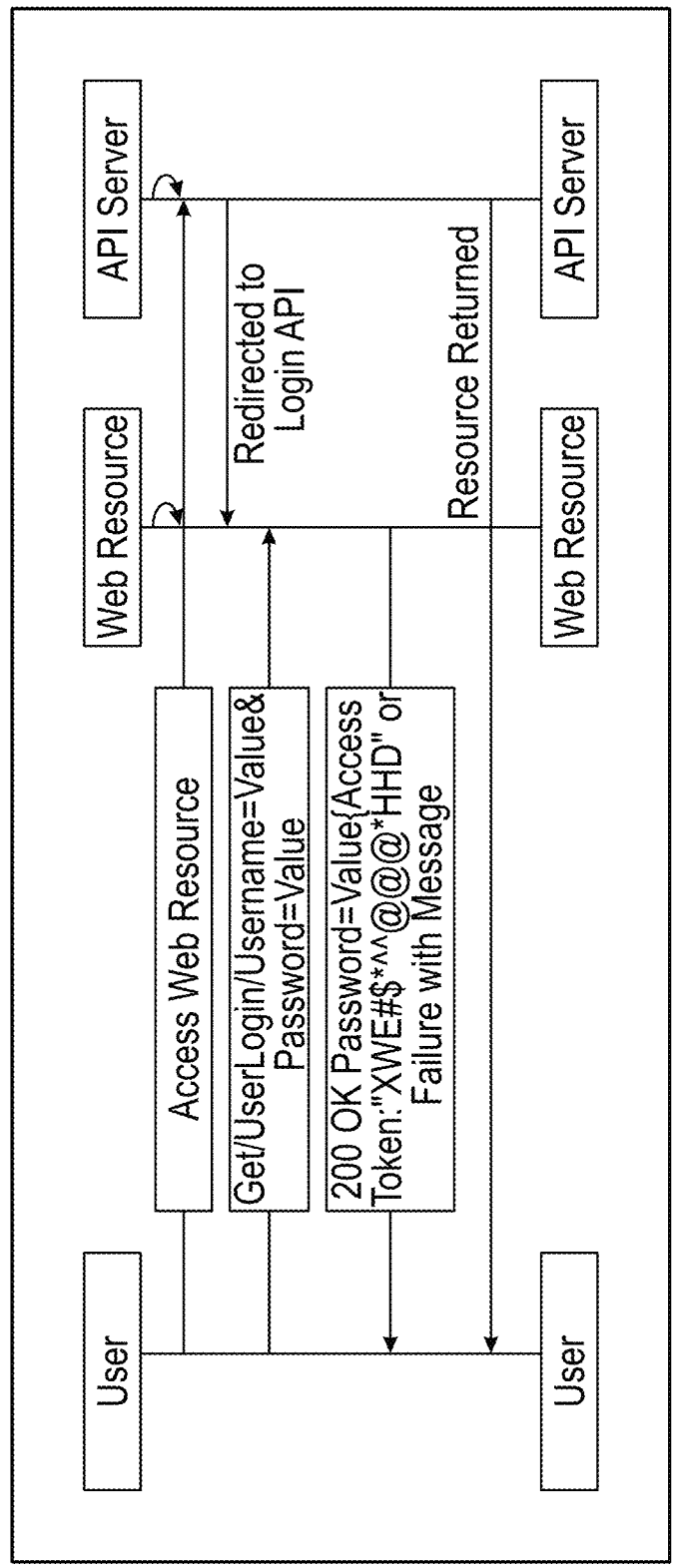
FIG. 8 is a diagram depicting an authentication process of an exemplary embodiment.

An exemplary system physical and logical high level design diagram is shown in FIG. 7, which explains various components and their interactions in the context of the AMTVR system. The AMTVR system may include a number of basic layers such as, but not limited to, the following.

1. backend;
2. web layer (server); and
3. client layer.

The backend includes the database (SQL Server 2014) of the AMTVR system along with server side caching. The data layer may consume the data provided by the backend layer. Database interactions occur in the AMTVR system using the repository system. The repositories in the AMTVR system may be derived from a repository interface. Additional components of the AMTVR system may use the repository interfaces to perform data manipulation.

The web layer (server) may include the following layers.

Data Layer: This layer provides access to data hosted within the boundaries of the system. The data layer exposes generic interfaces that the components in the system layer may consume. The data layer includes a data access component (Enterprise Library 6.0), data helper and other utilities.

System layer: This layer implements the core functionality of the AMTVR system, and encapsulates the relevant system logic. This layer includes components, workflow, and entities.

Presentation layer: This layer includes the user oriented functionality responsible for managing user interaction with the AMTVR system, and includes components that provide a common bridge into the core system logic encapsulated in the system layer. In addition, security and operational management may be provided on each of the layers. Security includes permissions, membership, xss attack, and the like. Operational management includes logging information, configuration, tracing, caching, and the like.

Client layer: The client may access the web layer through the Internet. The client layer may be tightly coupled with view, model, and view models. Validations may be placed through JQuery.

Exemplary security features include the following.

Secure Login: Passwords may be saved in an encrypted form in the AMTVR system database.

Access control and Authentication: Users may be restricted within the boundary of their role and permissions to access the component of the application. Each user is to be associated with some role and certain privileges of that role may be applicable with respect to that user.

Brute force attack: The AMTVR system is blocked in the event of more than three (3) consecutive incorrect password attempts to avoid brute force and automatic script login attacks.

SQL injection: A common attack in which the attacker may append an SQL script element with input to expose the internal application or damage data. Thus, freeform inputs from the user are verified.

Server side authentication and authorization: Even if an attacker changes the UI elements or URL injection (appending the URL with an id) to gain access to restricted information, the AMTVR system verifies authorization of the request on the server side and only grants access if the user has the right to access the applicable resource.

Cross Site Scripting: The success of this attack requires the victim to execute a malicious URL that may be crafted in such a manner as to appear to be legitimate. When visiting such a crafted URL, an attacker may effectively execute an attack to the victim's browser. A malicious Javascript, for example, may be run in the context of the web site that possesses the XSS bug. Along with .NET framework's inbuilt functionality to validate the incoming request and malformed URL, the AMTVR system implements a proper validation process of the input and anti-forgery token.

Users must be authenticated: A token is generated by the AMTVR system. Subsequent calls may be verified by matching an authentication token, failing which the request is terminated, with the attempting user being shown an appropriate message.

Platform Support

The website aspect may run on popular browsers available in the market, such as:

TABLE 25:

| Browser/Platforms |
| --- |
| Internet Explorer v-10 or higher /Chrome v-54 or higher /Firefox v-50 or higher /Safari v-5.1 or higher |
| All different mobile devices including IPhone, Samsung, LG and other models using the iOS, Android and Windows platforms |

Appendix

TABLE 26

Dashboard - Dashlet Examples

| Dashlet Name | Type | User Role | Description |
| --- | --- | --- | --- |
| Healthcare System Referral Summary | Table | Healthcare System Admin | Display "Number of Referrals" categorized by Hospital, for selected date range - system may display data for current month by default, including:<br>  Hospital Name<br>  Total of Referrals |

TABLE 26-continued

Dashboard - Dashlet Examples

| Dashlet Name | Type | User Role | Description |
| --- | --- | --- | --- |
| Leakage by Specialty/Specialist | Table | Healthcare System Admin | In-Network Referrals # <br> Leakage Referrals # <br> Display "Number of In-Network Referrals" and "Number of Leakage Referrals" by Specialty and Specialist, for selected date range - system may display data for current month by default, which also allows user to select All or One Hospital from the network; for each Specialty, Total In- and Out- Network Referrals # may first be displayed, then for each Specialist, including: <br>    Specialty Name <br>    Specialist Last, First Name <br>    In-Network Referrals # <br>    Specialty Name <br>    Specialist Last, First Name <br>    Leakage Referrals # <br> * Clicking "More. . ." may redirect user to the Report - Leakage by Specialty/; Specialist Report page, with more details displayed. |
| Leakage Trend Summary | Column Chart | Healthcare System Admin | Display "Number of Leakage Referrals" by Year or Month, for selected Year/Month range in a column chart format for this Healthcare System, which also allows user to select All or One Specialty from the list; system may display "Number of Leakage Referrals" by Month for current year for All Specialty in total. |
| Referral by PCP | Table | Healthcare System Admin | Display "Number of Referrals" by PCP associated with this Healthcare System, which also allows a user to select All or One Hospital from the list, for selected data range - system may display data for current month by default, including: <br>    PCP Name <br>    # of Referrals <br> * Clicking "More. . ." may redirect user to the Report - Referral by PCP Report page, with more details displayed. |
| Referral Status Summary | Table, Pie Chart | Healthcare System Admin | Display "Number of Referrals" by Referral Status for this Healthcare System, which also allows user to select All or One Hospital from the list, for selected date range - system may display data for current month by default, including: <br>    Referral Status <br>    # of Referrals <br>    Percentage <br> * Clicking "Chart" icon may display the data in a pie chart format <br> * User may be able to switch between Table and Chart display <br> * Clicking "More. . ." may redirect user to the Report - Referral Status Report page, with more details displayed. |
| Top 10 Referral Specialty | Table | Healthcare System Admin | Display top 10 Specialties that get referred within this Healthcare System, for selected date range, including: <br>    Specialty Name <br>    # of Referrals |
| New Referral | Table | Healthcare System Admin | Display new referrals for the Healthcare System, which also allows user to select All or One Hospital from the Hospital list within the network, including: <br>    Referral # <br>    PCP <br>    Patient <br>    Specialty <br>    Specialist <br>    In/Out Network <br> * Clicking "More. . ." may redirect user to the Report - New Referral Report page, with more details displayed. |

TABLE 26-continued

Dashboard - Dashlet Examples

| Dashlet Name | Type | User Role | Description |
| --- | --- | --- | --- |
| Hospital Referral Summary | Table, Pie Chart | Hospital Admin | Display "Number of Referrals" for this Hospital, for selected date range - system may display data for current month by default, including:<br>    Total of Referrals<br>    In-Network Referrals #<br>    Leakage Referrals #<br>* The data may also be displayed in a pie chart format, with In-Network and Leakage Referrals Percentage |
| Leakage by Specialty/Specialist | Table | Hospital Admin | Display "Number of In-Network Referrals" and "Number of Leakage Referrals" by Specialty and Specialist, for selected date range - system may display data for current month by default; for each Specialty, Total In- and Out- Network Referrals # may first be displayed, then for each Specialist, including:<br>    Specialty Name<br>    Specialist Last, First Name<br>    In-Network Referrals #<br>    Specialty Name<br>    Specialist Last, First Name<br>    Leakage Referrals #<br>* Clicking "More. . ." may redirect user to the Report - Leakage by Specialty/; Specialist Report page, with more details displayed. |
| Leakage Trend Summary | Column Chart | Hospital Admin | Display "Number of Leakage Referrals" by Year or Month, for selected Year/Month range in a column chart format for this Hospital, which also allows user to select All or One Specialty from the list; system may display "Number of Leakage Referrals" by Month for current year for All Specialty in total. |
| Referral by PCP | Table | Hospital Admin | Display "Number of Referrals" by PCP associated with this Hospital, for selected data range - system may display data for current month by default, including:<br>    PCP Name<br>    # of Referrals<br>* Clicking "More. . ." may redirect user to the Report - Referral by PCP Report page, with more details displayed. |
| Referral Status Summary | Table, Pie Chart | Hospital Admin | Display "Number of Referrals" by Referral Status for this Hospital, for selected date range<br>    system may display data for current month by default, including:<br>    Referral Status<br>    # of Referrals<br>    Percentage<br>* Clicking "Chart" icon may display the data in a pie chart format<br>* User may be able to switch between Table and Chart display<br>* Clicking "More. . ." may redirect user to the Report - Referral Status Report page, with more details displayed. |
| Top 10 Referral Specialty | Table | Hospital Admin | Display top 10 Specialties that get referred for the Hospital, for selected date range, including:<br>    Specialty Name<br>    # of Referrals |
| New Referral | Table | Hospital Admin | Display new referrals for the Healthcare System - Hospital, including:<br>    Referral #<br>    PCP<br>    Patient<br>    Specialty<br>    Specialist<br>    In/Out Network<br>* Clicking "More. . ." may redirect user to the Report - New Referral Report page, with more details displayed. |
| New Referral | Table | PCP | Display new referrals submitted by this PCP, which also allows user to select All or One of PCP Office Location from the Locations list associated with the PCP, including: |

TABLE 26-continued

Dashboard - Dashlet Examples

| Dashlet Name | Type | User Role | Description |
| --- | --- | --- | --- |
| | | | Referral #<br>PCP Office<br>Patient<br>Specialty<br>Specialist<br>In/Out Network<br>* Clicking "More. . ." may redirect user to the Report - New Referral Report page, with more details displayed. |
| My Notifications | Table | PCP | Display notifications sent to this PCP, including:<br>   Notification Date<br>   Notification Description |
| Referral Status Summary | Table, Pie Chart | PCP | Display "Number of Referrals" by Referral Status submitted by this PCP, for selected date range - system may display data for current month by default, including:<br>   Referral Status<br>   # of Referrals<br>   Percentage<br>* Clicking "Chart" icon may display the data in a pie chart format<br>* User may be able to switch between Table and Chart display<br>* Clicking "More. . ." may redirect user to the Report - Referral Status Report page, with more details displayed. |
| New Referral | Table | PCP Office Staff | Display new referrals submitted by this PCP Office Staff for the PCP Office, including:<br>   Referral #<br>   PCP<br>   Patient<br>   Specialty<br>   Specialist<br>   In/Out Network<br>* Clicking "More. . ." may redirect user to the Report - New Referral Report page, with more details displayed. |
| My Notifications | Table | PCP Office Staff | Display notifications sent to this PCP Office, including:<br>   Notification Date<br>   Notification Description |
| Referral Status Summary | Table, Pie Chart | PCP Office Staff | Display "Number of Referrals" by Referral Status submitted by this PCP Office Staff, for selected date range - system may display data for current month by default, including:<br>   Referral Status<br>   # of Referrals<br>   Percentage<br>* Clicking "Chart" icon may display the data in a pie chart format<br>* User may be able to switch between Table and Chart display<br>* Clicking "More. . ." may redirect user to the Report - Referral Status Report page, with more details displayed. |
| Healthcare System Referral Summary | Table | System Staff Admin | Display "Number of Referrals" categorized by Healthcare System, for selected date range - system may display data for current month by default, including:<br>   Healthcare System Name<br>   Total of Referrals<br>   In-Network Referrals #<br>   Leakage Referrals # |
| Leakage by Specialty/Specialist | Table | System Staff Admin | Display "Number of In-Network Referrals" and "Number of Leakage Referrals" by Specialty and Specialist, for selected date range - system may display data for current month by default, which also allows user to select All or One Healthcare System; for each Specialty, Total In- and Out- Network Referrals # may first be displayed, then for each Specialist, including:<br>   Specialty Name<br>   Specialist Last, First Name<br>   In-Network Referrals #<br>   Specialty Name |

TABLE 26-continued

Dashboard - Dashlet Examples

| Dashlet Name | Type | User Role | Description |
|---|---|---|---|
| | | | Specialist Last, First Name<br>Leakage Referrals #<br>* Clicking "More. . ." may redirect user to the Report - Leakage by Specialty/; Specialist Report page, with more details displayed. |
| Leakage Trend Summary | Column Chart | System Staff Admin | Display "Number of Leakage Referrals" by Year or Month, for selected Year/Month range in a column chart format for All or One Healthcare System, and All or One Specialty from the list; system may display "Number of Leakage Referrals" for current year for All Healthcare Systems and All Specialty in total. |
| Top 10 Referral Healthcare System | Table | System Staff Admin | Display top 10 Healthcare Systems with the most Referrals submitted, for selected date range - system may display data for current month by default, including:<br>    Healthcare System Name<br>    # of Referrals |
| Top 10 Referral PCP | Table | System Staff Admin | Display top 10 PCP with the most Referrals submitted, for selected date range - system may display data for current month by default, including:<br>    PCP Name<br>    Healthcare System Name<br>    # of Referrals |
| Top 10 Referral Specialty | Table | System Staff Admin | Display top 10 Specialties that get referred for All or One Healthcare System, for selected date range, including:<br>    Specialty Name<br>    # of Referrals |
| Referral Status Summary | Table, Pie Chart | System Staff Admin | Display "Number of Referrals" by Referral Status for All or One Healthcare System from the list, for selected date range - system may display data for current month by default, including:<br>    Referral Status<br>    # of Referrals<br>    Percentage<br>* Clicking "Chart" icon may display the data in a pie chart format<br>* User may be able to switch between Table and Chart display<br>* Clicking "More. . ." may redirect user to the Report - Referral Status Report page, with more details displayed. |
| New Referral | Table | System Staff Admin | Display new referrals submitted in the system, which also allows user to select All or One Healthcare System from the Hospital list within the network, including:<br>    Healthcare System Name<br>    Referral #<br>    PCP<br>    Patient<br>    Specialty<br>    Specialist<br>    In/Out Network<br>* Clicking "More. . ." may redirect user to the Report - New Referral Report page, with more details displayed. |
| New Referral Assignment | Table | System Staff Admin | Display referrals that newly get assigned to Referral Coordinator, for All for One Healthcare System, including:<br>    Healthcare System Name<br>    Referral #<br>    Assigned By<br>    Assigned To<br>    Assigned Date |
| Legacy Referral | Table | System Staff Admin | Display referrals that have not been Closed for [X time period] since submitted, for All or One Healthcare System, including:<br>    Healthcare System Name<br>    Referral #<br>    Referral Status<br>    Assigned To<br>    Submitted Date<br>* Clicking "More. . ." may redirect user to the |

TABLE 26-continued

Dashboard - Dashlet Examples

| Dashlet Name | Type | User Role | Description |
| --- | --- | --- | --- |
| | | | Report - Legacy Referral Report page, with more details displayed. |
| My Notifications | Table | Referral Coordinator Manager | Display notifications sent to this PCP, including:<br>    Notification Date<br>    Notification Description |
| New Referral | Table | Referral Coordinator Manager | Display new referrals for the assigned Healthcare System and Hospital, which allows user to select All or One Healthcare System from the assigned list and All or One Hospital from the assigned list, including:<br>    Referral #<br>    PCP<br>    Patient<br>    Specialty<br>    Specialist<br>    In/Out Network<br>* Clicking "More. . ." may redirect user to the Report - New Referral Report page, with more details displayed. |
| Referral Status Summary | Table, Pie Chart | Referral Coordinator Manager | Display "Number of Referrals" by Referral Status for All or One assigned Healthcare System/Hospital from the list, for selected date range - system may display data for current month by default, including:<br>    Referral Status<br>    # of Referrals<br>    Percentage<br>* Clicking "Chart" icon may display the data in a pie chart format<br>* User may be able to switch between Table and Chart display<br>* Clicking "More. . ." may redirect user to the Report - Referral Status Report page, with more details displayed. |
| Legacy Referral | Table | Referral Coordinator Manager | Display referrals that have not been Closed for [X time period] since submitted, for All or One assigned Healthcare System/Hospital from the list, including:<br>    Healthcare System Name<br>    Referral #<br>    Referral Status<br>    Assigned To<br>    Submitted Date<br>* Clicking "More. . ." may redirect user to the Report - Legacy Referral Report page, with more details displayed. |
| Referral Assignment Summary | Table | Referral Coordinator Manager | Display number of Referrals assigned by Referral Coordinator and Follow Up Coordinator that assigned with the same Healthcare System/Hospital, including:<br>    Staff User Name<br>    Staff User Role - Referral Coordinator or Follow Up Coordinator<br>    # of Referrals assigned to |
| My Notifications | Table | Referral Coordinator | Display notifications sent to this PCP, including:<br>    Notification Date<br>    Notification Description |
| New Referral | Table | Referral Coordinator | Display new referrals for the assigned Healthcare System and Hospital, which allows user to select All or One Healthcare System from the assigned list and All or One Hospital from the assigned list, including:<br>    Referral #<br>    PCP<br>    Patient<br>    Specialty<br>    Specialist<br>    In/Out Network<br>* Clicking "More. . ." may redirect user to the Report - New Referral Report page, with more details displayed. |

TABLE 26-continued

Dashboard - Dashlet Examples

| Dashlet Name | Type | User Role | Description |
| --- | --- | --- | --- |
| My Assignment | Table | Referral Coordinator | Display referrals that assigned to this user, including:<br>　Referral #<br>　PCP<br>　Patient<br>　Specialty<br>　Specialist<br>　Referral Status |
| My Notifications | Table | Follow Up Coordinator | Display notifications sent to this PCP, including:<br>　Notification Date<br>　Notification Description |
| New Referral | Table | Follow Up Coordinator | Display new referrals for the assigned Healthcare System and Hospital, which allows user to select All or One Healthcare System from the assigned list and All or One Hospital from the assigned list, including:<br>　Referral #<br>　PCP<br>　Patient<br>　Specialty<br>　Specialist<br>　In/Out Network<br>* Clicking "More. . ." may redirect user to the Report - New Referral Report page, with more details displayed. |
| My Assignment | Table | Follow Up Coordinator | Display referrals that assigned to this user, including:<br>　Referral #<br>　PCP<br>　Patient<br>　Specialty<br>　Specialist<br>　Referral Status |

The workflow diagrams included herein use System Process Model Notation (BPMN) 2.0, which is an international standard for system process modeling. The symbols depicted in FIG. 9 may be used.

Embodiments comprise computer components and computer-implemented steps that will be apparent to those skilled in the art. For example, calculations and communications are performed electronically, and results can be displayed using a graphical user interface.

Figure 10:
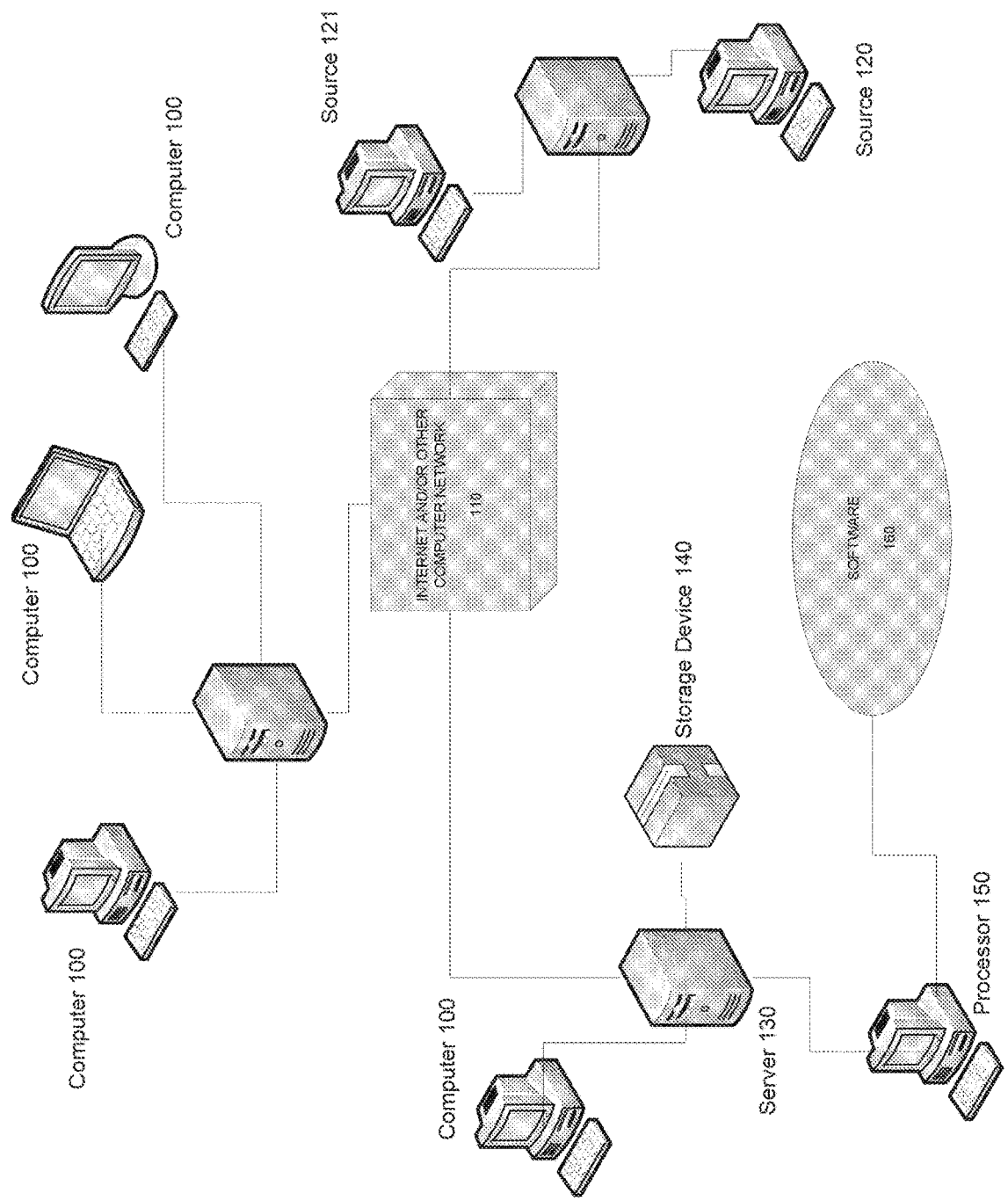
FIG. 10 is a block diagram of a computer system of an embodiment.

An exemplary system is depicted in FIG. 10. Computers 100 communicate via network 110 with a server 130. A plurality of sources of data 120-121 also communicate via network 110 with a server 130, processor 150, and/or other components operable to calculate and/or transmit information. Server(s) 130 may be coupled to one or more storage devices 140, one or more processors 150, and software 160.

Calculations described herein, and equivalents, are, in exemplary embodiments, performed entirely electronically. Other components and combinations of components may also be used to support processing data or other calculations described herein as will be evident to one of skill in the art. Server 130 may facilitate communication of data from a storage device 140 to and from processor(s) 150, and communications to computers 100.

Processor 150 may optionally include or communicate with local or networked storage (not shown) which may be used to store temporary or other information. Software 160 can be installed locally at a computer 100, processor 150, and/or centrally supported for facilitating calculations and applications.

For ease of understanding, not every step or element of the exemplary embodiments is explicitly described herein as part of a computer system, but those skilled in the art will recognize that each component, module, process, step, or element may have a corresponding computer system hardware component. Such computer system and/or software components are, therefore, enabled by describing their corresponding steps or elements (that is, their functionality), and are within the scope of the invention.

Moreover, where a computer system is described or claimed as having a processor for performing a particular function, it will be understood by those skilled in the art that such usage should not be interpreted to exclude systems where a single processor, for example, performs some or all of the tasks delegated to the various processors. That is, any combination of, or all of, the processors specified in the description and/or claims may be the same processor. All such combinations are within the scope of the invention.

Alternatively, or in combination, processing and decision-making may be performed by functionally equivalent circuits such as a digital signal processor circuit or an application specific integrated circuit.

FIG. 10 illustrates a block diagram of an exemplary computer system that is suitable for use with exemplary embodiments. However, embodiments are operable in any of several computing environments that can include a variety of hardware, operating systems, and program modules. Program modules may include, but are not limited to, processors, routines, programs, components, data structures, and the like that perform particular tasks and/or implement particular data types.

Moreover, those skilled in the art will understand that embodiments may be practiced with other computer system configurations including, but not limited to, hand-held devices, network computers, multiprocessor based systems, microprocessor-based or other special purpose or proprietary programmable consumer electronics, minicomputers, mainframes, and the like. Exemplary embodiments may also be practiced in distributed computing environments where tasks are performed by remote processing devices that are linked through communications networks. In a distributed computing environment, program modules may be located in and/or executed from local and/or remote memory storage devices.

Exemplary embodiments and any other necessary programmed instructions and/or commands may be executable on processor 150. Processor 150 stores and/or retrieves programmed instructions and/or data from memory devices that can include, but are not limited to, Random Access Memory (RAM) and Read Only Memory (ROM) by way of a memory bus (not shown). User input to computer system 100 may be entered by way of a keyboard and/or pointing device. Human readable output from processor 150 may be viewed on an electronic display or in printed form on a local printer. Alternatively, processor 150 may be accessible by remote users for purposes that can include debugging, input, output and/or generating human readable displays in printed and/or display screen output form, or any other output form, by way of a Local Area Network (LAN) or Wide Area Network (WAN).

Many routine program elements, such as initialization of loops and variables and the use of temporary variables, are not described herein. Moreover, it will be appreciated by those of ordinary skill in the art that unless otherwise indicated, the particular sequence of steps described is illustrative only and can generally be varied without departing from the scope of the invention. Unless otherwise stated, the processes described herein are unordered, that is, the processes can be performed in any reasonable order.

Figure 11:
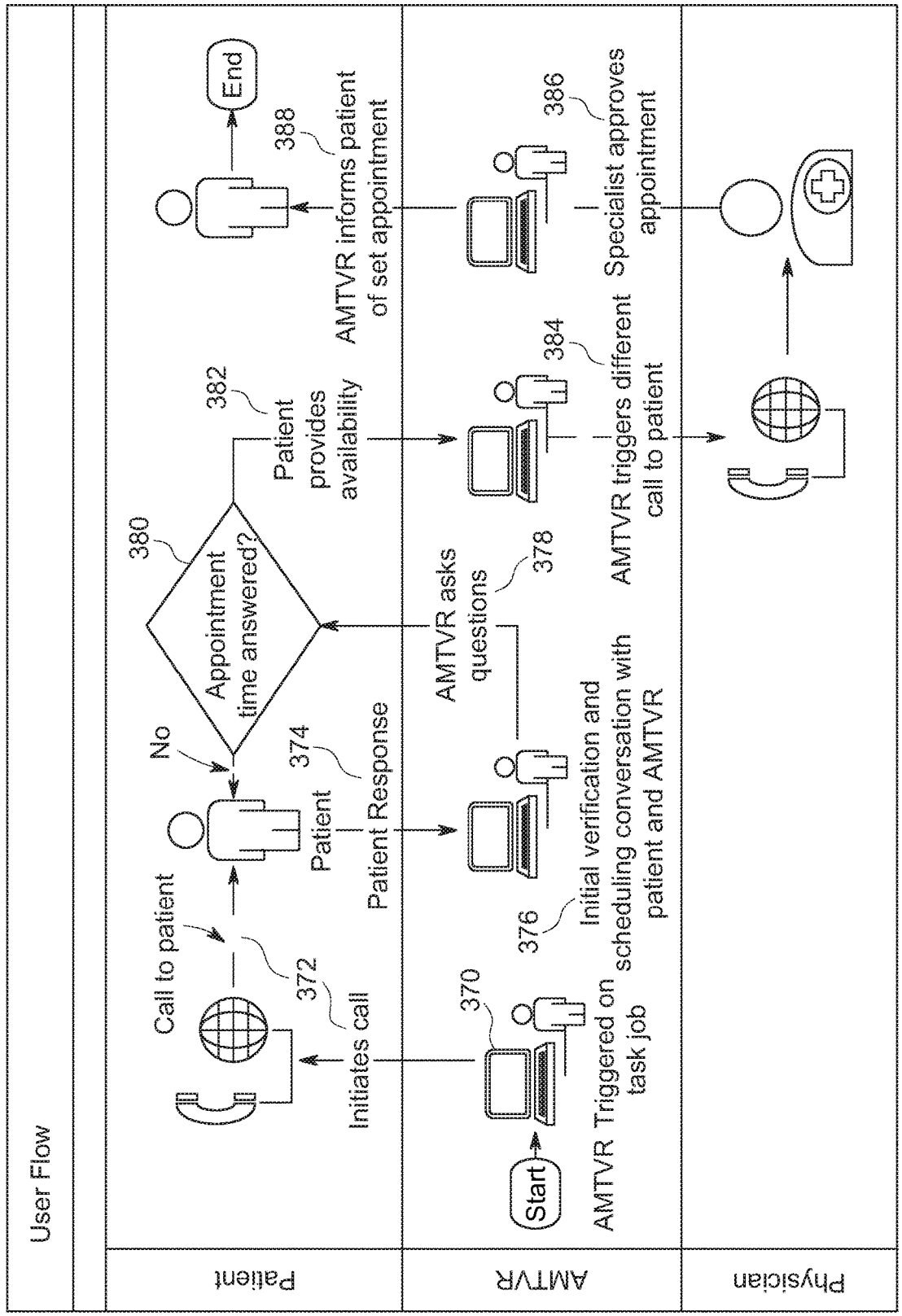
FIG. 11 is a flowchart of an appointment monitoring and tracking voice recognition (AMTVR) system from a user's perspective.

Functional specifications for an appointment monitoring and tracking voice recognition (AMTVR) or AIVR system, which is capable of being integrated with a referral system are based on business processes including, but not limited to, initiating a call to a patient and initiating a call to a physician or specialist. It is to be noted that the AMTVR is configured to understand conversational modes directed towards specific dialogues programmed into the AMTVR. In addition, the AMTVR is self-learning and has the ability to integrate future discussions relating to referral coordination. FIG. 11 is a flowchart showing operation of the AMTVR system. The process begins with the AMTVR system being triggered by a task job 370 and initiating a call to the patient 372, at which point the AMTVR system specifies that the initial verification of the patient is a HIPPA requirement and that the AMTVR system meets the per requirement protocols. The patient responds to the AMTVR system for the initial verification and scheduling conference 376. The AMTVR system then asks the patient one or more questions 378 regarding, for example, an appointment date and time 380, which the patient answers 382. The AMTVR system then makes a different call to the physician's office 384, which may then, for example, approve the appointment 386 via the AMTVR system. The AMTVR system then informs the patient that the appointment has been scheduled 388. In one or more embodiments, the AMTVR system queries the patient as to whether the patient would like the earliest appointment available or a specific date and time in the future. The AMTVR system then places the patient on hold and calls the physician's office. In response to the call being answered and depending on the patient's request, the AMTVR system requests the earliest appointment available or an appointment, at the time and date specified by the patient, from the specialist's receptionist. The AMTVR system confirms, with the patient, the date and time provided by the physician's receptionist if different from the date and time specified by the patient, during which the physician's receptionist is placed on hold, and the patient is given the option of the date and time provided by the physician's receptionist or another date and time, which is confirmed with the physician's receptionist. This back-and-forth querying between the patient and physician's office is performed until an agreement is reached between the patient and the physician's office concerning the date and time of the appointment.

In addition, both the patient and the physician's office are asked questions. For example, the patient is asked whether or not the patient needs the physician's office address, phone number, and/or directions to the physician's office. As a further example, the physician's office is asked if they require the patient's insurance identification number, patient's address, patient's phone number, or a reason why the patient needs to see the physician. The AMTVR provides this information as requested from either the patient or the physician's office.

Add Referral to Patient Call Queue Subsystem

Figure 12:
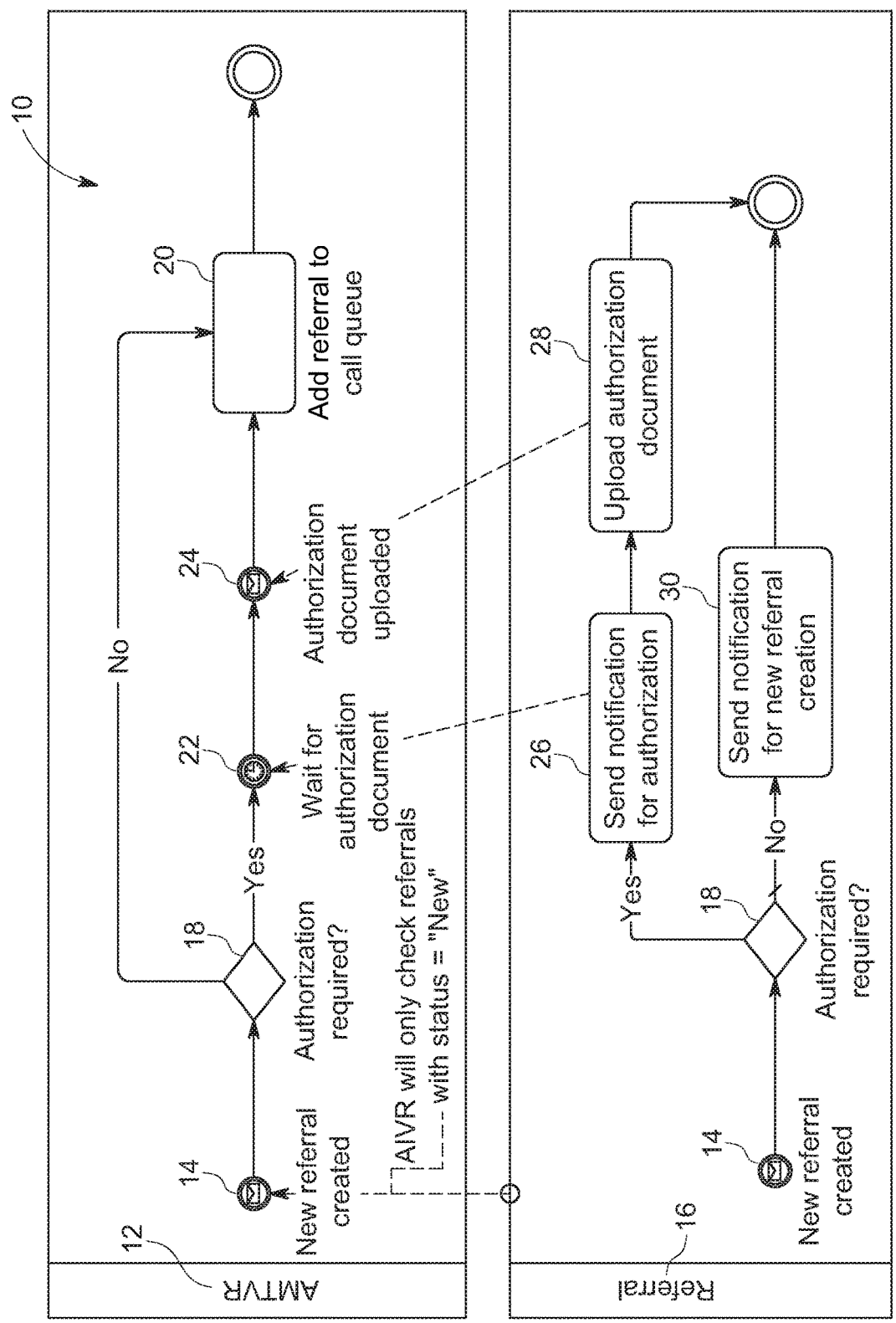
FIG. 12 shows a flowchart of an add referral to patient call queue subsystem incorporated in an appointment tracking and monitoring system.

FIG. 12 shows a flowchart of an add referral to patient call queue subsystem 10, which is incorporated in the AMTVR system 12. If a new referral 14 is added in a referral system 16, the AMTVR system 12 first validates an insurance authorization status regarding a patient associated with the new referral 14 in step 18. If the new referral 14 does not require insurance authorization, the new referral 14 is added to the patient call queue in step 20 by the AMTVR 12, and a notification associated with new referral creation is sent by the referral system 16 in step 30. If the authorization box is checked off within the patient's profile at the physician's office by their staff, this action triggers the transmission of a notification to a referral coordinator to submit a referral authorization request. For example, an email is sent to the referral coordination manager (RCM) at which point the referral is taken out of the automated queue, for the RCM to obtain the necessary authorization. Once obtained, the RCM uploads this authorization number into the software, and the automated process continues for patient contact and referral coordination with the specialist's office. Once the RCM enters the authorization number within the referral management software, this reinitiates the AMTVR to engage with the patient to coordinate the referral appointment.

An authorization is identified by the AMTVR system as it is hard-coded in software based on the patient's insurance. The term "hard-coding" is the software development practice of embedding data directly into the source code of a program or other executable object, as opposed to obtaining the data from external sources or generating it at runtime. Thus, if a referral is requested by the primary care physician, the referral is immediately flagged to go to the referral coordinator if the patient's insurance meets the criteria for requiring an authorization to see the referred specialist. Accordingly, this feature is hard-coded and predetermined.

Once the referral coordinator has obtained an authorization number, and places this number within the referral software, the AMTVR system then, after being triggered to call the patient, schedules an appointment with the specialist at a time when the specialist's office is open.

If the new referral 14 does require insurance authorization, a notification is sent to the RCM by the referral system 16 in step 26 and provided to the AMTVR system 12 in step 22. The notification is, for example, in email format sent directly to the RCM. The RCM assigns the referral to a coordinator to obtain the referral authorization and uploads the document to enable the AMTVR to engage with the patient after the document has been obtained. The referral system 16 uploads an authorization number in step 28, which is received by the AMTVR system 12 in step 24. The new referral 14 is added to the patient call queue in step 20 after the authorization number is obtained and uploaded in steps 22 and 24. The authorization number is an authorization that is obtained may be obtained manually through the patient's insurance company portal by the RCM to show that the primary care provider has referred the patient to see the specific specialist. Insurance companies require that an authorization be obtained prior to the patient's appointment in order to complete the process with the patient and to enable the specialist to be reimbursed for services through utilization of the authorization number. The AMTVR allows the RCM to upload a copy of the authorization in, for example, PDF format to verify the authorization or approval. Once uploaded, the AMTVR sends this authorization to the specialist's office.

Hardware specifications associated with devices used to communicate between and among users of the AMTVR system include, but are not limited to, for example a minimum of 4 MB of RAM and a 10 GB network speed. The AMTVR is HIPAA compliant and has the ability for Internet access to utilize a URL hyperlink to submit referral requests. When a provider is registered to enable their use of the AMTVR, business associate agreement (BAA) and HIPAA forms are required, following which a user name and password are provided to the physician's office to begin referral requests utilizing a secure URL. The business associate agreement (BAA) and HIPAA forms are electronically signed by the primary care provider and stored by the AMTVR system. There are no paper documentation requirements for physicians to be recognized by the AMTVR system.

Exemplary rules concerning the add referral to patient call queue subsystem 10 are provided in Table 27 as follows. Special notes are provided by the primary care provider to assist the specialist in providing the appropriate referral coordination, which includes physical examination and additional diagnostic studies to provide the requesting provider with the necessary referral consultation based on the patient's pathology. These notes may include laboratory findings, radiographic findings, and/or pathology reports, in addition to other specialist's reports. In addition, the primary care provider may add comments concerning the patient's symptoms and their associated presentation, as well as reasons why the primary care provider is requesting a referral from the specialist. These notes are transmitted to the specialist's office by the AMTVR after the referral appointment process. The AMTVR transmits the specialist's office confirmation of the referral appointment along with any notes or documents provided by the primary care physician's office. Notes can also be, but are not limited to, the patient's preference in call time or acknowledgement that the patient has already been scheduled with the appointment date listed. When these special notes are included, the RCM addresses and reviews what the notes indicate to determine the next step in the referral process.

TABLE 27

| Rules Description |
|---|
| If a referral is submitted with special notes, then the referral is marked with a status of pending, and the AMTVR system does not add this referral to the patient call queue |
| The AMTVR system checks referrals having a new status. |
| If a referral does not require an insurance authorization, the referral is added to the patient call queue. |
| If a referral does require an insurance authorization, a notification is sent to the RCM using the referral system. After an authorization number is uploaded to the AMTVR system, the AMTVR system adds the new referral to the patient call queue. |

Exemplary system requirements concerning the add referral to patient call queue subsystem 10 are provided in Table 28 as follows. An authorization required box is a check box provided by the AMTVR and located in the patient's profile, by which the primary care provider's office personnel, who are aware of whether or not the patient requires an authorization for the requested referral, indicate this parameter. If this box is checked by the primary care physician's office upon submission of the referral request, it is provided to the RCM to obtain the authorization number for a variety of methods. The RCM may be required to contact the primary care physician's office for certain medical information pertaining to the specific patient in order to satisfy the insurance company's requirements so that the insurance company can then issue an authorization number associated with the referral.

TABLE 28

| System Requirements Description |
|---|
| The AMTVR system validates the "Authorization Required?" box associated with the patient's insurance plan associated with the submitted referral. Specifically, if the "Authorization Required?" box is checked, the AMTVR system does not call the patient until the authorization number is acquired and uploaded to the AMTVR system. |
| For a referral with the "Authorization Required?" box checked, the referral system sends an email notification to the RCM that instruct the RCM to assign the referral and upload the authorization. |
| For a referral with the "Authorization Required?" box checked, the referral system permits an assigned RCM to upload the authorization number under the "Authorization" section of the referral. This section is a specific area provided by the AMTVR to upload and/or document the authorization number required to complete the requested referral. This area is located in the referral section, and each referral is associated with a different authorization. Documents are uploaded in, for example, PDF format. |
| For a referral with the "Authorization Required?" box checked, the AMTVR system initiates a call to the patient after the authorization file has been uploaded to the AMTVR system. |
| For a referral with the "Authorization Required?" box unchecked, the AMTVR system adds the referral to the call queue and initiates a call to the patient. |
| For a referral that is ready for calling, the AMTVR system fetches the following data from the referral system: referral data; patient data; primary care physician (PCP) and PCP data; and specialist and specialist office data. |
| The AMTVR system initiates a call to a patient within 24 hours for an urgent or stat referral. |
| The AMTVR system initiates a call to a patient within 48 hours for a normal referral. |

Initiate Call to Patient Subsystem

After a referral is validated with a status of ready to call for the patient, the AMTVR system fetches the data and initiates a call to the patient based on the system requirements defined below.

Figure 13:
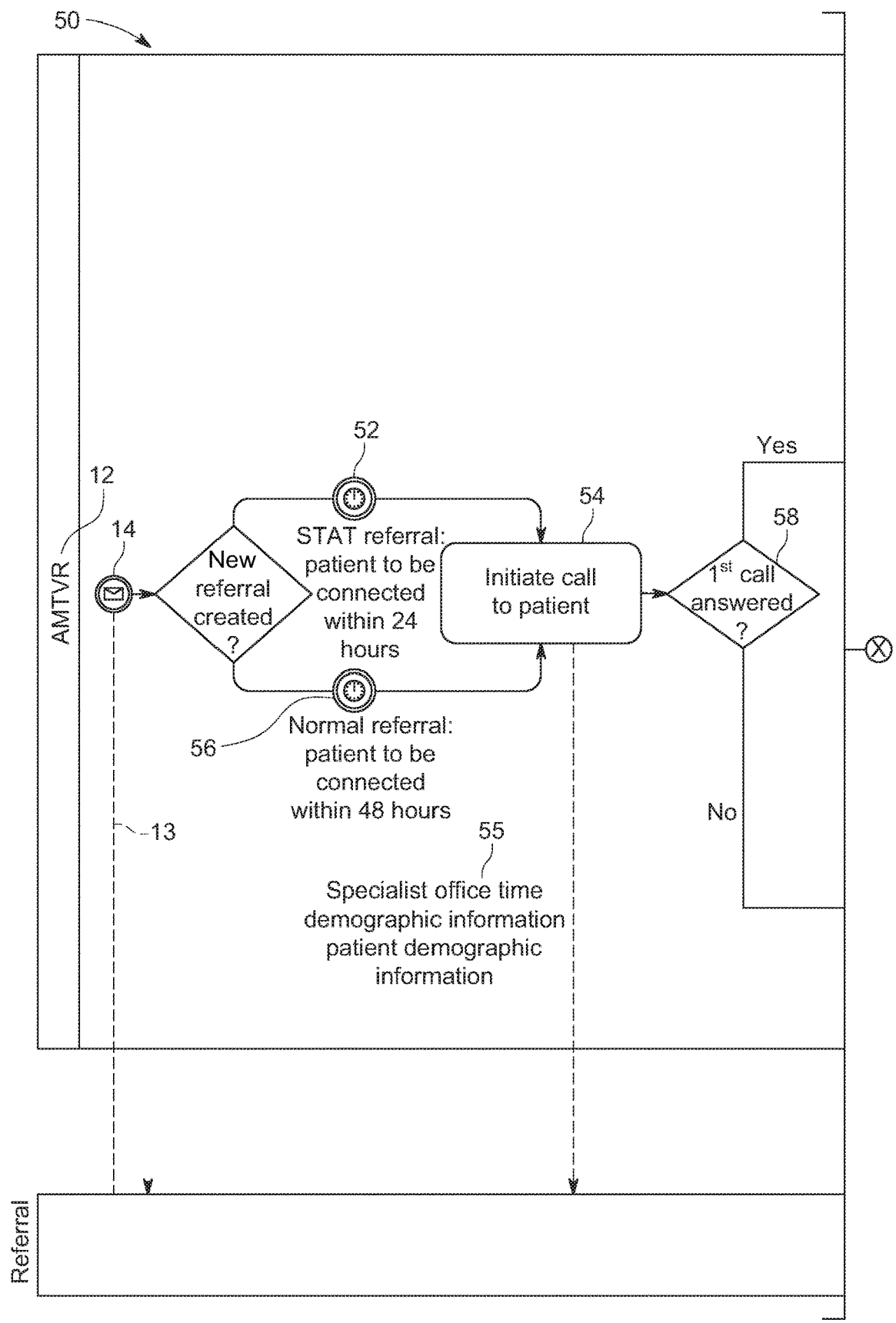
FIG. 13 shows a flowchart of an initiate call to patient subsystem incorporated in the appointment tracking and monitoring system.
Figure 13:
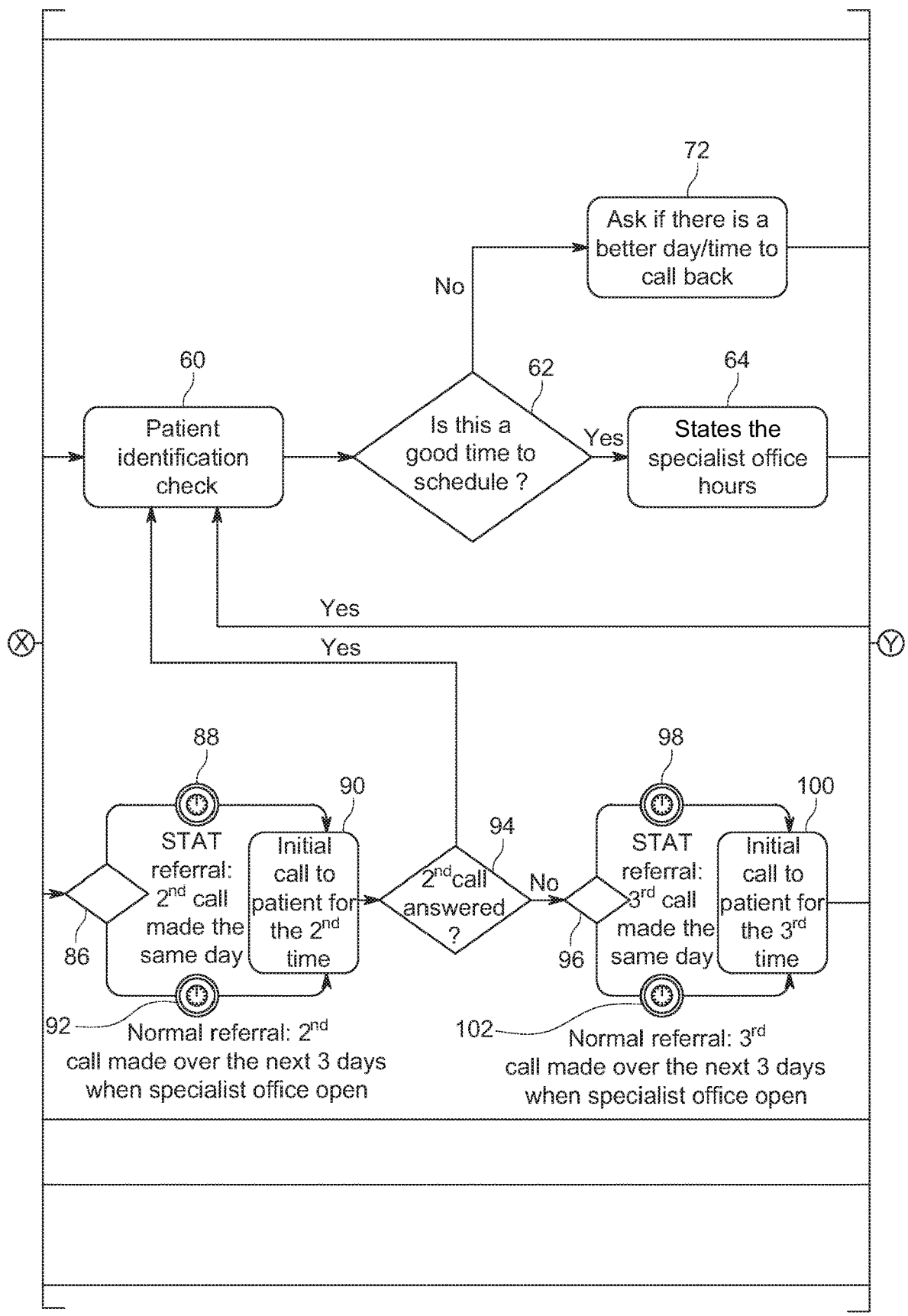
Figure 13:
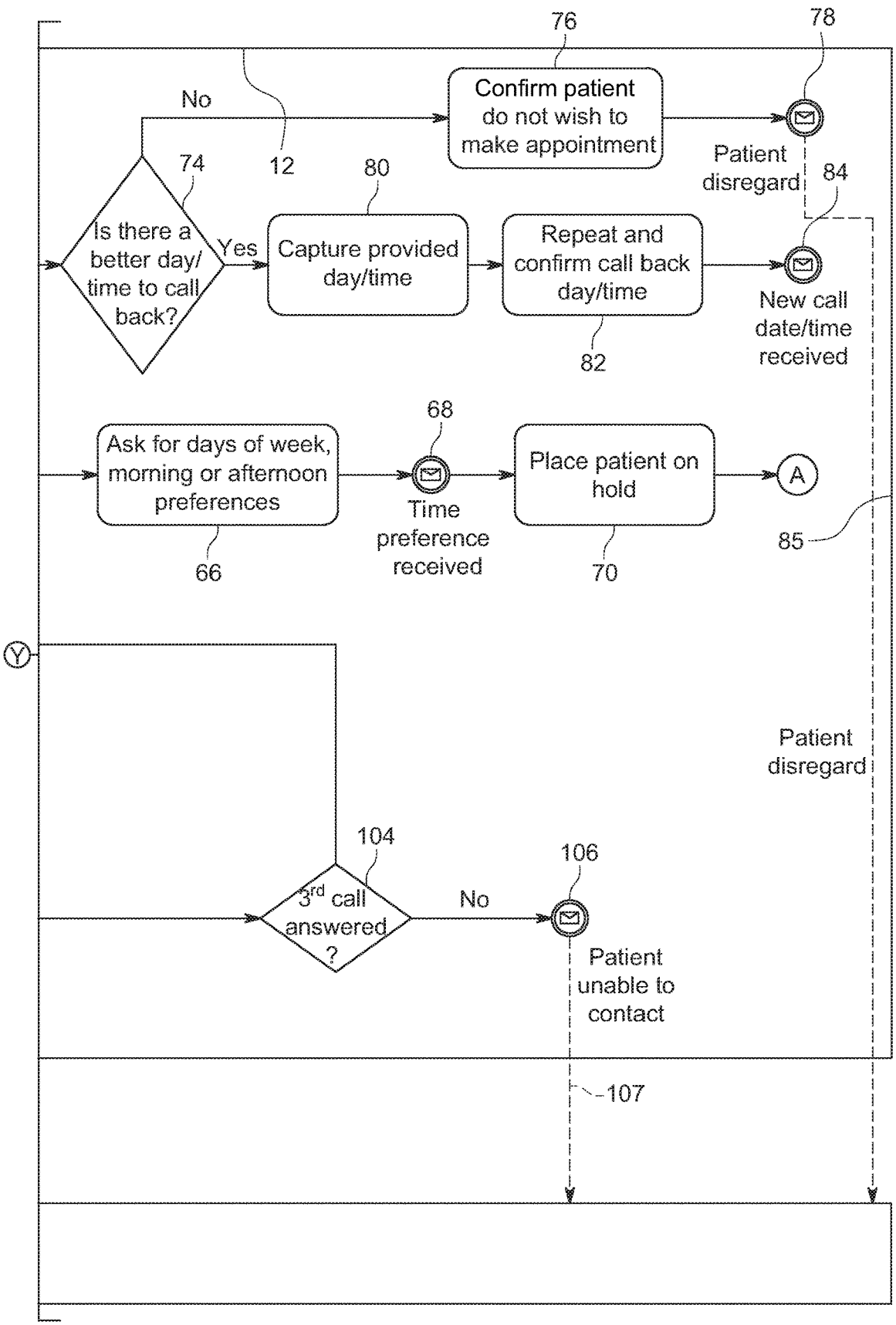

FIG. 13 is a flowchart of an initiate call to patient subsystem 50, which is incorporated in the AMTVR system 12. A new referral creation is initiated 13 by the referral system 16. If the new referral 14 is a stat referral 52, the patient is called in step 54 within 24 hours. However, if the new referral 14 is a normal referral 56, the patient is called in step 54 within 48 hours. Demographic information associated with the specialist's office and patient is provided by the referral system 16 to the AMTVR system 12 in step 55.

If a first call to the patient is answered in step 58, identification of the patient is verified in step 60 before proceeding. If the patient's identity cannot be verified the call is immediately terminated. The AMTVR sends a notification using, for example, email to the referral coordinator to verify the patient's demographics. Once verified by the referral coordinator, the referral coordinator can reinitiate the AMTVR to reengage with the patient to complete scheduling of the referral appointment. The status of the referral changes to "unable to contact" with a sub-status of "DOB not verified". An email is sent to the primary care provider to notify the primary care provider that the patient was not able to verify their date of birth. The primary care provider can then review the patient's profile to make sure that the date of birth is correct and submit a new referral.

Figure 15:
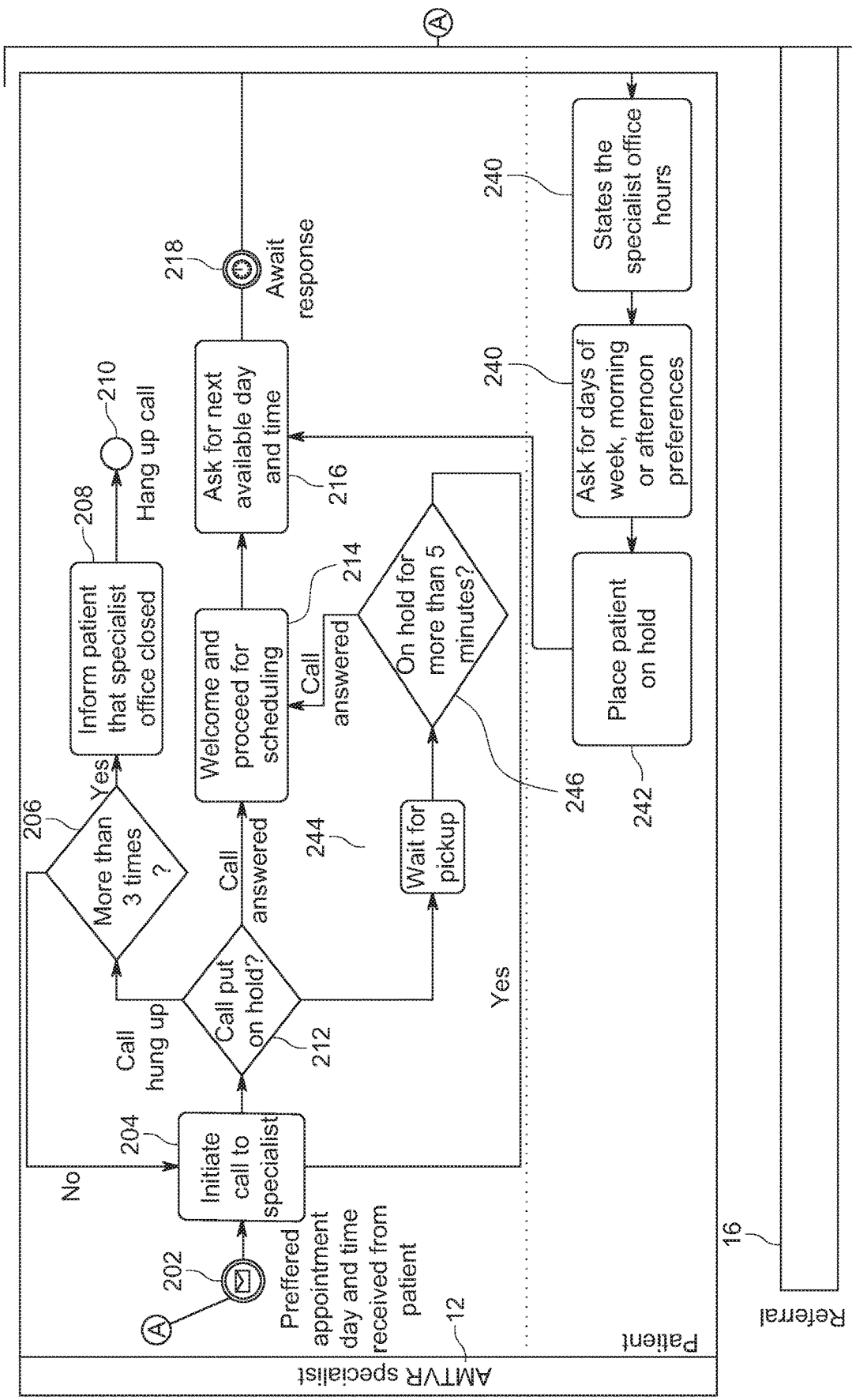
FIG. 15 is a flowchart of a make appointment subsystem incorporated in the appointment tracking and monitoring system.
Figure 15:
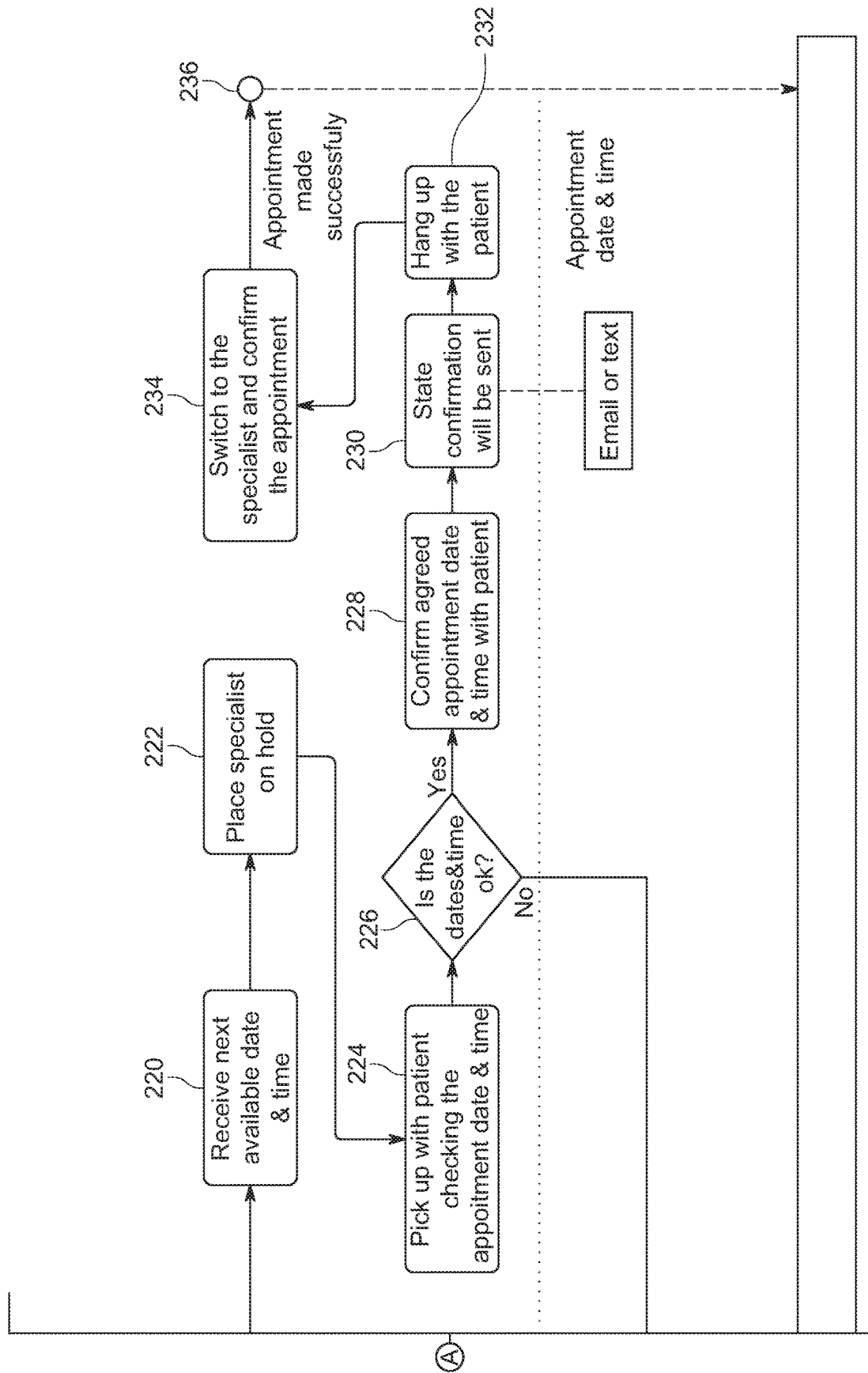

If the patient's identity is verified, the patient is asked whether this is a good time to call in step 62. If so, the specialist's office hours are provided to the patient in step 64, and the patient's appointment preferences, such as, but not limited to, days of the week, times of the day, mornings, and afternoons, are requested in step 66. Upon receipt of the patient's preferences in step 68, the patient is placed on hold in step 70, and the process continues as shown in FIG. 15.

If it is determined in step 62 that it is not a good time to call, the patient is asked if there is a better day and/or time to call the patient back in step 72. If it is determined that there is not a better time to call the patient back in step 74, the patient is asked to confirm that the patient does not wish to make an appointment in step 76. If the patient refuses to make an appointment or refuses the AMTVR services, the AMTVR sends a notification to the primary care provider's office identifying the patient and that the patient refused to make a referral appointment or that the patient could not be reached. In this scenario, the patient's status is changed to "patient disregard". The primary care provider is notified if the referral cannot be initiated. In addition the primary care provider can access this information as well as recording documentation for every referral that was requested by specific primary care providers who have access to only their own patient data.

If so, the patient is disregarded in step 78. If the patient refuses the referral or refuses to coordinate for a referral appointment, the primary care provider is notified by the AMTVR system, the patient's status is changed to "Patient Disregard", and is removed from the patient call queue. Patient's that refuse to make an appointment or cannot be contacted after three (3) attempts are removed from the patient call queue and the PCP is notified by the AMTVR. If it is determined that there is a better time to call the patient back in step 74, that day and time for that call are obtained from the patient in step 80, repeated and confirmed with the patient in step 82, and stored in step 84 and the referral system 16 is notified 85 of this status. If the patient states this is not a good time to make this appointment, the AMTVR requests a better day, date, and/or time to reinitiate a call to the patient. The AMTVR automatically contacts the patient based on the day, date, and/or time requested by the patient. The AMTVR contacts the patient three (3) times to confirm a referral appointment, and notifies the primary care physician if the appointment cannot be confirmed. A text is then sent to the patient indicating that a referral appointment could not be coordinated and that the PCP will be notified. If the patient does not make an appointment thereafter, the patient's referral status is changed to "patient disregard" or "unable to contact".

If the first call to the patient is not answered in step 58 and, it is determined in step 86 that the new referral 14 is a stat referral 88, a second call is made to the patient on the same day in step 90. If it is determined in step 86 that the new referral 14 is a normal referral 92, a second call is made to the patient within the following three days when the specialist's office is open in step 90.

If the second call is answered in step 94, the process proceeds to step 60. If the second call is not answered in step 94, and it is determined in step 96 that the new referral is a stat referral 98, a third call is made to the patient on the same day in step 100. If it is determined in step 96 that the new referral 14 is a normal referral 102, a third call is made to the patient within the following three days when the specialist's office is open in step 100. If the third call is answered in step 104, the process proceeds to step 60. If the third call is not answered in step 104, the referral is marked as "Patient Unable to Contact" in step 106 and the referral system 16 is notified 107 of this status. If the patient is unreachable, the AMTVR transmits a fax and/or email to the PCP and the patient is sent a text message indicating an inability to coordinate a referral request by the PCP, and the referral status is changed to "unable to contact".

Figure 14:
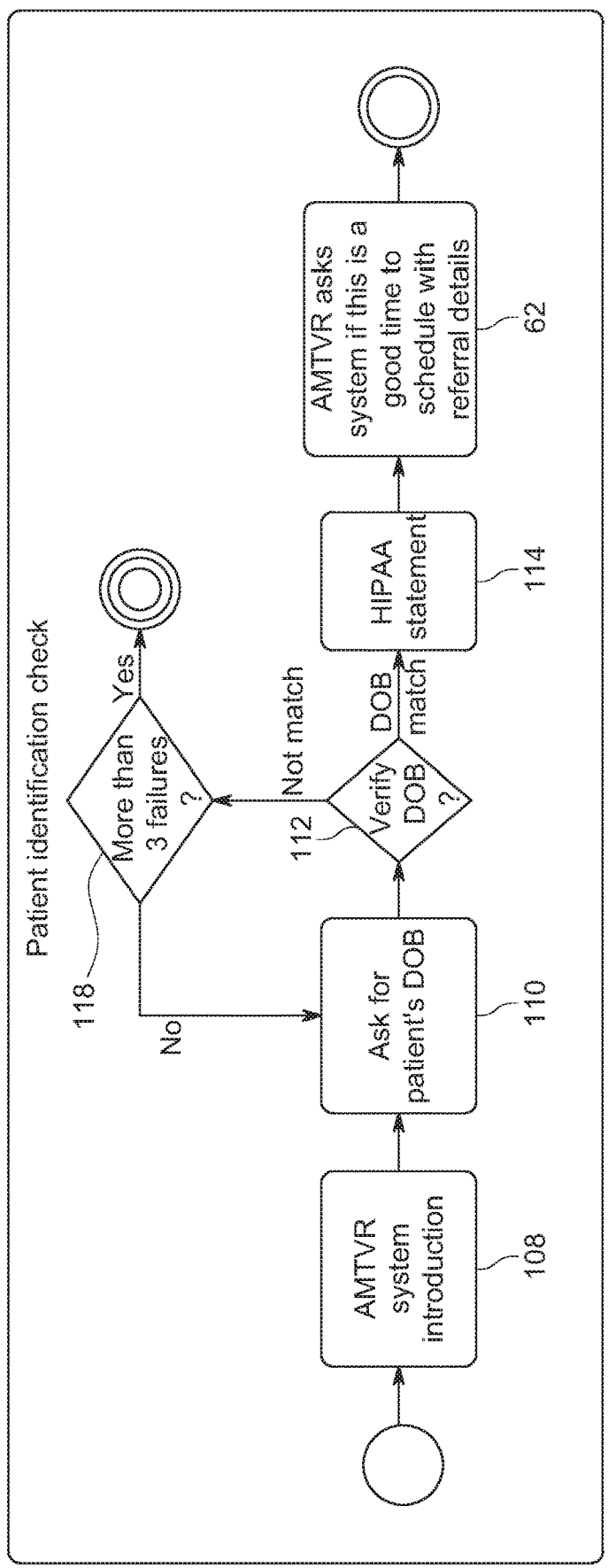
FIG. 14 shows an expanded flowchart providing additional details concerning the flowchart shown in FIG. 13.

FIG. 14 is an expanded flowchart providing additional details concerning step 60 shown in FIG. 13. The initiate call to patient subsystem provides an introduction to the patient in step 108, and asks for the patient's date of birth (DOB) in step 110. If the DOB provided by the patient matches the actual DOB for the patient in step 112, a Health Insurance Portability and Accountability Act (HIPAA) statement is provided to the patient in step 114, and the patient is asked whether this is a good time to schedule the visit in step 62. If so, the process continues with step 64 as shown in FIG. 13. If the DOB provided by the patient does not match the actual DOB for the patient in step 112, the process determines whether the match has failed greater than three (3) times in step 118. If not, the process returns to step 110. If the date of birth cannot be confirmed with the demographic information provided by the PCP's office when the AMTVR contacts the patient, the call is terminated. The AMTVR transmits a message to the referral coordinator to verify the patient's demographic information, especially the date of birth. Once verified or corrected the AMTVR reengages with the patient to schedule an appointment. The patient's status is changed to "unable to contact" with a sub-status of "DOB not verified" and, based on the primary care provider's preference, an email and/or fax is transmitted regarding this status change.

Exemplary rules concerning the initiate call to patient subsystem 50 are provided in Table 29 as follows.

TABLE 29

| Rules Description |
| --- |
| A patient is contacted within 48 hours for a normal referral. A patient is contacted within 24 hours for a STAT referral. If a first call is not answered by the patient, two more calls are made by the AMTVR system. |

TABLE 29-continued

Rules Description

If three calls are not answered by the patient, the referral is marked as "Patient Unable to Contact".
Referral and PCP details are only disclosed after the patient identification is verified.
HIPPA compliance is stated before any call as follows: "This call is being recorded. If you wish this call not to be recorded, please contact us". Call information is retained in accordance with HIPAA requirements Exemplary system requirements concerning the initiate call to patient subsystem 50 are provided in Table 30 as follows.

TABLE 30

System Requirements Description

The AMTVR system initiates a call to a patient within 24 hours for stat referrals. If the specialist's office is not open within 24 hours, the AMTVR system calls at the next opening of the specialist's office.
The AMTVR system initiates a call to a patient within 48 hours for normal referrals. If the specialist's office is not open within the 48 hours, the AMTVR system calls at the next opening of the specialist's office.
If a first call is not answered by the patient, the AMTVR system makes a second call during the next day for stat referrals.
If the first call is not answered, the AMTVR system make the second call within the next three days during the specialist's office hours for normal referrals. If the specialist's office is not open within the next three days, the AMTVR system calls during the next opening of the specialist's office.
If the second call is still not answered, the AMTVR system makes a third call on the same day for stat referrals.
If the second call is not answered, the AMTVR system make the third call within the next three days during the specialist's office hours for normal referrals.
If all three calls are not answered, the AMTVR system updates the referral status to be "Patient Unable to Contact"in the referral system.
The AMTVR system verifies the patient's identification by checking the patient's date of birth (DOB). No information is disclosed before the patient's DOB is matched with the patient's profile as, for example, follows:
"Hi this is Alice from Mednections. We have received a referral from your primary care provider. Before we can provide this information, can you please verify your date of birth in accordance with HIPAA regulations?"
The AMTVR system updates a referral sub-status to "DOB Not Matched" with status "Unable to Contact" if the DOB cannot be matched after three attempts.
Notification is sent to the primary care physician (PCP) if the DOB is not matched.
The AMTVR system reads the specialist's demographic information before calling the patient The AMTVR uses this information to determine when to call the specialist's office based on their office hours as the AMTVR only calls the specialist's office during their office hours. The AMTVR references the name, number, and hours as an example.
The AMTVR system obtains the specialist's office hours associated with the referral, and calls the patient during the specialist's office hours.
The AMTVR system reads the patient's demographic information before calling the patient. The patient's demographic information is used by AMTVR to verify the patient's identity before proceeding with the referral coordination process. The AMTVR references the patient's name and phone number to dial the call.
The AMTVR system reads the patient's' "Preferred Language". The AMTVR system calls the patient in English in phase I. Other language options are not implemented in phase I.
After the patient's identification is verified, the AMTVR system greets the patient and states the reason for the call, including the patient's name, PCP's name, specialist's name and specialty, which are obtained from the referral system.
The AMTVR system responds to phrases received from the patient. After greeting the patient, the AMTVR system asks the patient if this is a good time for the patient to schedule a visit as, for example, follows:
   If the patient answers "Yes" to "a good time to schedule", the AMTVR system continues with scheduling; and
   If the patient answers "No" to "a good time to schedule", the AMTVR system asks for a better date and time to call again.
If the patient answers "Yes"to "a good time to schedule", the AMTVR system states the specialist's office hours, and asks for the patient's preferred day of the week, based on the specialist's office hours, and preferred time, such as morning or afternoon.
The AMTVR system then records the answer received from the patient and relays the preferred day and time to the specialist's office when calling the specialist's office.
The AMTVR system request a preferred day and a preferred time from the patient when scheduling the appointment.
If the patient answers "Yes" to "a good time to schedule" and the day and time preferences are received, the AMTVR system repeats and confirms the received call back date and time, places the patient on hold, and calls the specialist.
If the patient answers "No" to "a good time to schedule", the AMTVR system asks for a new date and time to call the patient again, records the answer received, and checks with the specialist's office hours, for example, as follows:
   1) if the new date and time provided by the patient are not within the specialist's office hours, the AMTVR system asks if the patient would like to schedule an appointment with the specialist on their own; and
   2) if the new date and time provided by the patient are within the specialist's office hours, the AMTVR system records the provided date and time and calls the patient back at the provided time and date.
If the patient answers "No" to "a good time to schedule" and the patient refuses to provide a new date and time to call the patient back, the AMTVR system confirms with the patient that the patient wishes not to make an appointment, and updates the referral status to be "Patient Disregard" in the referral system if confirmed
The AMTVR system repeats the message if no response is received within five seconds. If the patient refuses to make an appointment, the AMTVR informs the patient that the PCP will be notified, the PCP is notified of this refusal to coordinate the requested referral appointment, and if the patient fails to answer in five (5) seconds, the AMTVR repeats the most recent question that was asked.
The AMTVR system stops speaking and listens if the AMTVR system is interrupted by the patient.

In order for the AMTVR system to understand the user's conversational and natural language, exemplary phrases that may be received from users, patients, and the specialist's office personnel and appropriate answers concerning the initiate call to patient subsystem 50 are provided in Table 31 as follows.

TABLE 31

| Phrase from | Possible Phrases | AMTVR System Answer | System Requirement |
|---|---|---|---|
| | | Initiate Call to Patient Subsystem Workflow | |
| Patient | Who are you? | This is Alice, I am calling from a referral service called "Mednections"- Dr. [PCP name] your primary care provider, has asked us to contact you in order to schedule | AMTVR is able to respond back with PCP's name, specialist same and specialty of the referral. |

TABLE 31-continued

Initiate Call to Patient Subsystem Workflow

| Phrase from | Possible Phrases | AMTVR System Answer | System Requirement |
|---|---|---|---|
| | | you an appointment with Dr. [specialist name] a [specialty]. This request was generated on your last visit with Dr. [PCP name]. | |
| Patient | Who are you? (for the 2nd time) | Hi this is Alice; I am calling from Mednections. We are Dr. [PCP name] referral service. | |
| Patient | Do you have my referral? | Yes. I am calling from a referral service called "Mednections". Dr. [PCP name], your primary care provider, has asked us to contact you in order to schedule your appointment with Dr. [specialist name] a [specialty]. This request was generated on your last visit with Dr. [PCP name]. | |
| Patient | What is this for? | Dr. [PCP name], your primary care provider, has asked me to contact you in order to schedule your appointment with Dr. [specialist name] a [specialty]. | |
| Patient | How did you get my phone number? | From your primary provider, Dr. [PCP]. | |
| Patient | Why have I not been called yet to schedule my appointment? | 1) If the AMTVR system called previously, the AMTVR system should respond back with the calling date and time: I called you before on [date] [time]. Can we schedule it now? 2) If this is the first time the AMTVR system called, the AMTVR system should response: I just received the [referral xx] from [XXX], can we schedule it now? | System shall be able to check the calling history for this Referral and respond. If the AMTVR system called previously, the AMTVR system should respond back with the calling date and time: I called you before on [date] [time]. Can we schedule it now? If this is the first time the AMTVR system called, the AMTVR system should response: I just received the [referral xx] from [XXX], can we schedule it now? AMTVR shall be able to respond back with a referral ID and the PCP's name of the referral. |
| Patient | Where are you located? | We are a business associate with the [PCP office location]. | System shall be able to fetch the PCP's office location of the referral and respond back. |
| Patient | My doctor didn't tell me about this referral | Your PCP, Dr. [PCP name], has referred you to this specialist, Dr. [specialist name], specialty on [refer to submission of referral date]. Can we schedule your appointment right now? | 1) Patient is "OK" to continue 2) Patient is NOT "OK" to continue, AMTVR updates the Referral to be "Patient Disregard". AMTVR shall NOT be able to capture different reasons for "Patient Disregard". |
| Patient | Why does my PCP have a Referral Service? | Your PCP, Dr. [PCP name], provides this service to better serve their patients in assisting with scheduling specialty appointments. Can we schedule your appointment right now? | 1) Patient is "OK" to continue 2) Patient is NOT "OK" to continue, AMTVR updates the Referral to be "Patient Disregard". AMTVR shall not be able to capture different reasons for "Patient Disregard". |
| Patient | Why did my PCP refer me? | Your PCP, Dr. [PCP name], has referred you to this specialist, Dr. [specialist name], specialty on [refer to submission of referral date]. If you have any questions regarding this referral, please contact your PCP, Dr. [PCP name]. | 1) Patient is "OK" to continue Patient is NOT "OK" to continue, AMTVR updates the Referral to be "Patient Disregard". AMTVR shall not be able to capture different reasons for "Patient Disregard". |
| Patient | Please stop calling me | Thank you for your time to take this call, I will notify Dr. [PCP name] that you would like to disregard this referral. | AMTVR shall update the Referral to be "Patient Disregard". Referral system sends daily reports to PCP for "Patient Disregard" referrals. |

TABLE 31-continued

Initiate Call to Patient Subsystem Workflow

| Phrase from | Possible Phrases | AMTVR System Answer | System Requirement |
|---|---|---|---|
| Patient | I do not want this referral | Thank you for your time to take this call, I will notify Dr. [PCP name] that you would like to disregard this referral. | AMTVR shall update the referral to be "Patient Disregard". The referral system sends daily reports to PCP for "Patient Disregard" referrals. The AMTVR will not be able to capture patient's disregard reasons. |
| Patient | I don't schedule my own appointments; can I give you family members number to call? | Dr. [PCP name] your primary care provider, has asked me to contact you in order to schedule your appointment with Dr. [specialist's name] a [specialty]. | AMTVR marks the Referral as "Patient Disregard", if patient hangs up. |
| Patient | May I speak to another person? | Yes, however, Dr. [PCP name] highly recommends that we assist in scheduling now so that we can ensure that all of your appointments are scheduled in a timely manner. We will also report back to Dr. [PCP name] with your appointment status. | AMTVR marks the Referral as "Patient Disregard" if the patient still refuses to talk to AMTVR for appointment or hangs up the call. |
| Patient | I need to speak to my doctor first before scheduling | That is perfectly fine, can I call you in a few days to help schedule the appointment? | AMTVR places the referral back to the patient call queue and calls the patient again [X] days later. AMTVR shall not be able to capture different reasons for "Patient Disregard". |
| Patient | I don't remember this (no one told me) | Your PCP Dr. [PCP name] has referred you over to this specialist Dr. [Specialist name] specialty on [refer to submission of referral date]. Can we schedule your appointment right now? | 1) Patient is "OK" to continue 2) Patient is NOT "OK" to continue, AMTVR updates the Referral to be "Patient Disregard". AMTVR shall NOT be able to capture different reasons for "Patient Disregard". |
| Patient | Can I schedule on my own? | Yes, however, Dr. [PCP Name] highly recommends us to assist in scheduling right now that way we can make sure all of your appointments are scheduled in a timely manner. We also will report back to Dr. [PCP name] with your appointment status. If Patient still refuse schedule with AMTVR. AMTVR will response: Okay I understand that you would like to schedule on your own, here is the specialist information, are you ready to jot it down? | After AMTVR's initial response to "Can I schedule my own?", the patient may have two different responses: 1) Patient is ok to continue with AMTVR schedule. System follows the "Make Appointment" workflow 2) Patient refuses to schedule with AMTVR. AMTVR provides the specialist's name and phone number, and then calls the specialist [X] days later for three (3) times trying to get the scheduled date and time: if an appointment date and time is confirmed, AMTVR feeds the date & time back to the referral system and marks the Referral as "Scheduled & Confirmed"; otherwise, AMTVR marks the Referral as "Patient Disregard". |
| Patient | Can you find a place closer to my home? zip code? | I understand you would like to find a specialist closer to your home, however Dr. [PCP name] highly recommends that you see this specialist, Dr. [specialist name]. | 1) Patient is "OK" to continue 2) Patient is not "OK" to continue, AMTVR responds with "I will notify your PCP Dr. [PCP name] regarding this information, we will be contacting you when a new referral comes in." and AMTVR updates the referral to be "Patient Disregard". AMTVR shall not be able to capture different reasons for "Patient Disregard". |
| Patient | I can't find anybody that accepts my insurance. | I apologize that you are having a hard time finding a specialist, however, based on our records, Dr. [specialist name] does accept your insurance. Would you like me to call | 1) Patient is "OK" to continue 2) Patient is NOT "OK" to continue, AMTVR will response "I will notify your |

TABLE 31-continued

| Phrase from | Possible Phrases | AMTVR System Answer | System Requirement |
|---|---|---|---|
| | | Initiate Call to Patient Subsystem Workflow | |
| | | and schedule an appointment with Dr. [specialist name] This should not be an issue as the AMTVR filters specialists by the insurance that the specialists accept. | PCP Dr. [PCP name] regarding this information, we will be contacting you when a new referral comes in." and AMTVR will update the Referral to be "Patient Disregard". AMTVR shall not be able to capture different reasons for "Patient Disregard". |
| Patient | The specialist stated they do not accept my insurance. | I apologize that you are having a hard time with this specialist, however, based on our records, Dr. [specialist name] does accept your insurance. Would you like me to call and schedule an appointment with Dr. [specialist name] and verify that they accept your insurance. This should not be an issue as the AMTVR filters specialists by the insurance that the specialists accept. | AMTVR will update the referral to be "Patient Disregard". AMTVR shall NOT be able to capture different reasons for "Patient Disregard". |
| Patient | Do they treat (part of body)? | Let's connect with the specialist so we can schedule your appointment. | |
| Patient | What kind of specialist is this? | Dr. [specialist name] is a [specialty]. | AMTVR will respond with the specialist's specialty. |
| Patient | Can I have the specialist's phone number? | I can provide you with the specialist's number to find this information. | AMTVR will provide specialist's office telephone number. |
| Patient | Is there a waiting list? | That is a great question, let's contact the specialist's office to find out the soonest appointment they have for you. I am calling now to make an appointment for you. | AMTVR will continue with making the appointment. |
| Patient | Do they work weekends? | Their office hours are [specialist's office hours]. | AMTVR will respond with the specialist's office hours. |
| Patient | What is address to my appointment? | The address is [specialist's office address]. | AMTVR will respond with the specialist's office location. |
| Patient | Is there a bus line close to the specialist's location? Which one? | I can provide you with the specialist's telephone number to find this information. | AMTVR would not be able to answer this kind of question, but AMTVR will respond with the specialist's office phone number. |
| Patient | I have already scheduled | That is great! Can you provide me with the time and date of the appointment? Please confirm it is with Dr. [Specialist name] at this location [specialist location]. | AMTVR shall be able to record the scheduled date and time and feed the date and time back to the referral system, with status as "Scheduled" and "Confirmed". |

Make Appointment Subsystem

Upon receiving the patient's preferences for the day and time of the specialist's appointment from step 68 shown in FIG. 13, the AMTVR system initiates a call to the specialist's office indicated in the new referral in a make appointment subsystem.

FIG. 15 is a flowchart of the make appointment subsystem 200. The patient's preferred appointment time and day 202 received from the initiate call to patient subsystem 50 are used to initiate a call to the specialist 204. If the call is determined as being hung up in step 212, another call to the specialist is initiated in step 204. If the call is determined as being hung up greater than three (3) times in step 206, the patient is informed that the specialist's office is closed in step 208, and the call to the patient is hung up in step 210. The patient is notified by the AMTVR that the specialist's office is unable to make an appointment at this time. The patient will be contacted again within 24 hours to reengage during the specialist's office hours to reinitiate a referral appointment.

If the call is determined to be answered by the specialist's office in step 212, a welcome greeting is provided to the specialist's office and scheduling is begun in step 214. The specialist's office is asked for the next available date and time for an appointment in step 216, following which a response is awaited in step 218. The next available date and time for an appointment is received in step 220, and the specialist's office is placed on hold in step 222. The patient is asked if the next available date and time for an appointment is acceptable in step 224, and if the next available date and time for an appointment is determined to be acceptable to the patient in step 226, the patient is told that a confirmation will be sent to the patient in step 230. The call with the patient is terminated in step 232, the call is switched to the specialist's office in step 234 to confirm the appointment in step 234, and the appointment is successfully scheduled in step 236. However, if the next available date and time for an appointment is determined not to be acceptable to the patient in step 226, the patient is provided with the specialist's office hours in step 238, and is asked for the patient's preferences regarding days of the week and time of day, such as but not limited to mornings or afternoons in step 240. The patient is asked to please hold until the appointment has been confirmed, following which the patient is placed on hold in step 242, and the process returns to step 216 to ask for the specialist's office next available date and time. Once the appointment is confirmed, the patient can hang up at any time.

If the call is determined to be placed on hold by the specialist's office in step 212, the make appointment subsystem waits for the specialist's office to pick up in step 244. If the call is determined to have been on hold for greater than five (5) minutes in step 246, the AMTVR system responds back to the patient by indicating that the specialist's office is too busy at this time, and that the patient will be called back at another time to schedule their appointment. The call is then terminated and re-initiated in step 204. If the call is answered in five (5) minutes or less, the process provides a welcome greeting and proceeds with scheduling in step 214

Figure 15A:
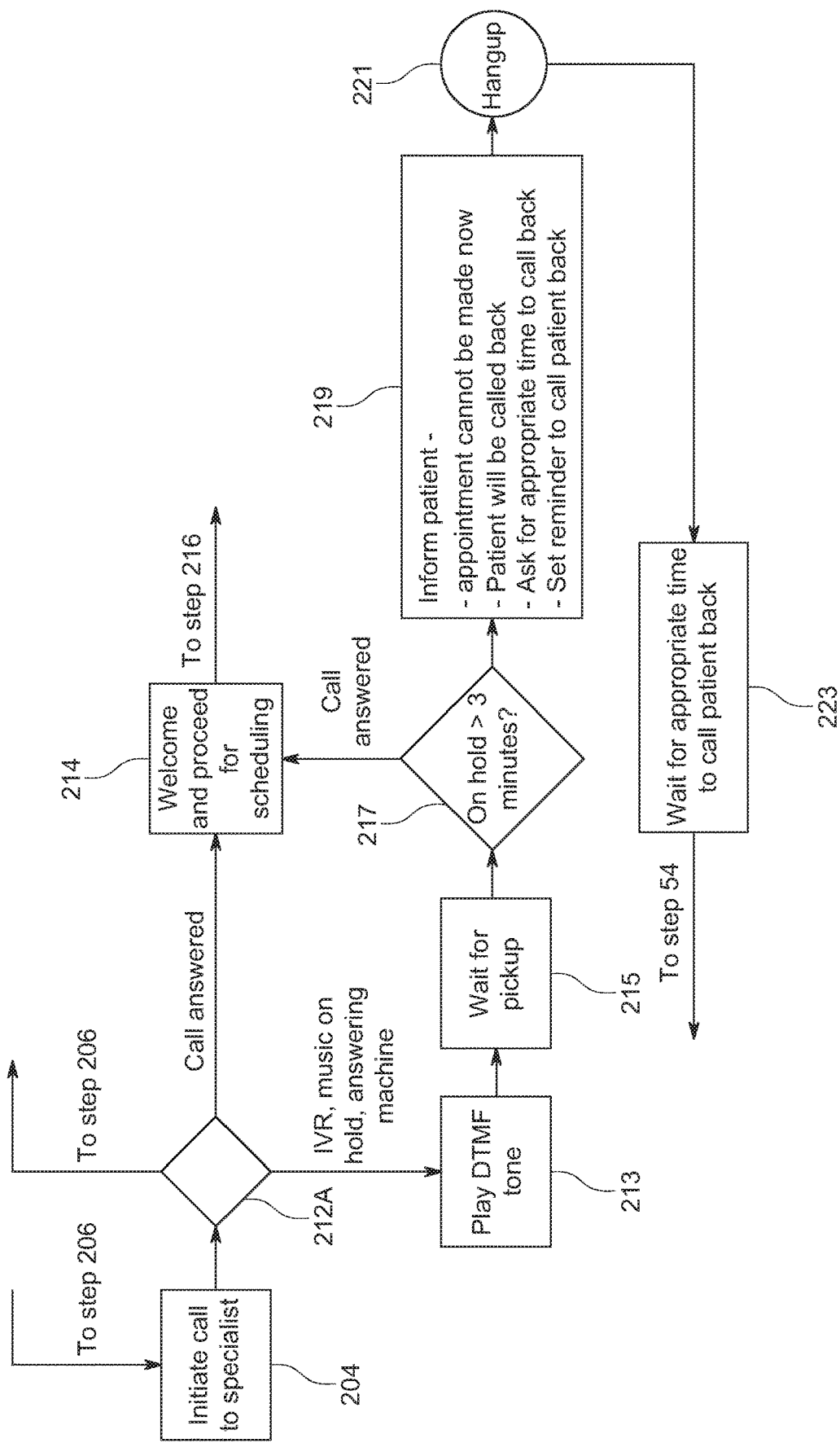
FIG. 15A is a flowchart showing an another embodiment of a portion of the process shown in FIG. 15 concerning steps 212, 244, and 246.

FIG. 15A shows an alternative embodiment concerning steps 212, 244, and 246 shown in FIG. 15. In response to the AMTVR interfacing with an interactive voice response (IVR) system, music on hold, and/or answering machine in step 212A when, for example, calling the specialist's office, a dual-tone multi-frequency (DTMF) tone generator generates a tone in step 213. The tone corresponds to, for example 0, 1, and/or 9, which represents one or more digital tones associated with access to, for example, an operator, front desk, and/or receptionist, in an attempt to thereby establish a human connection. If there is still no response after waiting in step 215 a predetermined time period, such as but not limited to three (3) minutes, in step 217, the AMTVR system informs the patient that an appointment cannot be made at this time, that the patient will be called back, asks the patient for an appropriate time to call back, and sets a reminder to call the patient back at the appropriate time in step 219. The AMTVR system then terminates the call with the patient in step 221, waits for the appropriate time to call the patient back in step 223, and returns to step 54 as shown in FIG. 13 thereafter. If the call is answered in step 217, the process proceeds with step 214, as is also shown in FIG. 15.

Exemplary rules concerning the make appointment subsystem 200 are provided in Table 32 as follows.

TABLE 32

| Rules Description |
|---|
| If the specialist places the AMTVR system on hold, the AMTVR system waits for three (3) minutes. If the specialist still does not answer, the AMTVR system tells the patient that it is unable to connect to the specialist and asks for a better time to call the patient back. |
| If the specialist picks up the call, but does not answer, the AMTVR system waits for three (3) minutes. If there is still no answer, the AMTVR system tells the patient that it is unable to connect to the specialist and asks for a better time to call the patient back. |
| If the specialist does not pick up the call, the AMTVR tries three (3) times. If there is still no answer, the AMTVR system tells the patient that it is unable to connect to the specialist and asks for a better time to call the patient back. |
| If the specialist hangs up, the AMTVR system tries three (3) times. If there is still no answer, the AMTVR system tells the patient that it is unable to connect to the specialist and asks for a better time to call the patient back. |

Exemplary system requirements concerning the make appointment subsystem 200 are provided in Table 33 as follows.

TABLE 33

| System Requirements Description |
|---|
| The AMTVR system places one person on hold, and calls/speaks with another person. |
| While waiting on hold, the AMTVR system tells the patient that we are on hold with the specialist, for example, as follows: "Thank you for holding, I am on the other line trying to connect with the specialist, their wait time is a bit longer than expected." |
| The AMTVR system waits for no more than three (3) minutes, if put on hold by the specialist. Otherwise, the AMTVR system calls again. |
| The AMTVR system calls no more than three (3) times if the specialist hangs up. |
| The AMTVR system calls no more than three (3) times if put on hold for more than three minutes. |
| After three (3) failed attempts to call the specialist, the AMTVR responds to the patient by stating "the appointment cannot be made at this time, what is a good time for me to call you back?", which follows the "Ask if there is a better time to call back" workflow. |
| When the call is answered by the specialist's office, the AMTVR system provides a greeting and states the reason for calling, including the patient's name, PCP's name, specialist's name and specialty, which are fetched from the referral system. |
| The AMTVR system relays the patient's preferred day of week and time (e.g., morning or afternoon) to the specialist while asking for the next availability. |
| The AMTVR system records the specialist's provided date and time. |
| The AMTVR system relays the specialist's provided date and time to the patient. |
| If the patient answers "Yes" to the specialist's provided date and time, the AMTVR system states that the appointment confirmation will be sent with a predefined communication preference (e.g., email or text). |
| The referral system sends an appointment confirmation to the patient based on the predefined communication preference (e.g., email or text). |
| The AMTVR system does not change the communication preference with new email or mobile number to be entered. |
| If the patient answers "Yes" to the specialist's provided date and time, the AMTVR confirms and hangs up with the patient. |

TABLE 33-continued

System Requirements Description

If the patient answers "Yes" to the specialist's provided date and time, the AMTVR system confirms and hangs up with the specialist.
The AMTVR system updates the confirmed date and time and updates the referral status to be "Scheduled & Confirmed" to the referral system.
If the patient answers "No" to the specialist's provided date and time, the AMTVR states the specialist's office hours and asks for the patient's preferred day and time again.
If the patient answers "No" to the specialist's provided date and time for the third time, the AMTVR system updates the referral status as "Patient Disregard".
All conversations are recorded.

In order for the AMTVR system to understand the user's conversational and natural language, exemplary phrases that may be received from users, patients, and the specialist's office personnel and appropriate answers concerning the make appointment subsystem 200 are provided in Table 34 as follows.

TABLE 34

Make Appointment Subsystem Workflow

| Phrase from | Possible Phrases | AMTVR System Answer | System Requirement |
|---|---|---|---|
| Patient | That time does not work for me? | This is the soonest appointment, if this does not work for you, please let me know your preferred days of week, and preference of morning or afternoon. I will check with the specialist. | AMTVR should address this as the soonest appointment that is available from the specialist based on his/her preference. System should be able to try to schedule the appointment three (3) times between the patient and specialist. AMTVR shall mark the referral as "Patient Disregard" after three (3) failures. |
| Patient | The specialist stated they do not accept my insurance | I will notify your PCP, Dr. [PCP name], regarding this information, we will be contacting you when a new referral comes in with a different specialist that accepts your insurance. | AMTVR will update the referral to be "Patient Disregard". AMTVR shall not be able to capture different reasons for "Patient Disregard". |
| Specialist | Does the patient have a referral? | Yes, the patient has been referred from Dr. [PCP name], I have a referral here for patient [patient name]. | System shall be able to respond with PCP's name and patient name of the referral. |
| Specialist | Which PCP office are you calling from? | I am calling on behalf of Dr. [PCP name] office. | |
| Specialist | Who are you? | I am calling on behalf of Dr. [PCP name] office. We are the primary care referral service. | |
| Specialist | Where are you calling from? | | |
| Specialist | Do you have clinical docs for the patient? | Please contact Dr. [PCP name] for the information, here is the phone number [PCP number]. | AMTVR will not be able to reference uploaded documents. AMTVR will respond to ask to contact PCP, with PCP's office number provided. |
| Specialist | Do you have the authorization for the patient? | Yes, authorization has been obtained. I will fax over once we schedule an appointment. | |
| Specialist | We do not accept that insurance | Thank you for this information, we will contact the patient's PCP regarding this and update our system. | AMTVR will update the Referral to be "Patient Disregard". AMTVR shall NOT be able to capture different reasons for "Patient Disregard". |
| Specialist | What insurance does the patient have? | Patient has [refer to patient profile]. | AMTVR will respond back with the Patient's insurance information. |
| Specialist | Do you have the authorization for the patient? | Yes, I will send this over after the appointment has been scheduled | After the appointment is scheduled, the referral system will send the authorization. |
| Specialist | Why does the patient need to be seen? | According to the notes, Dr. [PCP name] has listed this diagnosis code [Dx] as the reason why patient is being referred. | AMTVR will respond with the diagnosis code from the referral. |
| Specialist | What part of the body is the patient having pain? | According to the notes, Dr. [PCP name] has listed this diagnosis code [Dx] as the reason why patient is being referred. | AMTVR will respond with the diagnosis code from the referral. |
| Specialist | What kind of testing is the patient being referred for? | According to the notes, Dr. [PCP name] has listed this diagnosis code [Dx] as the reason why patient is being referred. | AMTVR will respond with the diagnosis code from the referral. |

TABLE 34-continued

| Phrase from | Possible Phrases | AMTVR System Answer | System Requirement |
|---|---|---|---|
| | | Make Appointment Subsystem Workflow | |
| Specialist | Do you know what plan they have? | According to the patient's profile, insurance plan is listed as [insurance plan] | AMTVR will respond with the patient's insurance information. |
| Specialist | What insurance does the patient have? | Patient [name] has [insurance]. | AMTVR will respond with the Patient's insurance information. |
| Specialist | Who is the patient's PCP? | Patient's PCP is Dr. [PCP name]. | AMTVR will respond with the PCP's name. |
| Specialist | What are the patient's details (e.g., name, address, DOB, insurance) to schedule appointment? | Please refer to the patient's profile for this information. | AMTVR will respond back with the patient's basic information. |
| Specialist | What language does patient speak? | Patient speaks [refer back to language on patient's profile]. | AMTVR will respond with the patient's preferred language from the patient's profile. |
| Specialist | What is the diagnosis code? | According to the notes, Dr. [PCP name] has listed this diagnosis code as the reason why patient is being referred. | AMTVR will respond with the diagnosis code from the referral. |
| Specialist | What procedure are you requesting? | According to the notes, Dr. [PCP name] has listed this diagnosis code as the reason why patient is being referred. | AMTVR will respond with the diagnosis code from the referral. |
| Specialist | The patient needs to bring in their labs, clinical docs, bloodwork, etc. | Yes, I will notify the patient to come 15 minutes early and bring their insurance card. If you need any additional information, please contact the patient's PCP, Dr. [PCP name], regarding your request for those items. | AMTVR will play a generic dialog to patient at the end of the call, referencing date, time, location, specialist's name and reminder of these items. |
| Specialist | Make sure the patient comes in 15 minutes before the appointment | Yes, I will notify the patient to come 15 minutes early and bring their insurance card. | AMTVR will play a generic dialog to the patient at the end of the call, referencing the date, time, location, specialist's name, and a reminder of these items. |
| Specialist | Have them bring their insurance card | Yes, I will notify the patient to come 15 minutes early and bring their insurance card. | AMTVR will play a generic dialog to the patient at the end of the call, referencing the date, time, location, specialist's name, and a reminder of these items. |
| Specialist | Can a script be sent out? | Yes, after the appointment has been scheduled, our system will send an automated fax to fax number [specialist's fax number]. | |
| Patient | Can you email or text me my appointment details? | At the end of the referral call, the patient is instructed that they will be notified prior to the appointment date with a text notification. This is initiated from the information received during confirmation with the patient that the appointment has been scheduled utilizing the AMTVR in cooperation with the referral system. Based on the patient's profile and selected communication preference integrated into the system prior to the call. The patient will have either an email or text message as default, the AMTVR cannot add or change the patient's preference since this is handled by the PCP's office or the referral coordinator. | AMTVR will be able to send appointment confirmation to a predefined communication preference (e.g., email or text), but will not be able to update communication preference data. CR has been made to referral system that at least one of them is required - Email or Mobile Phone number. |
| Patient | How do I get a copy of my authorization and/or referral? | | AMTVR will only be able to send authorization file to predefined communication preference (e.g., email or text, but will not be able to update the communication preference data. |

Confirm Appointment with Specialist Subsystem

If the patient would like to schedule their appointment on their own, the AMTVR system calls the specialist's office [X] days later to confirm that the appointment associated with the referral was made. The AMTVR platform then feeds the date and time of the appointment back to the referral and updates the referral status to be "Scheduled & Confirmed".

Exemplary rules concerning the confirm appointment with specialist subsystem are provided in Table 35 as follows.

TABLE 35

| Rules Description |
| --- |
| The AMTVR confirms the specialist appointment made by the patient. |

Exemplary system requirements concerning the confirm appointment with specialist subsystem are provided in Table 36 as follows.

TABLE 36

| System Requirements Description |
| --- |
| The AMTVR system provides the specialist's name, phone number, address, and office hours of the referral if the patient insists on scheduling their own appointment. |
| The AMTVR system flags the referral as "Schedule confirmation needed from the Specialist", if the patient insists on scheduling their own appointment |
| The AMTVR system calls the specialist [X] days after the call with the patient who insists on scheduling their own appointment. |
| The AMTVR system calls the specialist twice times to obtain the scheduled date and time. Otherwise, the referral is marked as "Patient Disregard" after two failures. |
| The AMTVR system calls the specialist [X] days after the previous failure. |
| The AMTVR system feeds the scheduled date and time into the referral system and marks the referral as "Scheduled & Confirmed". |

In order for the AMTVR system to understand the user's conversational and natural language, exemplary phrases that may be received from users, patients, and the specialist's office personnel and appropriate answers concerning the confirm appointment with specialist subsystem are provided in Table 37 as follows.

TABLE 37

| Phrase from | Possible Phrases | AMTVR System Answer | System Requirement |
| --- | --- | --- | --- |
| | | Confirm appointment with Specialist Subsystem Workflow | |
| Patient | Can I schedule on my own? | | After AMTVR's initial response to "Can I schedule my own?", the patient may have two different responses: Patient is ok to continue with AMTVR schedule. AMTVR will follow the make appointment workflow Patient refuses to schedule with the AMTVR. AMTVR will provide the specialist's name and phone number, and then call the specialist [X] days later for three (3) times trying to get the scheduled date and time. If an appointment date and time is confirmed, the AMTVR will provide the date and time to the referral system and mark the referral as "Scheduled & Confirmed"; otherwise, the AMTVR will mark the referral as "Patient Disregard". |
| Specialist | What are you calling for? | | AMTVR shall respond with the patient's and specialist's names. |
| Specialist | What is the date of birth of the patient? | | AMTVR shall respond with the patient's date of birth provided in the patient's profile. |
| Specialist | 1) Yes, looks like they are scheduled | | AMTVR shall be able to provide the appointment date and time to the referral |

TABLE 37-continued

| Phrase from | Possible Phrases | AMTVR System Answer | System Requirement |
|---|---|---|---|
| | | Confirm appointment with Specialist Subsystem Workflow | |
| | for _(date/time) _or they have already seen the specialist on (date/time) | | system and update the status to "Scheduled & Confirmed". |
| Specialist | 2) No, the patient has not scheduled an appointment. | | AMTVR shall call back in [X] days. AMTVR will call three (3) times if the appointment is not scheduled. AMTVR shall update the referral to be "Patient Disregard" after three (3) calls. |

Feed Data Back to Referral System

This section is designed to list all scenarios that data will be fed back to the referral system: after triggers sent by the AMTVR application, the Referral platform will update.

Exemplary system requirements concerning the feed data back to referral system are provided in Table 38 as follows.

TABLE 38

| System Requirements Description |
|---|
| The AMTVR system makes no more than three (3) calls to the patient. If all three (3) calls are not answered, the AMTVR system updates the referral status to be "Patient Unable to Contact" in the referral system. |
| For the last (third) time, the AMTVR system calls the patient who has not answered and the AMTVR system leaves the following message: "This is Mednections, your primary care provider has submitted a referral to you. Please call us back at . . . to schedule your appointment". |
| If the patient responds "No" to "a good time to schedule" and refuses to provide a new date and time, the AMTVR system updates the referral status to "Patient Disregard" in the referral system. |
| The AMTVR system updates the confirmed date and time and updates the referral status to be "Scheduled & Confirmed" in the referral system. |
| If the patient responds "No" to the specialist's provided date and time for the third time, the AMTVR system updates the referral status as "Patient Disregard". |
| The AMTVR system sends data back to the referral system, and the referral system updates the referral data and sends out notifications accordingly. |
| All calls made are logged against the referral under a communication log section. |
| All calls made are recorded and saved as audio files and associated with the referral in the communication log. |
| All audio files are named with a user-identifiable name. |
| All audio files are kept in the AMTVR system for retrieval for 30 days in accordance with HIPPA regulations. |

Specialty Pharmacy Medication Verification Platform

The AMTVR provides a human interactional experience during a call to a patient to refill a medication, and capture any required information during the call. The AMTVR does not present itself as an interactive voice response (IVR) system, which would sound like a machine call requiring human interaction for specific requests during the call. The AMTVR interprets human language and conversation, picking up on keywords to respond in a conversational manner that appears to the patient as a naturally sounding conversation between two people. In reality, the interaction is between a human, such as the patient, and the AMTVR system, which is an intelligent machine.

Patients are called by the AMTVR system utilizing a database that identifies patients to be called based on refill dates associated with patients' medication requirements. The AMTVR system calls the patient utilizing one or more phone numbers within the database as well as identifying the one or more prescriptions the patient may need to have refilled.

TABLE 39

Business Requirements Description

System initiates call to the test subject.
System confirms the test subject's name. If the correct name is provided, a "Yes" response is accepted.
The test subject's demographic data, including address and date of birth, is pre-populated in the system for two-point identification purposes.
System verifies test subject's address and date of birth with the pre-populated data and completes the two-point identification before proceeding with the medication refill.
The test subject's medication is pre-populated, and the system is able to verify it with the patient.
System tells the patient the charge for the refill.
System confirms the shipping address with the patient.
System confirms an emergency contact with the patient after the refill is completed.
System asks if the patient needs any pharmacy counseling.
System asks if there is anything else the patient needs help with.

A logical outline for the AMTVR to follow during a call includes, but is not limited to, the following.

- Good morning/afternoon/evening-depending on the time of the call;
- Hi, this is Alice, I am calling from Dr. Smith's office, and I am calling you today to see if you require a refill of your medication;
- Am I speaking with Mr. Robert Thomson? (this is included to ensure that the AMTVR can pronounce the patient's last name correctly);
- Great, before I can proceed, just for privacy purposes, I need to verify I am speaking with Robert, can you please confirm your street address for me?
- Yes, my address is 1 Main Street, Newfound, Ky. 11111;
- Great, that's what I have and there is just one more item to verify;
- Can you also please verify your date of birth for me?
- Perfect, that is what I have in the database, thank you for providing the verification information needed;
- I am calling today in regards to your medication (medication name) from Doctor (physician's name), do you need a refill?
- Do you have any allergies to penicillin?
- Great, I just need to verify that you are not allergic to this medication before I refill it for you;
- Okay, I will refill your medication with your copay card, which will be thirty-five dollars;
- Let me confirm your shipping address; I have you at 1 Main Street, Newfound, Ky. 11111;
- I will send a statement to your shipping address, so that you can send a payment in for thirty-five dollars, ok?
- May I please confirm if (emergency contact information) is still your emergency contact response?
- Do you require any pharmacy counseling?
- Okay great, your medication will arrive in two business days via U.S. mail;
- Is there anything else I can help you with today? and
- Thank you for your order, I hope you have a great day/morning, afternoon/evening, good bye.

Another logical outline for the AMTVR to follow during a call includes, but is not limited to, the following.

- Good morning/afternoon/evening depending on the time of the call;
- Identify patient against database;
- Identify primary care provider against database;
- Identify patient's insurance against database;
- Identify medications for refill against database—the AMTVR is programmed with key responses based on specific medication requirements;
- AMTVR system asks the patient after its greeting to provide their name and date of birth, which is verified to correspond to information in the database;
- If verification is successful, the AMTVR system responds by thanking the patient for providing the verification;
- The AMTVR systems states that it is calling for a refill of (a medication), and asks if the patient would like to refill this medication;
- A yes response causes the AMTVR system to identify the price of the medication with insurance, a rejection of the refill request, and/or an identification of the required copayment for the patient to receive this medication;
- A "no" response from the patient initiates an AMTVR dialogue;
- The AMTVR system asks if the patient has an allergy to any medication;
- The system compares the patient's medication allergy response to medications in a database associated with the patient, and if the AMTVR system finds a match, a refill of that medication will be denied based on a history of allergy, and thus the AMTVR system understands the medication as spoken by the patient and can match that medication with the any medication that sounds the same in a list of medications associated with the patient stored in the database;
- The above process is repeated for each medication associated with the patient in the database;
- Once the patient is provided with the price of the medication, the AMTVR system identifies the medication again with the payment required to receive the medication;
- The AMTVR system requests the address to which the patient would like to ship the medication;
- If the response matches the address associated with the patient in the database, the AMTVR system proceed to collect the copayment, and if the response does not match the address associated with the patient in the database, the AMTVR system stores the patient's response as a new address for shipment and verifies the new address with the patient;
- The AMTVR proceeds by providing the amount of the copayment, and requests whether a statement for this amount should be sent to the patient or if payment will be made by credit/debit card;
- If the patient responds by requesting that a statement be sent, the AMTVR acknowledges this response and proceeds to ask that the patient update their demographic profile;

If the patient responds that payment by credit/debit card is desired, the AMTVR acknowledges this response and indicates acceptance of the credit/debit card as payment;

The AMTVR system verifies the first name on the credit/debit card;

The AMTVR system verifies the last name on the credit/debit card;

The AMTVR system verifies the credit/debit card being used;

The AMTVR system verifies the credit/debit card number;

The AMTVR system verifies the expiration date;

The AMTVR system verifies the security code

The AMTVR system verifies the amount to be charged and provides the patient with a reference number for the charge;

The AMTVR system asks if the patient has any questions regarding the medication;

The AMTVR system asks if the patient would like to add a contact number in case of an emergency; and The AMTVR system asks if there are any other issues regarding this refill.

A primary list of keywords used to guide the AMTVR system includes the following.

Hello;
Link name response to database;
Link primary care provider to database;
Link medication identification to database;
Identify a date given to match the patient's date of birth in database;
Yes;
No;
Refill;
Medication;
Price;
Cost;
Money;
Shipment;
Allergy;
Insurance;
Drug;
Statement;
Pain now;
Send;
Cancel;
Credit card;
American Express;
Visa;
Master card;
Charge;
Payment;
Receipt;
Can I;
OK;
Great;
Who;
Address;
What; and
Doctor (physician's name)

Physician Answering Service Platform

The AMTVR physician answering service platform is triggered when a patient calls the physician after office hours, in response to which the AMTVR system answers the call. The physician's demographic and contact information is stored in a database, upon which the AMTVR calls are based. This database is separate and apart from the referral platform server database.

The following keyword scenarios are handled by the AMTVR system:
appointment;
emergency;
message;
prescription/medication/refill;
pharmacy;
office hours; and
doctor's name.

Figure 16:
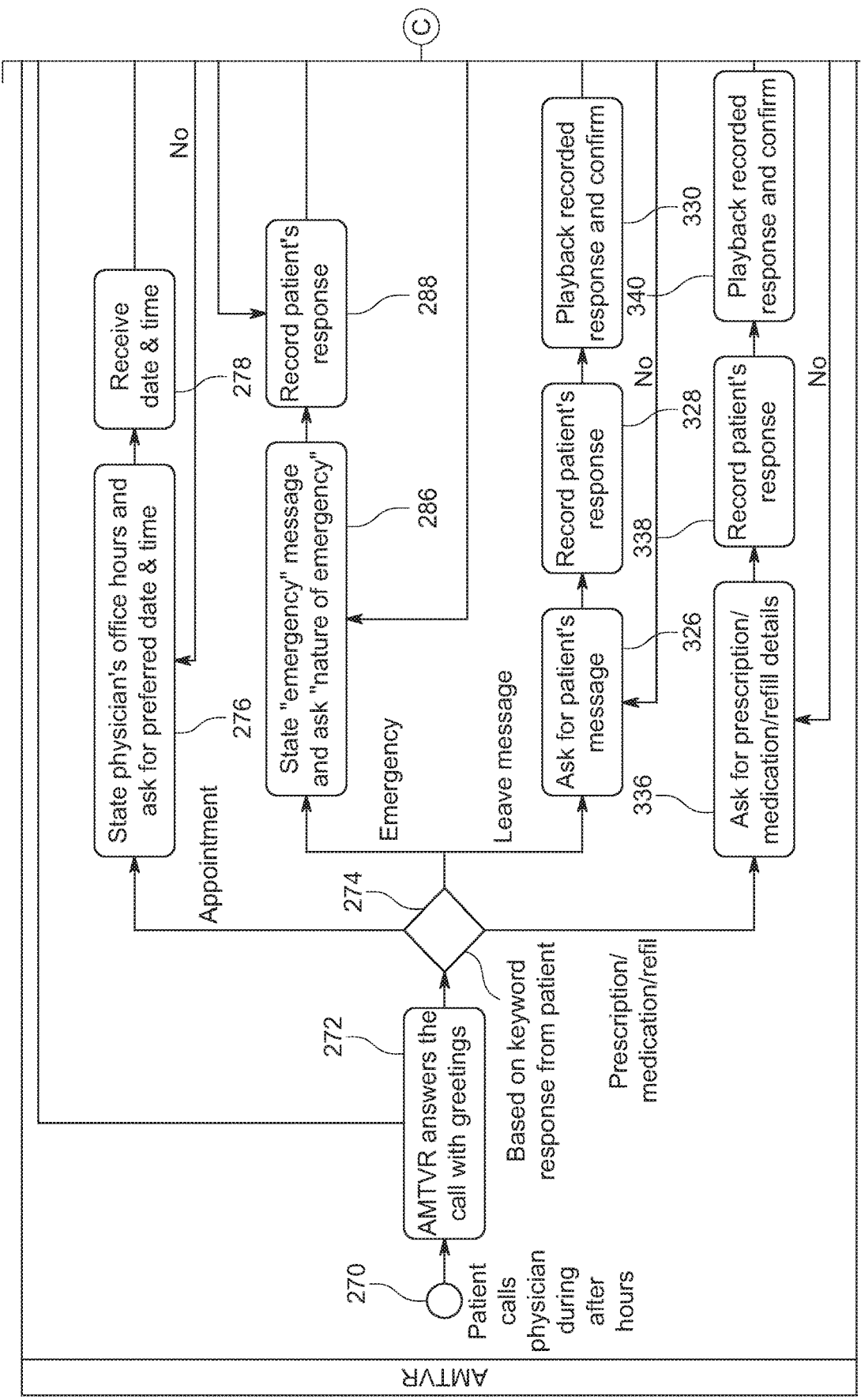
FIG. 16 is a flowchart showing operation of a physician answering service platform.
Figure 16:
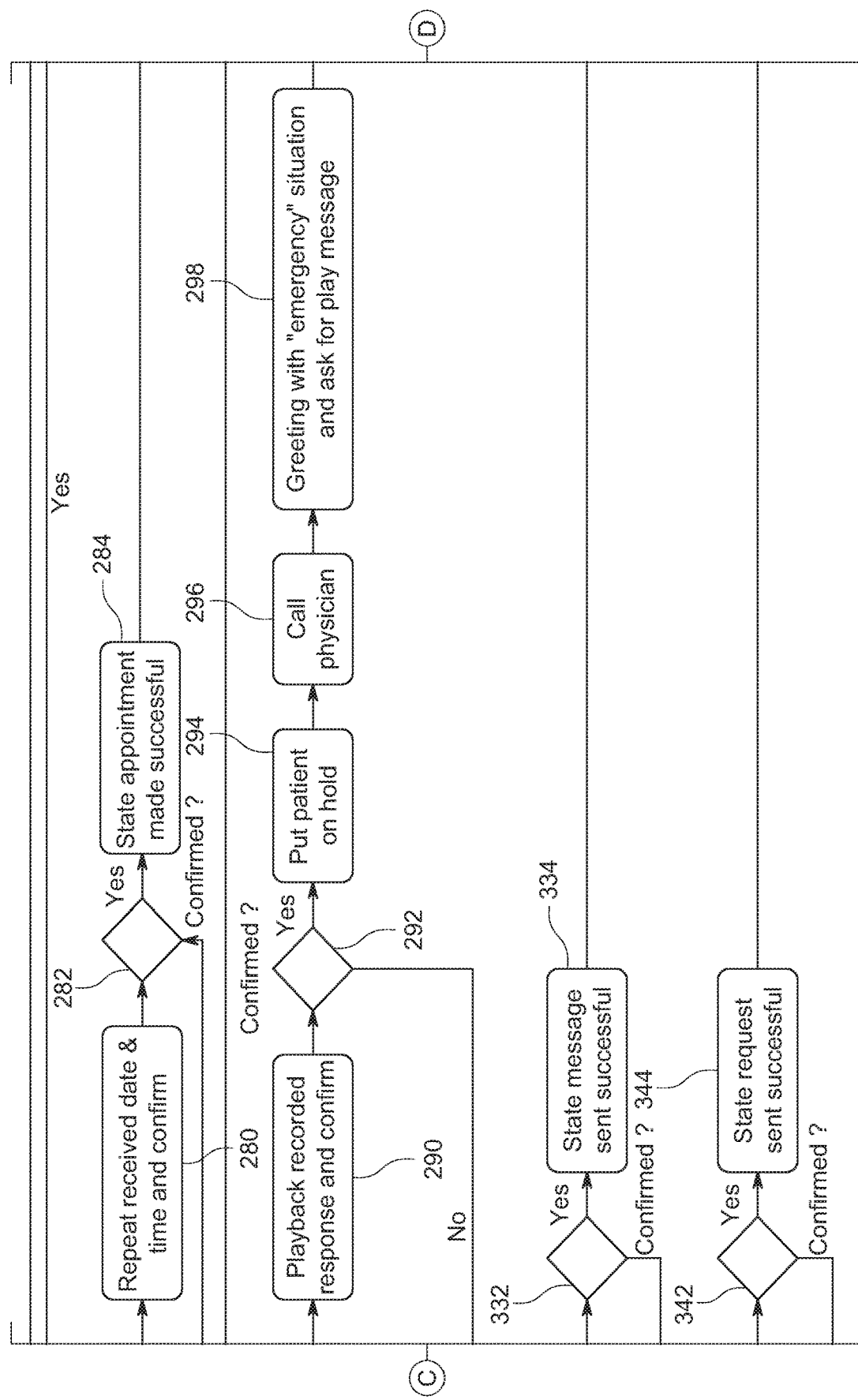
Figure 16:
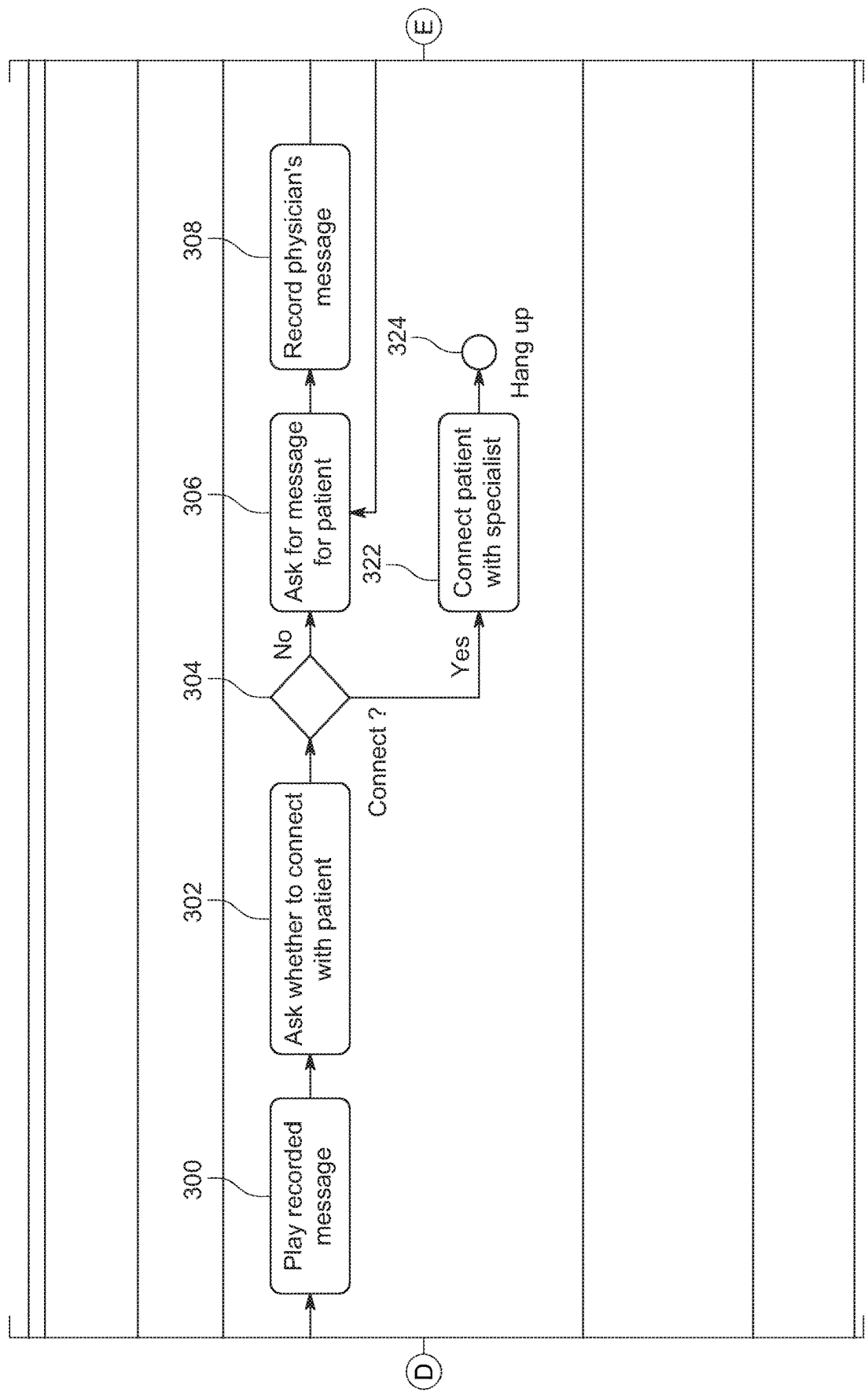
Figure 16:
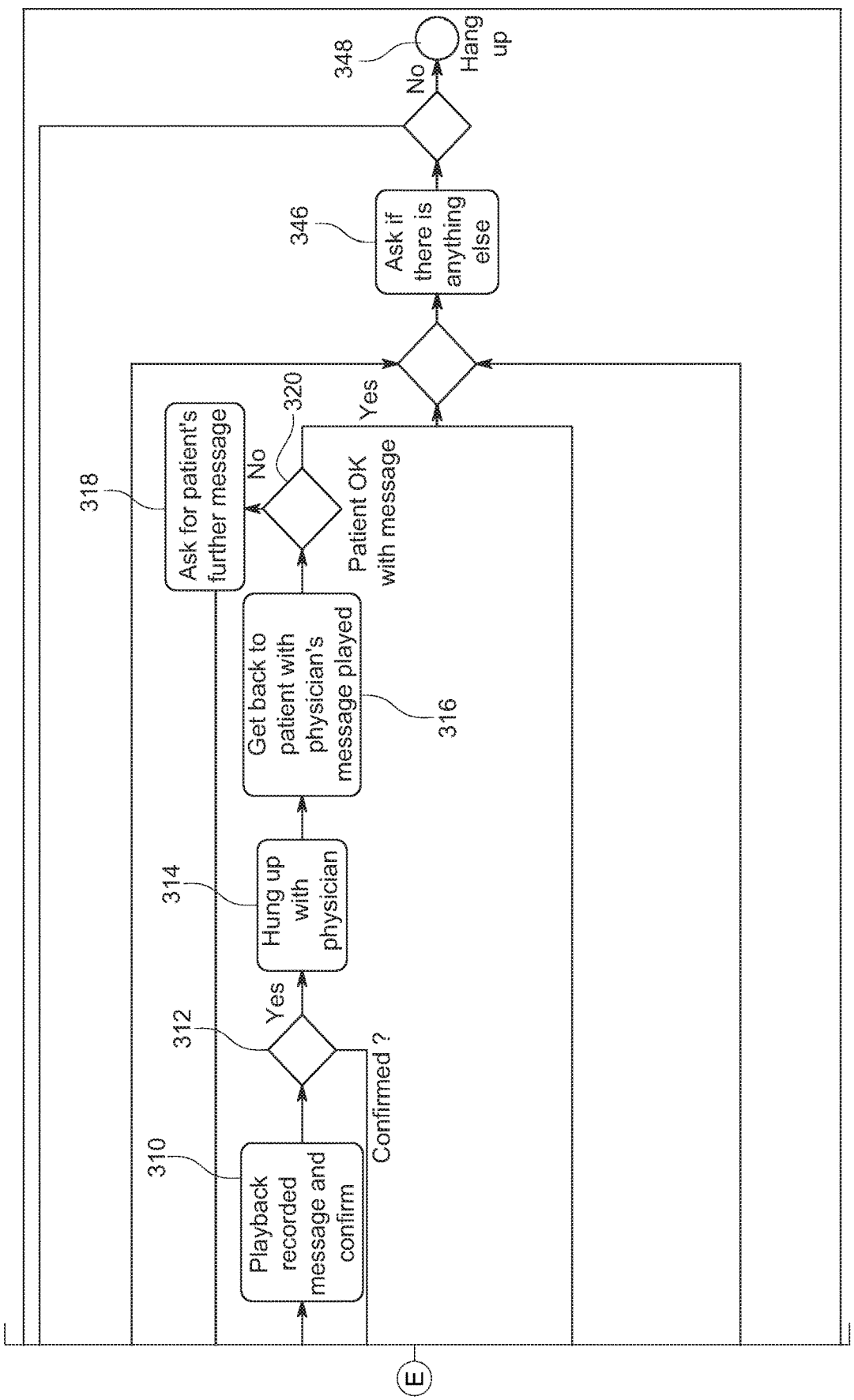
Figure 17:
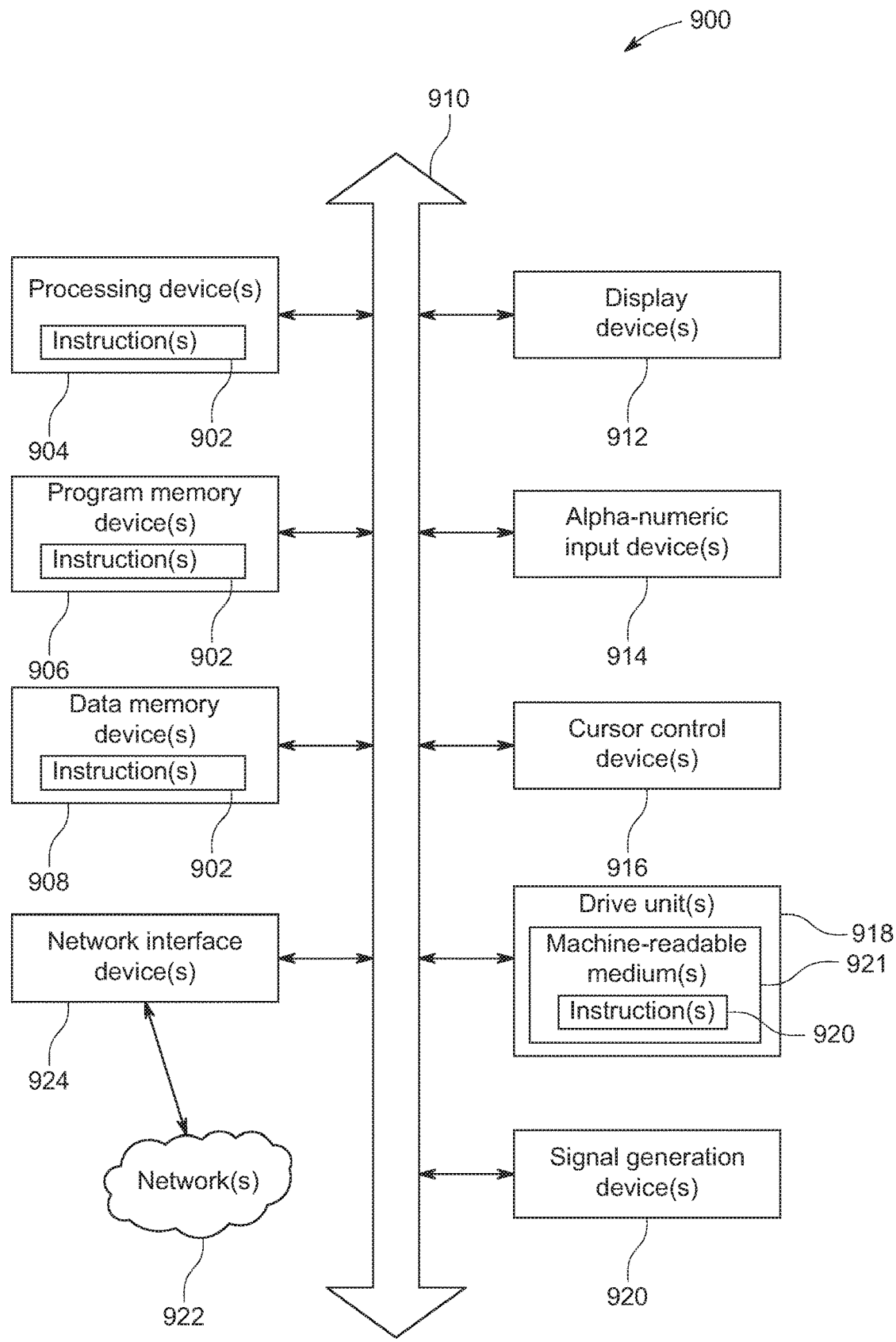
FIG. 17 is a block diagram of at least a portion of an exemplary machine in the form of a computing system that performs methods according to one or more embodiments disclosed herein.

FIG. 16 is a flowchart showing operation of the physician answering service platform. In response to the patient calling the physician's office after office hours 270, the AMTVR system answers the call with a greeting 272. Based on a keyword response from the patient 274, a scenario is selected. For an appointment scenario, the AMTVR system states the physician's office hours and asks for a preferred date and time of the appointment 276, which is received from the patient 278. The preferred date and time of the appointment is repeated 280, and if the patient confirms this information 282, the AMTVR system records the patient's appointment request, sends the request to the physician's office, and states that the appointment has been made successfully 284. If not, the process returns to step 276 until confirmation is achieved.

For an emergency scenario, the AMTVR system records the patient's emergency details and plays it to the physician, who can then decide whether to connect with the patient or pass a message to the patient. The AMTVR system states that this is an emergency message and asks for the nature of the emergency 286. The patient's response is recorded 288, played back 290, and confirmed as being correct 292. If not, the process returns to step 286 until confirmation is achieved. The patient is then placed on hold 294, the physician is called 296, a greeting indicating that this is an emergency message is played 298, the recorded message from the patient is played 300, and the physician is asked whether to connect to the patient 302. If the physician asks to be connected to the patient 304, the patient is connected to the physician 322 and the AMTVR system hangs up 324. If not, a message for the patient is requested 306, the message is recorded 308, and the message is played back for confirmation 310. If the message is confirmed 312, the call with the physician is ended 314, and the message is provided to the patient 316. If the message is not confirmed, the process returns to step 306 until confirmation is achieved. If the patient is satisfied with the physician's message 320, the process continues and, if not, the process requests another message from the patient and returns to step 288 until the patient is satisfied.

For a message scenario, the AMTVR system records the patient's message and sends it to the physician's office. The patient is asked for a message 326, the patient's response is recorded 328, and the response is played back for confirmation 330. If the message is confirmed 332, the AMTVR sends the message, and states that the message has been sent successfully 334. If not, the process returns to step 326 until confirmation is achieved.

For a prescription/medication/refill scenario, the AMTVR system records the Patient's refill and pharmacy request and sends it to the physician's office. The patient is asked for details concerning the prescription/medication/refill 336, the patient's response is recorded 338, and the response is played back for confirmation 340. If the message is confirmed 342, the AMTVR sends the prescription/medication/ refill request and states that the request has been sent successfully 344. If not, the process returns to step 336 until confirmation is achieved.

For an office hours scenario, the AMTVR system states the physician's office hours. For a physician's name scenario, the AMTVR system asks for details regarding the physician from the patient. At the end of the scenarios, the AMTVR system asks if there is anything else the patient needs 346 and, if so, returns to step 272. If not, the call is ended 348.

The inputs for the AMTVR Answering Service Process include the following:

The Physician's demographic information, including office hours, names, etc.; and The Physician's contact information.

The outputs for the AMTVR physician answering service platform include the messages and conversations recorded. The roles and responsibilities involved in this process include the following:

AMTVR, which answers the call;
the patient, who calls the physician; and
the physician, who may be contacted if there is an emergency.

TABLE 40

| Business Rules Description |
| --- |
| AMTVR answers the call after office hours. |
| The following keyword are included in the AMTVR system workflow: |
| appointment |
| emergency |
| refill |
| pharmacy |
| office hours |
| Dr. [physician's name] |
| message |
| Patient profile is created and stored. |
| Physician logins are created and stored. |

TABLE 41

| Business Requirements Description |
| --- |
| AMTVR receives calls from patients by recognizing keywords, and conducts a conversation based on the keywords. |
| AMTVR records name and phone number from patient. |
| AMTVR places patient on hold and contacts physician via text or cell phone based on prior required demographic information for the physician. Once patient is placed on hold, the AMTVR contacts the physician and relays the patient's message depending on a keyword for action. |
| AMTVR provides the physician with an option to connect with the patient or give instructions to the AMTVR system to relay to the patient. |
| AMTVR provides the physician with an option to connect the patient and the physician at the request of the physician . |
| AMTVR system, based on keywords, sends a text or fax to the physician's office requesting an appointment for the patient or a medication refill. The AMTVR instructs the patient regarding office hours of operation. |
| AMTVR conducts a conversational response and associated action based on the following keywords received: |
| appointment |
| emergency |
| refill |
| pharmacy |
| office hours |
| Dr. [physician's name] |
| message |
| Conversation dialogue between the AMTVR and patient is formatted for each keyword and there is a default dialogue for the AMTVR so that there is always a conversation even if the conversation defaults to "How can I help you?". |
| Detailed actions and workflows are provided for each keyword. |
| The AMTVR system sends a message to the physician's office staff via text or fax. |
| The AMTVR system sends a text to the physician requesting a medication refill. |

TABLE 42

| Business Requirement Description |
| --- |
| Based on the office hours defined for each Physician, the AMTVR system answers the call. |
| AMTVR system states the physician's name when answering the call. |
| For responses received, AMTVR system records and replays the message for confirmation. |
| Based on the keyword "appointment", AMTVR system states the physician's office hours and asks for a preferred date and time from the patient. |
| For "appointment" scenario, AMTVR system collects the patient information, including the patient's name and phone number. |
| With appointment date and time confirmed by the patient, AMTVR system sends the appointment request with recorded message to the physician. |
| Based on the keyword "emergency", AMTVR system asks for the nature of the emergency. |

TABLE 42-continued

Business Requirement Description

For "emergency" situation, AMTVR system calls the physician and plays the recorded message from the patient.
For "emergency" situation, AMTVR system asks the physician whether to connect with the patient.
For "emergency" situation, if the physician answers "No" when asked whether to connect with the patient, AMTVR system asks for a message from the physician to be sent to the patient.
For "emergency" situation, if the physician decides "Yes" to connect with the patient, AMTVR system calls the patient and connects the patient with the physician.
Based on the keyword "message", AMTVR system asks for the message, records and plays back the message, and sends the message to the physician.
Based on the keyword "refill" or "pharmacy", AMTVR system asks for details, records and plays back the message, and sends the refill/pharmacy request to Physician.
Based on the keyword "office hours", AMTVR system states the physician's office hours to the patient.
Based on the keyword "Doctor [physician's name]", AMTVR system asks for more specific reason, and then acts based on the keywords received.
At the end of the conversation, AMTVR system asks the patient if there is anything else.
AMTVR system differentiates "messages" that physicians need to take care of, and "recorded conversations" that require no action.
AMTVR system categorizes the following types of "messages":
appointment request
general message
refill/pharmacy request
conversation message: messages recorded during conversation, but no actions required
AMTVR system stops speaking and listens for another keyword in response to being interrupted.
While patient is placed on hold, AMTVR system replays the office hours of the physician in addition to services performed by the physician, looping with music therein.

A logical outline for the AMTVR to follow during a call includes, but is not limited to, the following.
Greeting:
AMTVR: Hello this is Alice, you have reached "Dr. Lippoff's" office, however, it is after regular hours, and the office is now closed. Items framed with quotes are obtained by the AMTVR from demographic information associated with the physician and are stored within the answering service platform, which includes the physician's office hours.
Exemplary Patient Responses:
Patient: This is an "emergency" I need to reach Dr. "Lippoff".
AMTVR: OK, I do understand you are having an emergency, if you are in any distress I would suggest you dial 911 or go to the nearest emergency room. However, I can reach Dr. "Lippoff" and relay your emergency message to him at this time. What is the nature of your "emergency"? AMTVR awaits a response, proceeds to record the patient's statement, and after a few seconds of silence, the AMTVR responds with the following.
AMTVR: Okay, I have your message. Is this what you want to tell Dr. "Lippoff"? AMTVR then plays the patient's recording back.
Patient: "Yes"
AMTVR: Please hold on while I contact Dr. "Lippoff".
Patient: "No"
AMTVR: Can you please repeat your message for Dr. "Lippoff"? I want to be sure I give him your correct message. Following which the AMTVR repeats the repeated message.
Patient: repeats message
AMTVR: Okay, is this your message? Following which the AMTVR repeats the repeated message.
Patient: "Yes"
AMTVR: The patient is placed on hold, during which the physician's office hours and services are provided to the patient, which are repeated in a message loop with music inserted between the looped messages.
AMTVR: contacts Dr. "Lippoff".
AMTVR: Hello Dr. "Lippoff", this is Alice from the answering service, I have a patient on hold who states it is an emergency and she needs to speak with you. I have a message for you, can I play this message?
Doctor: "Yes"
AMTVR: Plays the patient's message, and after two seconds of silence, the AMTVR asks the following.
AMTVR: Dr. "Lippoff" do you want me to connect you with the patient?
Doctor: "Yes"
AMTVR: Connects the patient to the physician and completes the AMTVR's intervention with the call.
Doctor: "No"
AMTVR: Dr. "Lippoff", please tell me what you wish to tell the patient.
Doctor: Provides a message for the patient
AMTVR: Plays back the message for the patient just recorded from the physician.
AMTVR: Is this the message for the patient?
Doctor: "Yes"
AMTVR: Okay, I will relay your message to the patient. The AMTVR then ends the call with the physician, and proceeds with the patient's call.
AMTVR: I have spoken with Dr. "Lippoff" and he wishes you to know the following. The AMTVR then plays the physician's message.
Patient: Okay, following which the patient ends the call.
Patient: "No", I must speak with the "doctor".
AMTVR: Please tell me what you need to ask or tell the doctor, I will relay the message again.
Patient: "Makes a statement"
AMTVR: Is this what you want me to, tell Dr "Lippoff"?
AMTVR: Plays back the patient's message.
Patient: "Yes"

AMTVR: Okay, please hold on I will call back "Dr "Lippoff". The cycle repeats until the patient hangs up or the physician connects with the patient. This back-and-forth exchange occurs while the physician and/or patient remains on hold or the AMTVR may call the physician and/or patient back when reconnecting with the physician and/or patient.
Additional Patient Responses Following the Greeting:

Patient: I need to make an "appointment" with Dr. "Lippoff"

AMTVR: Dr. "Lippoff" will be in the office on the following days and times. Can you please tell me which date and time are good for you?

Patient: Provides a "response date and time".

AMTVR: Repeats back date and time provided by the patient and asks Is this the day and time you are requesting?

Patient: "Yes"

AMTVR: Okay, I will relay this information to the office, and you will be called back with a conformation when the office opens. Is there anything else I can help you with?

Patient: "No"

AMTVR: Okay, thank you, following which the AMTVR ends the call. If the patient responds "Yes" to the AMTVR question "Is there anything else I can help you with at this time?", the AMTVR repeats the greeting and this cycle until the patient responds "No" to the question "Is there anything else I can help you with at this time?"

Additional Patient Questions:

The patient may also respond to the initial greeting as follows.

Patient: I need to leave a "message" for Dr. "Lippoff".

AMTVR: Okay, what is your message?

Patient: The patient then states their message.

AMTVR: Records this message and plays the message back to the patient for confirmation.

AMTVR: Is this your message?

Patient: "Yes"

AMTVR: Acknowledges and again asks "Is there anything else I can help you with?".

Patient: "No"

AMTVR: Okay, thank you, following which the AMTVR ends the call.

Patient: "Yes"

AMTVR: Returns to the greeting

Additional Patient Responses:

The patient may also respond to the initial greeting as follows.

Patient: I need a "medication" (or "prescription").

AMTVR: Okay, what medication do you require?

Patient: The patient then states what medication the patient needs.

AMTVR: Records this message and plays the message back to the patient for confirmation. Is this the medication you require?

Patient: "Yes"

AMTVR: Your medication refill request will be transmitted to the physician's office and to the physician.

AMTVR: Is there anything else I can help you with?

Patient: "No"

AMTVR: Thank you, following which the AMTVR ends the call.

Patient: "Yes" AMTVR: Returns to the greeting.

Information relayed on the phone and appointment scheduling information are recorded by the answering service platform server.

Additional embodiments of the subject matter disclosed herein are, for example, similarly applicable, but not limited to, one or more of the following implementations.

practice management module-verification of insurance claim status;

physician office appointment scheduling and verification;

patient access to laboratory and clinical information;

authorization verifications;

follow-up patient visit checking patient status;

verifications for medication refills with patients;

hospital follow-up after patient discharge with verification patient follow-up primary care physician;

ability to communicate with patients' various disabilities for status updates and additional medical modality requests for specialty in subspecialty referrals and authorizations;

specific referral module relating to workers compensation referrals and authorizations; and patient helpline to guide patients through various modalities of care options and medical requirements in accordance with patient pathology.

Additional vertical platforms utilizing the AMTVR system may include, for example, insurance claim adjudication. Specifically, the AMTVR system may be used to replace receivable coordinators and physicians' offices that would call an insurance company to verify open receivables and payment information. Currently, human receivable coordinators work from an aged run for patient's outstanding balances from insurance companies. Depending on the age of the claim and the amount of the claim, the human coordinator calls the insurance company and specifies a date of service, patient name, date of birth, and the patient's insurance identification number. The coordinator then provides a specific date of service, for which there is an outstanding payment due.

A dialog with then ensue between the receivable coordinator and the person at the insurance company to determine if payment was made on a claim, if the patient's insurance deductible is due, if there is a copayment for the patient, and/or if there is missing billing information preventing the claim from being paid. The AMTVR accomplishes these tasks and coordinates with a physician's practice management software, from which the AMTVR system accesses patient demographic information as the AMTVR system relates to outstanding receivables within the practice management software to confirm and coordinate payment and provide additional and/or missing information to process the claim.

Additional vertical platforms utilizing the AMTVR system may further include, for example, appointment visit confirmation. Specifically, the AMTVR system calls patients to confirm patients' appointments with their primary care or sub-specialty provider, and interfaces with physicians' offices to populate, based on the physician's schedule, the status of an appointment. The AMTVR system also enables the patient to change their appointments when confirming the appointments on the day prior to their appointment.

Additional vertical platforms utilizing the AMTVR system may yet further include, for example, a patient satisfaction survey. Specifically, the AMTVR system contacts patients after their appointments to a physician to check their status and, with key phrases, reviews and follows-up with the patient based on a specific diagnosis obtained from the database. For example, if a patient is diagnosed with bronchitis and prescribed medication, the patient will be queried if the patient still has a cough or fever. The patient is given specific information and/or information based on their response. Also depending on the patient's response, the patient may be connected directly to the physician for a follow-up, or the patient may be directed to return to the office for a follow-up visit.

Additional vertical platforms utilizing the AMTVR system may yet further include, for example, payers and independent physician association (IPA) tracking. Specifically, the AMTVR system enables an insurance company or IPA to call patients to verify their satisfaction with treatment received from providers. Depending on key phrases that are asked of the patient and possible patient responses, the AMTVR system categorizes the physician's treatment of the patient in accordance with the patient's satisfaction with that care.

A so-called "bot" or "robot" is a software application that runs tasks and/or scripts. One bot is utilized in the AMTVR system to attend to a current level of call traffic, and thus the sequences for calls are in stack order for the bot. In response to a sufficient volume of additional or fewer calls, the AMTVR system may recruit additional or fewer bots to complete calls as required during a business day.

One or more embodiments disclosed herein, or a portion thereof, may make use of software running on a computer or workstation. By way of example, only and without limitation, FIG. 18 is a block diagram of an embodiment of a machine in the form of a computing system 900, within which is a set of instructions 902 that, when executed, cause the machine to perform any one or more of the methodologies according to embodiments of the invention. In one or more embodiments, the machine operates as a standalone device; in one or more other embodiments, the machine is connected (e.g., via a network 922) to other machines. In a networked implementation, the machine operates in the capacity of a server or a client user machine in a server-client user network environment. Exemplary implementations of the machine as contemplated by embodiments of the invention include, but are not limited to, a server computer, client user computer, personal computer (PC), tablet PC, personal digital assistant (PDA), cellular telephone, mobile device, palmtop computer, laptop computer, desktop computer, communication device, personal trusted device, web appliance, network router, switch or bridge, or any machine capable of executing a set of instructions (sequential or otherwise) that specify actions to be taken by that machine.

The computing system 900 includes a processing device(s) 904 (e.g., a central processing unit (CPU), a graphics processing unit (GPU), or both), program memory device(s) 906, and data memory device(s) 908, which communicate with each other via a bus 910. The computing system 900 further includes display device(s) 912 (e.g., liquid crystal display (LCD), flat panel, solid state display, or cathode ray tube (CRT)). The computing system 900 includes input device(s) 914 (e.g., a keyboard), cursor control device(s) 916 (e.g., a mouse), disk drive unit(s) 918, signal generation device(s) 920 (e.g., a speaker or remote control), and network interface device(s) 924, operatively coupled together, and/or with other functional blocks, via bus 910.

The disk drive unit(s) 918 includes machine-readable medium(s) 926, on which is stored one or more sets of instructions 902 (e.g., software) embodying any one or more of the methodologies or functions herein, including those methods illustrated herein. The instructions 902 may also reside, completely or at least partially, within the program memory device(s) 906, the data memory device(s) 908, and/or the processing device(s) 904 during execution thereof by the computing system 900. The program memory device(s) 906 and the processing device(s) 904 also constitute machine-readable media. Dedicated hardware implementations, such as but not limited to ASICs, programmable logic arrays, and other hardware devices can likewise be constructed to implement methods described herein. Applications that include the apparatus and systems of various embodiments broadly comprise a variety of electronic and computer systems. Some embodiments implement functions in two or more specific interconnected hardware subsystems or devices with related control and data signals communicated between and through the subsystems, or as portions of an ASIC. Thus, the example system is applicable to software, firmware, and/or hardware implementations.

The term "processing device" as used herein is intended to include any processor, such as, for example, one that includes a CPU (central processing unit) and/or other forms of processing circuitry. Further, the term "processing device" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the display device(s) 912, input device(s) 914, cursor control device(s) 916, signal generation device(s) 920, etc., can be collectively referred to as an "input/output interface," and is intended to include one or more mechanisms for inputting data to the processing device(s) 904, and one or more mechanisms for providing results associated with the processing device(s). Input/output or I/O devices (including but not limited to keyboards (e.g., alpha-numeric input device(s) 914, display device(s) 912, and the like) can be coupled to the system either directly (such as via bus 910) or through intervening input/output controllers (omitted for clarity).

In an integrated circuit implementation of one or more embodiments of the invention, multiple identical dies are typically fabricated in a repeated pattern on a surface of a semiconductor wafer. Each such die may include a device described herein and may include other structures and/or circuits. The individual dies are cut or diced from the wafer, then packaged as integrated circuits. One skilled in the art would know how to dice wafers and package die to produce integrated circuits. Any of the exemplary circuits or method illustrated in the accompanying figures, or portions thereof, may be part of an integrated circuit. Integrated circuits so manufactured are considered part of this invention.

In accordance with various embodiments, the methods, functions or logic described herein is implemented as one or more software programs running on a computer processor. Dedicated hardware implementations including, but not limited to, application specific integrated circuits, programmable logic arrays and other hardware devices can likewise be constructed to implement the methods described herein. Further, alternative software implementations including, but not limited to, distributed processing or component/object distributed processing, parallel processing, or virtual machine processing can also be constructed to implement the methods, functions or logic described herein.

The embodiment contemplates a machine-readable medium or computer-readable medium including instructions 902, or that which receives and executes instructions 902 from a propagated signal so that a device connected to a network environment 922 can send or receive voice, video or data, and to communicate over the network 922 using the instructions 902. The instructions 902 are further transmitted or received over the network 922 via the network interface device(s) 924. The machine-readable medium also contains a data structure for storing data useful in providing a functional relationship between the data and a machine or computer in an illustrative embodiment of the systems and methods herein.

While the machine-readable medium 902 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding, or carrying a set of instructions for execution by the machine and that cause the machine to perform anyone or more of the methodologies of the embodiment. The term "machine-readable medium" shall accordingly be taken to include, but not be limited to: solid-state memory (e.g., solid-state drive (SSD), flash memory, etc.); read-only memory (ROM), or other non-volatile memory; random access memory (RAM), or other re-writable (volatile) memory; magneto-optical or optical medium, such as a disk or tape; and/or a digital file attachment to e-mail or other self-contained information archive or set of archives is considered a distribution medium equivalent to a tangible storage medium. Accordingly, the embodiment is considered to include anyone or more of a tangible machine-readable medium or a tangible distribution medium, as listed herein and including art-recognized equivalents and successor media, in which the software implementations herein are stored.

It should also be noted that software, which implements the methods, functions and/or logic herein, are optionally stored on a tangible storage medium, such as: a magnetic medium, such as a disk or tape; a magneto-optical or optical medium, such as a disk; or a solid state medium, such as a memory automobile or other package that houses one or more read-only (non-volatile) memories, random access memories, or other re-writable (volatile) memories. A digital file attachment to e-mail or other self-contained information archive or set of archives is considered a distribution medium equivalent to a tangible storage medium. Accordingly, the disclosure is considered to include a tangible storage medium or distribution medium as listed herein and other equivalents and successor media, in which the software implementations herein are stored.

Although the specification describes components and functions implemented in the embodiments with reference to particular standards and protocols, the embodiments are not limited to such standards and protocols.

The foregoing description relates to select exemplary embodiments. Those skilled in the art will understand that certain modifications may be made without departing from the spirit and scope of the invention.

Every document cited herein, including any cross referenced or related patent or application, is hereby incorporated herein by reference in its entirety unless expressly excluded or otherwise limited, The citation of any document is not an admission that it is prior art with respect to any invention disclosed or claimed herein or that it alone, or any combination with any other reference or references, teaches, suggests, or discloses any such invention. Further, to the extent conflicts with any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments are utilized and derived therefrom, such that structural and logical substitutions and changes are made without departing from the scope of this disclosure. Figures are also merely representational and are not drawn to scale. Certain proportions thereof are exaggerated, while others are decreased. Accordingly, the specification and drawings are to be regarded in an illustrative rather than a restrictive sense.

Such embodiments are referred to herein, individually and/or collectively, by the term "embodiment" merely for convenience and without intending to voluntarily limit the scope of this application to any single embodiment or inventive concept if more than one is in fact shown. Thus, although specific embodiments have been illustrated and described herein, it should be appreciated that any arrangement calculated to achieve the same purpose are substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single embodiment. Thus, the following claims are hereby incorporated into the detailed description, with each claim standing on its own as a separate example embodiment.

The abstract is provided to comply with 37 C.F.R. § 1.72(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single embodiment. Thus, the following claims are hereby incorporated into the Detailed Description, with each claim standing on its own as separately claimed subject matter.

Although specific example embodiments have been described, it will be evident that various modifications and changes are made to these embodiments without departing from the broader scope of the inventive subject matter described herein. Accordingly, the specification and drawings are to be regarded in an illustrative rather than a restrictive sense. The accompanying drawings that form a part hereof, show by way of illustration, and without limitation, specific embodiments in which the subject matter are practiced. The embodiments illustrated are described in sufficient detail to enable those skilled in the art to practice the teachings herein. Other embodiments are utilized and derived therefrom, such that structural and logical substitutions and changes are made without departing from the scope of this disclosure. This Detailed Description, therefore, is not to be taken in a limiting sense, and the scope of various embodiments is defined only by the appended claims, along with the full range of equivalents to which such claims are entitled.

Every document cited herein, including any cross referenced or related patent or application, is hereby incorporated herein by reference in its entirety unless expressly excluded or otherwise limited, The citation of any document is not an admission that it is prior art with respect to any invention disclosed or claimed herein or that it alone, or any combination with any other reference or references, teaches, suggests, or discloses any such invention. Further, to the extent conflicts with any meaning or definition of a term in this document conflicts with any meaning or definition of the same term in a document incorporated by reference, the meaning or definition assigned to that term in this document shall govern.

Given the teachings provided herein, one of ordinary skill in the art will be able to contemplate other implementations and applications of the techniques of the disclosed embodiments. Although illustrative embodiments have been described herein with reference to the accompanying drawings, it is to be understood that these embodiments are not limited to the disclosed embodiments, and that various other changes and modifications are made therein by one skilled in the art without departing from the scope of the appended claims.

What is claimed is:

1. A computer system comprising:
   a client-side presentation layer processor;
   a server-side service layer component comprising at least one application programming interface (API) controller, at least one repository pattern processor, and a data layer processor; and
   a back-end layer component comprising at least one structured query language (SQL) server and a cache, wherein the client-side presentation layer processor is operable to initiate a call with a patient, to process conversation of the patient, to retrieve first dialogues from the SQL server based on the conversation of the patient, to interact with the patient using the first dialogues, to automatically initiate a call with a physician based on the interaction with the patient, to process conversation of the physician, to retrieve second dialogues from the SQL server based on the conversation of the physician, to interact with the physician using the second dialogues, and to schedule an appointment for the patient with the physician based on the interaction with the physician,
   wherein the client-side presentation layer processor comprises an appointment monitoring and tracking voice recognition (AMTVR) system that is operable to intake the patient as a new referral, to determine that an insurance authorization pertaining to the appointment of the patient is required, to automatically transmit a notification to a referral coordination manager (RCM) when the insurance authorization is required, to process an authorization from the RCM, and to add the patient to a call queue to initiate the call with the patient in response to processing the authorization by the RCM.

2. The computer system as defined by claim 1, wherein the at least one API controller provides at least one of application security or authentication.

3. The computer system as defined by claim 1, wherein the server-side service layer component validates an insurance authorization status associated with at least one of the patient or a referral.

4. The computer system as defined by claim 1, wherein the server-side service layer component utilizes a URL hyperlink to submit a referral request.

5. The computer system as defined by claim 1, wherein the client-side presentation layer processor transmits a special note provided by a primary care provider to a specialist that provides referral coordination, the special note comprising information associated with at least one of a physical examination or a diagnostic study based on patient pathology.

6. The computer system as defined by claim 1, wherein demographic information associated with the physician and demographic information associated with the patient is provided by a referral system to the server-side service layer component.

7. The computer system as defined by claim 1, wherein, in response to at least one of the patient refusing to make an appointment or the patient could not be reached, the client-side presentation layer transmits a notification to a primary care provider identifying the patient and at least one of that the patient refused to make a referral appointment or that the patient could not be reached.

8. The computer system as defined by claim 1, wherein, in response to the patient being unreachable, the client-side presentation layer processor transmits a notification to at least one of a primary care provider or the patient indicating an inability to coordinate a referral request by the primary care provider.

9. The computer system as defined by claim 1, wherein the client-side presentation layer processor initiates a call to the physician after placing an active call to the patient on hold.

10. The computer system as defined by claim 1, wherein the client-side presentation layer processor initiates a call to the patient after placing an active call to the physician on hold.

11. The computer system as defined by claim 1, wherein the client-side presentation layer processor alternates between picking up active calls with at least one of a physician's office or the patient until an agreement is reached between the physician's office.

12. The computer system as defined by claim 11, wherein the agreement is associated with at least one of a date or a time of an appointment for the patient with the physician.

13. The computer system as defined by claim 1, wherein the client-side presentation layer processor confirms at least one of a date or a time of an appointment with at least one of the physician or the patient.

14. The computer system as defined by claim 1, wherein an authorization associated with the patient's referral is hard-coded in software based on insurance associated with the patient.

15. The computer system as defined by claim 1, wherein the client-side presentation layer processor causes a dual-tone multi-frequency (DTMF) tone, the DTMF tone generated in response to interfacing with at least one of an interactive voice response (IVR) system, music on hold, or an answering machine.

16. The computer system as defined by claim 15, wherein the DTMF tone represents at least one of 0, 1, or 9.

17. The computer system as defined by claim 15, wherein the DTMF tone represents a digital tone associated with access to at least one of an operator or a receptionist, thereby attempting to establish connection with a person.

18. The computer system as defined by claim 1, wherein the client-side presentation layer processor waits a predetermined time period for a person to answer a call in response to interfacing with at least one of an interactive voice response (IVR) system, music on hold, or an answering machine before advising the patient that an appointment cannot be made.

19. A computer system, comprising:
a client-side presentation layer processor;
a server-side service layer component comprising at least one application programming interface (API) controller, at least one repository pattern processor, and a data layer processor; and
a back-end layer component comprising at least one structured query language (SQL) server and a cache, wherein the client-side presentation layer processor is operable to initiate a call with a patient, to process conversation of the patient, to retrieve first dialogues from the SQL server based on the conversation of the patient, to interact with the patient using the first dialogues, to automatically initiate a call with a physician based on the interaction with the patient, to process conversation of the physician, to retrieve second dialogues from the SQL server based on the conversation of the physician, to interact with the physician using the second dialogues, and to schedule an appointment for the patient with the physician based on the interaction with the physician,
wherein the client-side presentation layer processor comprises an appointment monitoring and tracking voice recognition (AMTVR) system that is operable to intake the patient as a new referral, to determine that an insurance authorization pertaining to the appointment of the patient is required, to automatically transmit a notification to a referral coordination manager (RCM) when the insurance authorization is required, to process an authorization from the RCM, and to add the patient to a call queue to initiate the call with the patient in response to processing the authorization by the RCM.

20. A method, comprising:
via a client-side presentation layer processor:
initiating a call with a patient;
processing conversation of the patient;
retrieving first dialogues from a structured query language (SQL) server based on the conversation of the patient;
interacting with the patient using the first dialogues;
automatically initiating a call with a physician based on the interaction with the patient;
processing conversation of the physician;
retrieving second dialogues from the SQL server based on the conversation of the physician;
interacting with the physician using the second dialogues; and
scheduling an appointment for the patient with the physician based on the interaction with the physician; and
via an appointment monitoring and tracking voice recognition (AMTVR) system of the client-side presentation layer processor:
intaking the patient as a new referral;
determining that an insurance authorization pertaining to the appointment of the patient is required;
automatically transmitting a notification to a referral coordination manager (RCM) when the insurance authorization is required;
processing an authorization from the RCM; and
adding the patient to a call queue to initiate the call with the patient in response to processing the authorization by the RCM.

* * * * *